US011376308B2

(12) United States Patent
Robson et al.

(10) Patent No.: US 11,376,308 B2
(45) Date of Patent: Jul. 5, 2022

(54) USE OF FKBP-L POLYPEPTIDES AND NUCLEIC ACIDS FOR THE TREATMENT OF OBESITY

(71) Applicant: The Queen's University of Belfast, Belfast (GB)

(72) Inventors: Tracy Robson, Belfast (GB); David Grieve, Hillsborough Down (GB); Amy Short, Magerafelt Londonderry (GB); Adrien Kissenpfennig, Belfast (GB); Marie Migaud, Lurgan Armagh (GB); Rachel Bennett, Antrim (GB); Anita Yakkundi, Belfast (GB); Helen McCarthy, Newtonabbey (GB)

(73) Assignee: Royal College of Surgeons in Ireland, Dublin (IE)

( * ) Notice: Subject to any disclaimer, the term of this patent is extended or adjusted under 35 U.S.C. 154(b) by 0 days.

(21) Appl. No.: 16/343,266

(22) PCT Filed: Oct. 18, 2017

(86) PCT No.: PCT/GB2017/053157
§ 371 (c)(1), (2) Date: Apr. 18, 2019

(87) PCT Pub. No.: WO2018/073591
PCT Pub. Date: Apr. 26, 2018

(65) Prior Publication Data

US 2019/0247462 A1 Aug. 15, 2019

(30) Foreign Application Priority Data

Oct. 19, 2016 (GB) ..................................... 1617726
Oct. 20, 2016 (GB) ..................................... 1617761

(51) Int. Cl.
*A61K 38/17* (2006.01)
*A61P 3/04* (2006.01)
*A61P 3/10* (2006.01)
*A61K 9/00* (2006.01)

(52) U.S. Cl.
CPC ........ *A61K 38/1709* (2013.01); *A61K 9/0019* (2013.01); *A61K 38/17* (2013.01); *A61P 3/04* (2018.01); *A61P 3/10* (2018.01)

(58) Field of Classification Search
None
See application file for complete search history.

(56) References Cited

U.S. PATENT DOCUMENTS

2009/0192085 A1 * 7/2009 Robson ............. A61K 38/1709 514/8.2

FOREIGN PATENT DOCUMENTS

WO WO-2007141533 A2 12/2007
WO WO-2010133880 A1 11/2010
WO WO-2014/087023 A1 6/2014
WO WO-2016007644 A1 1/2016

OTHER PUBLICATIONS

NHS (<https://www.nhs.uk/conditions/obesity/> May 2019).*
Merck Manual (https://www.merckmanuals.com/home/digestive-disorders/tumors-of-the-digestive-system/colorectal-cancer Jul. 2019).*
Merck Manual (<https://www.merckmanuals.com/professional/musculoskeletal-and-connective-tissue-disorders/joint-disorders/osteoarthritis-oa> May 2020).*
Kastelan et al. ("Anti-Inflammatory Therapy in Diabetic Retinopathy"; Hindawi Publishing Corporation Mediators of Inflammation; vol. 2013).*
Robson et al., "The therapeutic and diagnostic potential of FKBPL; a novel anticancer protein", Drug Discovery Today, vol. 17, Nos. 11/12, Jun. 2012, pp. 544-548.
Yakkundi et al., "FKBPL Is a Critical Antiangiogenic Regulator of Developmental and Pathological Angiogenesis", Arteriosclerosis, Thrombosis, and Vascular Biology, Apr. 1, 2015, pp. 845-854.
Schnack, Anne, "International Search Report" for PCT/GB2017/053157 as dated Dec. 22, 2017, 5 pages.
Rodriguez, Amaia, et al., "Revisiting the Adipocyte: A Model for Integration of Cytokine Signalling in the Regulation of Energy Metabolism," American Journal of Physiology—Endocrinology and Metabolish, 2015, 309: E691-E714.
Xiaoling, Li, Acta Biochim Biophys Sin (Shanghai), "SIRTI and Energy Metabolism," Jan. 2013., 45(1): 51-60.
Lemoine, A.Y., et al., "Adipose Tissue Angiogenesis in Obesity," Thrombosis and Haemostasis, Oct. 2013, 110(4):661-668.
Sung, Hoon-Ki, et al., "Adipose Vascular Endothelial Growth Factor Regulates Metabolic Homeostasis Through Angiogenesis," Jan. 8, 2013, Cell Metabolism 17, pp. 61-72.
Cao, Y., "Angiogenesis Modulates Adipogenesis and Obesity," The Journal of Clinical Investigation, Sep. 2007, vol. 117, pp. 2362-2368.
Xue, Y., et al., "Hypoxia-Independent Angiogenesis in Adipopse Tissues During Cold Acclimation," Cell Matab. 9, pp. 99-109 (2009).
The Expert Committee on the Diagnosis and Classification of Diabetes Mellitus, "Report of the Expert Committee on the Diagnosis and Classification of Diabetes Mellitus," Diabetes Care, vol. 26, Supplement 1, Jan. 2003, 16 pages.

(Continued)

*Primary Examiner* — Julie Ha
*Assistant Examiner* — Tara L Martinez
(74) *Attorney, Agent, or Firm* — Winstead PC

(57) ABSTRACT

The inventors have determined that increasing the expression level or activity of FKBP-L polypeptide in a subject, which can be provided by expression of nucleic acids encoding FKBP-L or by providing FKBP-L polypeptides to a subject is advantageous for use in the treatment of obesity and obesity-related disorders. In particular increased expression or activity of FKBP-L polypeptide in a subject may be used to treat excessive weight gain (which can be characterised as obesity), glucose intolerance, diabetes and metabolic syndrome, which are closely linked to obesity and insulin resistance. FKBP-L can also be used as a biomarker for obesity and obesity-related disorders.

3 Claims, 24 Drawing Sheets

Specification includes a Sequence Listing.

(56) References Cited

OTHER PUBLICATIONS

Pearson, William R., et al., "Improved Tools for Biological Sequence Comparison," National Biomedical Research Foundation, Proc. Natl. Acad. Sci. USA, vol. 85:2444-2448, Apr. 1988.
BLAST: Basic Local Alignment Search Tool, May 14, 2019, three pages.
ENTREZ: Molecular Sequence Database System, <URL: http://www.ncbi.nlm.nih.gov/Entrez/>, May 14, 2019.
"Recommended Classifications for BMI in Humans: The Evidence Report," NIH Publication No. 98-4083, Sep. 1998, National Institutes of Health, 262 pages.
NHLBI Obesity Education Initiative, "The Practical Guide to the Identification, Evaluation, and Treatment of Overweight and Obesity in Adults," National Institutes of Health, Oct. 2000, 94 pages.
Ausubel, et al., "Current Protocols in Molecular Biology," eds. John Wiley & Sons, 1992, 4648 pages.
Molecular Cloning: A Laboratory Manual, 3rd edition, Sambrook, et al., Cold Spring Harbour Laboratory Press, 2000, 34 pages.
Pasut, G., et al., "Polymer-Drug Conjugatino, Recent Achievements and General Strategies," Progress in Polymer Science, 2007, 32 (8-9): 933-961.
Clinical Guidelines on the Identification, Evaluation, and Treatment of Overweight and Obesity in Adults: Executive Summary 1-3, Expert Panel on the Identification, Evaluation and Treatment of Overweight in Adults, Am. J. Clin. Nutr. 1998; 68:899-917.
Ort, Tatiana, et al.; "Recombinant Human FIZZ3/Resistin Stimulates Lipolysis in Cultured Human Adipocytes, Mouse Adipose Explants, and Normal Mice"; Endocrinology 146(5); Feb. 10, 2005; pp. 2200-2209.
Smith, T.F., et al.; "Identification of Common Molecular Subsequences"; J. Mol. Biol. 147(1); Mar. 25, 1981; pp. 195-197.
Wang, Hui et al.; "Endostatin Prevents Dietary-Induced Obesity by Inhibiting Adipogenesis and Angiogenesis"; Diabetes; vol. 64; Jul. 2015; pp. 2442-2456.
Rupnick, Maria A. et al.; "Adipose tissue mass can be regulated through the vasculature"; PNAS; vol. 99 No. 16; Aug. 6, 2002; pp. 10730-10735.
Wu, Chun-Yan et al.; "Comparative proteome analysis of abdominal adipose tissues between fat and lean broilers"; Proteome Science; vol. 14 No. 9; 2016; 9 pages.

* cited by examiner

Figure 8A

SEQ ID NO: 1 MRGSHHHHHHGMASMTGGQQMGRDLYDDDDKDRWGSMETPPVNTIGEKDTSQPQQEWEKNLRENLDSVI
QIRQQPRDPPTETLELEVSPDPASQILEHTQGAEKLVAELEGDSHKSHGSTSQMPEALQASDLWYCPDG
SFVKKIVIRGHGLDKPKLGSCCRVLALGFPFGSGPPEGWTELTMGVGPWREETWGELIEKCLESMCQGE
EAELQLPGHTGPPVGLTLASFTQGRDSWELETSEKEALAREERARGTELFRAGNPEGAARCYGRALRLL
LTLPPPGPPERTVLHANLAACQLLLGQPQLAAQSCDRVLEREPGHLKALYRRGVAQAALGNLEKATADL
KKVLAIDPKNRAAQEELGKVVIQGKNQDAGLAQGLRKMFG

SEQ ID NO: 2 METPPVNTIGEKDTSQPQQEWEKNLRENLDSVIQIRQQPRDPPTETLELEVSPDPASQILEHTQGAEKLV
AELEGDSHKSHGSTSQMPEALQASDLWYCPDGSFVKKIVIRGHGLDKPKLGSCCRVLALGFPFGSGPPEG
WTELTMGVGPWREETWGELIEKCLESMCQGEEAELQLPGHTGPPVGLTLASFTQGRDSWELETSEKEALA
REERARGTELFRAGNPEGAARCYGRALRLLLTLPPPGPPERTVLHANLAACQLLLGQPQLAAQSCDRVLE
REPGHLKALYRRGVAQAALGNLEKATADLKKVLAIDPKNRAAQEELGKVVIQGKNQDAGLAQGLRKMFG

SEQ ID NO: 3 METPPVNTIGEKDTSQPQQEWEKNLRENLDSVIQIRQQPRDPPTETLELEVSPDPASQILEHTQGAEKLV
AELEGDSHKSHGSTSQMPEALQASDLWYCPDGSFVKKIVIRGHGLDKPKLGSCCRVLALGFPFGSGPPEG
WTELTMGVGPWREETWGELIEKCLESMCQGEEAELQLPGHTGPPVGLTLASFTQGRDSW
A200
FKBP-L

SEQ ID NO: 4 METPPVNTIGEKDTSQPQQEWEKNLRENLDSVIQIRQQPRDPPTETLELEVSPDPASQILEHTQGAEKLV
AELEGDSHKSHGSTSQMPEALQASDLWYCPDGSFVKKIVIRGHGLDKPKLGSCCRVLALGFPFGSGPPEG
WTELTMGVGP
A151
FKBP-L

SEQ ID NO: 5 METPPVNTIGEKDTSQPQQEWEKNLRENLDSVIQIRQQPRDPPTETLELEVSPDPASQILEHTQGAEKLV
AELEGDSHKSHGSTS
A86
FKBP-L

SEQ ID NO: 6 METPPVNTIGEKDTSQPQQEWEKNLRENLDSVIQIRQQPRDPPTETLELEVSPDPAS
A58
FKBP-L

SEQ ID NO: 7 METPPVNTIGEKDTSQPQQEWEKNLRENLDSVIQIRQQPRDPPTETL
A48
FKBP-L

SEQ ID NO: 8 METPPVNTIGEKDTSQPQQEWEKNLRENLDSVIQIRQQP
A40
FKBP-L

SEQ ID NO: 9 METPPVNTIGEKDTSQPQQEWEKNLRENLDSVI
A34
FKBP-L

SEQ ID NO: 10 QIRQQPRDPPTETLELEVSPDPAS
FKBP-L 24mer

| | | |
|---|---|---|
| SEQ ID NO: 11 | QQPRDPPTETLELEVSPD | |
| SEQ ID NO: 12 | QIRQQPRDPPTETLELEVSPDPAS-PEG-C(Alexa488) | Peptide 1 |
| SEQ ID NO: 13 | PyroGlu-IRQQPRDPPTETLELEVSPDPAS | Peptide 2 |
| SEQ ID NO: 14 | IRQQPRDPPTETLELEVSPDPAS | Peptide 3 |
| SEQ ID NO: 15 | QIRQQPRDPPTETLELEVSPD | Peptide 4 |
| SEQ ID NO: 16 | QIRQQPRDPPTETLELEV | Peptide 5 |
| SEQ ID NO: 17 | QIRQQPRDPPTETLE | Peptide 6 |
| SEQ ID NO: 18 | QIRQQPRDPPTE | Peptide 7 |
| SEQ ID NO: 19 | QQPRDPPTETLELEVSPDPAS | Peptide 8 |
| SEQ ID NO: 20 | RDPPTETLELEVSPDPAS | Peptide 9 |
| SEQ ID NO: 21 | PTETLELEVSPDPAS | Peptide 10 |
| SEQ ID NO: 22 | TLELEVSPDPAS | Peptide 11 |
| SEQ ID NO: 23 | RQQPRDPPTETLELEVSPD | Peptide 12 |
| SEQ ID NO: 24 | RQQPRDPPTETLELEVSP | Peptide 13 |
| SEQ ID NO: 25 | RQQPRDPPTETLELEVS | Peptide 14 |
| SEQ ID NO: 26 | PRDPPTETLELEVSPD | Peptide 15 |
| SEQ ID NO: 27 | RDPPTETLELEVSPD | Peptide 16 |

Figure 8B

| | | |
|---|---|---|
| SEQ ID NO: 28 | Ac-QIRQQPRDPPTETLELEVSPDPAS-$NH_2$ | Peptide 17 |
| SEQ ID NO: 29 | METPPVNTIGEKDTSQPQQEWEKNLRENLDSVIQIRQQPRDPPTETLELEVSPDPASQILEHTQGAEKLV<br>AELEGDSHKSHGSTSQMPEALQASDLWYCPDGSFVKKIVIRGHGLDKPKLGSCCRVLALGFPFGSGPPEG<br>WTELTMGVGPWREETWGELIEKCLESMCQGEEAELQLPGH**S**GPPV**R**LTLASFTQGRDSWELETSEKEALA<br>REERARGTELFRAGNPEGAARCYGRALRLLLTLPPPGPPERTVLHANLAACQLLLGQPQLAAQSCDRVLE<br>REPGHLKALYRRGVAQAALGNLEKATADLKKVLAIDPKNRAAQEELGKVVIQGKNQDAGLAQGLRKMFG | PUBMED database |

Figure 8C

SEQ ID NO: 30 Full-length FKBPL cDNA (PUBMED Database)

ATGGAGACGCCACCAGTCAATACAATTGGAGAAAAGGACACCTCTCAGCCGCAACAAGAGTGGAAAAGA
ACCTTCGGGAGAACCTTGATTCAGTTATTCAGATTAGGCAGCAGCCCCGAGACCCTCCTACCGAAACGCT
TGAGCTGGAAGTAAGCCCAGATCCAGCCAGCCAAATTCTAGAGCATACTCAAGGAGCTGAAAAACTGGTT
GCTGAACTTGAAGGAGACTCTCATAAGTCTCATGGATCAACCAGTCAGATGCCAGAGGCCCTTCAAGCTT
CTGATCTCTGGTACTGCCCCGATGGGAGCTTTGTCAAGAAGATCGTAATCCGTGGCCATGGCTTGGACAA
ACCCAAACTAGGCTCCTGCTGCCGGGTACTGGCTTTGGGGTTTCCTTTCGGATCAGGGCCGCCAGAGGGC
TGGACAGAGCTAACTATGGCGTAGGGCCATGGAGGGAGGAAACTTGGGGGGAGCTCATAGAGAAATGCT
TGGAGTCCATGTGTCAAGGTGAGGAAGCAGAGCTTCAGCTGCCTGGGCACTCTGGACCTCCTGTCAGGCT
CACACTGGCATCCTTCACTCAAGGCCGAGACTCCTGGGAGCTGGAGACTAGCGAGAAGGAAGCCCTGGCC
AGGGAAGAACGTGCAAGGGGCACAGAACTATTTCGAGCTGGGAACCCTGAAGGAGCTGCCCGATGCTATG
GACGGGCTCTTCGGCTGCTCCTGACTTTACCCCCACCTGGCCCTCCAGAACGAACTGTCCTTCATGCCAA
TCTGGCTGCCTGTCAGTTGTTGCTAGGGCAGCCTCAGTTGGCAGCCCAGAGCTGTGACCGGGTGTTGGAG
CGGGAGCCTGGCCATTTAAAGGCCTTATACCGAAGGGGGGTTGCCCAGGCTGCCCTTGGGAACCTGGAAA
AAGCAACTGCTGACCTCAAGAAGGTGCTGGCGATAGATCCCAAAAACCGGGCAGCCCAGGAGGAACTGGG
GAAGCTGGTCATTCAGGGGAAGAACCAGGATGCAGGGCTGGCTCAGGGTCTGCGCAAGATGTTTGGCTGA

Figure 9A

SEQ ID NO: 31 Full-length FKBPL cDNA

ATGGAGACGCCACCAGTCAATACAATTGGAGAAAAGGACACCTCTCAGCCGCAACAAGAGTGGGAAAAGA
ACCTTCGGGAGAACCTTGATTCAGTTATTCAGATTAGGCAGCAGCCCCGAGACCCTCCTACCGAAACGCT
TGAGCTGGAAGTAAGCCCAGATCCAGCCAGCCAAATTCTAGAGCATACTCAAGGAGCTGAAAAACTGGTT
GCTGAACTTGAAGGAGACTCTCATAAGTCTCATGGATCAACCAGTCAGATGCCAGAGGCCCTTCAAGCTT
CTGATCTCTGGTACTGCCCCGATGGGAGCTTTGTCAAGAAGATCGTAATCCGTGGCCATGGCTTGGACAA
ACCCAAACTAGGCTCCTGCTGCCGGGTACTGGCTTTGGGGTTTCCTTTCGGATCAGGGCCGCCAGAGGGC
TGGACAGAGCTAACTATGGGCGTAGGGCCATGGAGGGAGGAAACTTGGGGGGAGCTCATAGAGAAATGCT
TGGAGTCCATGTGTCAAGGTGAGGAAGCAGAGCTTCAGCTGCCTGGGCACACTGGACCTCCTGTCGGGCT
CACACTGGCATCCTTCACTCAAGGCCGAGACTCCTGGGAGCTGGAGACTAGCGAGAAGGAAGCCCTGGCC
AGGGAAGAACGTGCAAGGGGCACAGAACTATTTCGAGCTGGGAACCCTGAAGGAGCTGCCCGATGCTATG
GACGGGCTCTTCGGCTGCTCCTGACTTTACCCCCACCTGGCCCTCCAGAACGAACTGTCCTTCATGCCAA
TCTGGCTGCCTGTCAGTTGTTGCTAGGGCAGCCTCAGTTGGCAGCCCAGAGCTGTGACCGGGTGTTGGAG
CGGGAGCCTGGCCATTTAAAGGCCTTATACCGAAGGGGGGTTGCCCAGGCTGCCCTTGGGAACCTGGAAA
AAGCAACTGCTGACCTCAAGAAGGTGCTGGCGATAGATCCCAAAAACCGGGCAGCCCAGGAGGAACTGGG
GAAGGTGGTCATTCAGGGGAAGAACCAGGATGCAGGGCTGGCTCAGGGTCTGCGCAAGATGTTTGGCTGA

Figure 9B

SEQ ID NO: 32 Δ34 FKBPL
ATGGAGACGCCACCAGTCAATACAATTGGAGAAAAGGACACCTCTCAGCCGCAACAAGAGTGGGAAAAG
AACCTTCGGGAGAACCTTGATTCAGTTATTTAG

SEQ ID NO: 33 Δ40 FKBPL
ATGGAGACGCCACCAGTCAATACAATTGGAGAAAAGGACACCTCTCAGCCGCAACAAGAGTGGGAAAAG
AACCTTCGGGAGAACCTTGATTCAGTTATTCAGATTAGGCAGCAGCCCCG

SEQ ID NO: 34 Δ48 FKBPL
ATGGAGACGCCACCAGTCAATACAATTGGAGAAAAGGACACCTCTCAGCCGCAACAAGAGTGGGAAAAG
AACCTTCGGGAGAACCTTGATTCAGTTATTCAGATTAGGCAGCAGCCCCGAGACCCTCCTACCGAAACG
CTTGA

SEQ ID NO: 35 Δ58 FKBPL
ATGGAGACGCCACCAGTCAATACAATTGGAGAAAAGGACACCTCTCAGCCGCAACAAGAGTGGGAAAAG
AACCTTCGGGAGAACCTTGATTCAGTTATTCAGATTAGGCAGCAGCCCCGAGACCCTCCTACCGAAACG
CTTGAGCTGGAAGTAAGCCCAGATCCAGCCAGCTAA

SEQ ID NO: 36 Δ86 FKBPL
ATGGAGACGCCACCAGTCAATACAATTGGAGAAAAGGACACCTCTCAGCCGCAACAAGAGTGGGAAAAG
AACCTTCGGGAGAACCTTGATTCAGTTATTCAGATTAGGCAGCAGCCCCGAGACCCTCCTACCGAAACG
CTTGAGCTGGAAGTAAGCCCAGATCCAGCCAGCCAAATTCTAGAGCATACTCAAGGAGCTGAAAAACTG
GTGCTGAACTTGAAGGAGACTCTCATAAGTCTCATGGATCAACCAGTTAG

Figure 9C

SEQ ID NO: 37 Δ151 FKBPL

ATGGAGACGCCACCAGTCAATACAATTGGAGAAAAGGACACCTCTCAGCCGCAACAAGAGTGGGAAAAG
AACCTTCGGGAGAACCTTGATTCAGTTATTCAGATTAGGCAGCAGCCCCGAGACCCTCCTACCGAAACG
CTTGAGCTGGAAGTAAGCCCAGATCCAGCCAGCCAAATTCTAGAGCATACTCAAGGAGCTGAAAAACTG
GTTGCTGAACTTGAAGGAGACTCTCATAAGTCTCATGGATCAACCAGTCAGATGCCAGAGGCCCTTCAA
GCTTCTGATCTCTGGTACTGCCCCGATGGGAGCTTTGTCAAGAAGATCGTAATCCGTGGCCATGGCTTG
GACAAACCCAAACTAGGCTCCTGCTGCCGGGTACTGGCTTTGGGGTTTCCTTTCGGATCAGGGCCGCCA
GAGGGCTGGACAGAGCTAACTATGGGCGTAGGGCCATGA

SEQ ID NO: 38 Δ200 FKBPL (PUBMED Database)

ATGGAGACGCCACCAGTCAATACAATTGGAGAAAAGGACACCTCTCAGCCGCAACAAGAGTGGGAAAAG
AACCTTCGGGAGAACCTTGATTCAGTTATTCAGATTAGGCAGCAGCCCCGAGACCCTCCTACCGAAACG
CTTGAGCTGGAAGTAAGCCCAGATCCAGCCAGCCAAATTCTAGAGCATACTCAAGGAGCTGAAAAACTG
GTTGCTGAACTTGAAGGAGACTCTCATAAGTCTCATGGATCAACCAGTCAGATGCCAGAGGCCCTTCAA
GCTTCTGATCTCTGGTACTGCCCCGATGGGAGCTTTGTCAAGAAGATCGTAATCCGTGGCCATGGCTTG
GACAAACCCAAACTAGGCTCCTGCTGCCGGGTACTGGCTTTGGGGTTTCCTTTCGGATCAGGGCCCCCA
GAGGGCTGGACAGAGCTAACTATGGGCGTAGGGCCATGGAGGGAGGAAACTTGGGGGGAGCTCATAGAG
AAATGCTTGGAGTCCATGTGTCAAGGTGAGGAAGCAGAGCTTCAGCTGCCTGGGCACTCTGGACCTCCT
GTCAGGCTCACACTGGCATCCTTCACTCAAGGCCGAGACTCCTGGTAG

Figure 9D

SEQ ID NO: 39 Δ200 FKBPL which was cloned into pcDNA3.1

ATGGAGACGCCACCAGTCAATACAATTGGAGAAAAGGACACCTCTCAGCCGCAACAAGAGTGGGAAAAGA
ACCTTCGGGAGAACCTTGATTCAGTTATTCAGATTAGGCAGCAGCCCCGAGACCCTCCTACCGAAACGCT
TGAGCTGGAAGTAAGCCCAGATCCAGCCAGCCAAATTCTAGAGCATACTCAAGGAGCTGAAAAACTGGTT
GCTGAACTTGAAGGAGACTCTCATAAGTCTCATGGATCAACCAGTCAGATGCCAGAGGCCCTTCAAGCTT
CTGATCTCTGGTACTGCCCCGATGGGAGCTTTGTCAAGAAGATCGTAATCCGTGGCCATGGCTTGGACAA
ACCCAAACTAGGCTCCTGCTGCCGGGTACTGGCTTTGGGGTTTCCTTTCGGATCAGGGCCGCCAGAGGGC
TGGACAGAGCTAACTATGGGCGTAGGGCCATGGAGGGAGGAAACTTGGGGGGAGCTCATAGAGAAATGCT
TGGAGTCCATGTGTCAAGGTGAGGAAGCAGAGCTTCAGCTGCCTGGGCACACTGGACCTCCTGTCGGGCT
CACACTGGCATCCTTCACTCAAGGCCGAGACTCCTGGTAG

Figure 9E

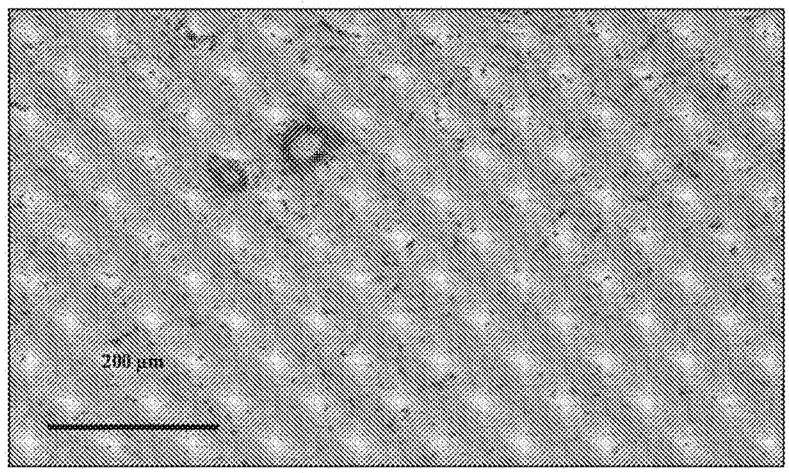
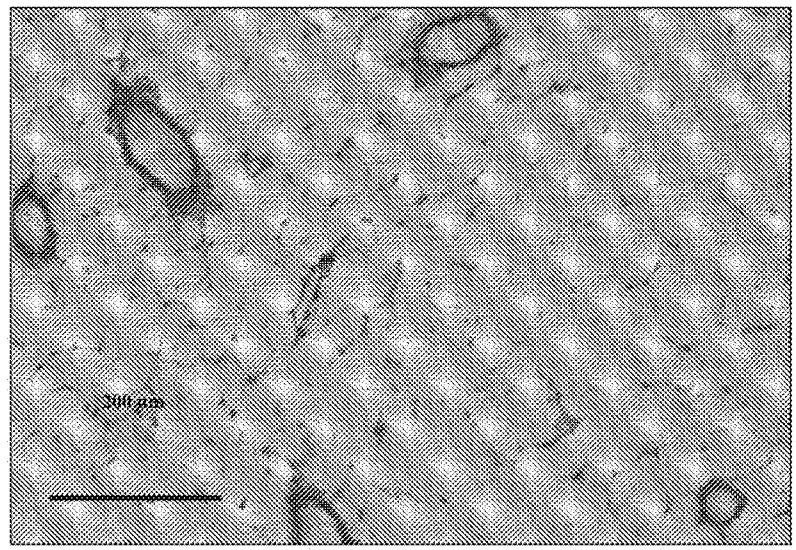
Figure 10

USE OF FKBP-L POLYPEPTIDES AND NUCLEIC ACIDS FOR THE TREATMENT OF OBESITY

FIELD OF THE INVENTION

The present invention relates to the use of FKBP-L polypeptides or nucleic acids encoding FKBP-L for treating obesity and obesity-related disorders. In a further aspect, the invention is concerned with the use of FKBP-L polypeptides or nucleic acids encoding FKBP-L as a biomarker for obesity and obesity-related disorders.

BACKGROUND OF THE INVENTION

Obesity can be described as a state of excessive accumulation of body fat (weight gain), and is widely considered to be a major public health problem, being associated with substantially increased morbidity and mortality, as well as psychological problems, reduced economic achievement, and discrimination.

Obesity disrupts many body systems including glucose and lipid metabolism, circadian rhythms and liver function. It also causes or increases inflammation and oxidative stress.

Examples of health and social problems thought to be caused or exacerbated by obesity (obesity related disorders) include coronary heart disease, stroke, obstructive sleep apnea, diabetes mellitus type 2, gout, hyperlipidemia, osteoarthritis, reduced fertility, impaired psychosocial function, reduced physical agility and increased risk of accidents, impaired obstetrical performance, reduced economic performance and discrimination and prejudice. One of the strongest links is with type 2 diabetes. Increases in body fat alter the body's response to insulin, potentially leading to insulin resistance. As a result, obesity has been found to reduce life expectancy.

The global economic cost of obesity is estimated to be $2 trillion annually. Causes of obesity remain unclear, however whether obesity is of genetic origin or is promoted by a genotype-environment interaction, or both, it remains true that energy intake must have exceeded metabolic and physical (work) energy expenditure for there to have been surplus energy available for fat deposition.

Methods for managing body weight by dietary restriction and/or by exercise are largely ineffective as few people stick to dietary regimens for a long time, and compliance to regular exercise is equally poor.

The result is generally a transient phase of weight loss (or weight stability) followed by a return on the trajectory towards obesity. These failures have highlighted the need for safe anti-obesity therapies.

SUMMARY OF THE INVENTION

The inventors have now unexpectedly found that increasing the expression level or activity of FKBP-L polypeptide in a subject, which can be provided by expression of nucleic acids encoding FKBP-L or by providing FKBP-L polypeptides to a subject is advantageous for use in the treatment of obesity and obesity-related disorders. In particular increased expression or activity of FKBP-L polypeptide in a subject may be used to treat excessive weight gain (which can be characterised as obesity), glucose intolerance, diabetes and metabolic syndrome, which are closely linked to obesity and insulin resistance.

More particularly, the inventors have found that isolated FKBP-L polypeptides or a biologically active fragment of FKBP-L polypeptide or a biologically active derivative thereof, or a biologically active derivative of a fragment of FKBP-L or a nucleic acid encoding such an FKBP-L polypeptide are useful in the treatment of obesity and obesity-related disorders. Likewise, the inventors consider a deficiency in the FKBP-L gene causes obesity, and thus the level of FKBP-L or reduced functionality within FKBP-L, as a result of a mutation or single nucleotide polymorphism can be used as an indicator for obesity risk.

FKBP-L belongs to the family of FK506 binding proteins and it is an important regulator of angiogenesis, targeting the CD44 pathway (Arteriosclerosis Thrombosis and Vascular Biology April; 35(4):845-54). FKBP-L is a divergent member of this protein family with very different functions from other family members for example FKBP11 and FKBP4.

Without wishing to be bound by theory, it is considered that adipose tissue mass is determined by two mechanisms: hypertrophy (increase in size of adipocytes) and hyperplasia (increase in adipocyte number) (Amaia Rodriguez, Silvia Ezquerro, Leire Méndez-Giménez, Sara Becerril, Gema Frühbeck Revisiting the adipocyte: a model for integration of cytokine signalling in the regulation of energy metabolism, American Journal of Physiology—Endocrinology and Metabolism, 2015 309, 8, E691-E714 DOI:10.1152/ajpendo.00297.2015). Hypertrophy is considered to be the main contributor to adipose tissue enlargement and is associated with abnormal adipocyte function, increased basal fatty acid release, pro-inflammatory cytokine release, immune cell recruitment, hypoxia, fibrosis, decreased adiponectin, and impaired insulin sensitivity. Enhanced angiogenesis does not correlate with hypertrophy. The inventors have found that FKBP-L-mediates effects on adiposity with $Fkbpl^{+/-}$ mice demonstrating a significant increase in the number and size of adipocytes.

Thus, inhibition of angiogenesis is not the driver for the FKBP-L-mediated protection against obesity.

Furthermore, WAT from these mice clearly demonstrate hypertrophic tissue expansion. Deregulation of FKBP-L levels might inhibit adipogenesis which is strongly associated with adipocyte hypertrophy as observed in the FKBP-L deficient mice ($Fkbpl^{+/-}$) mice.

Furthermore, an impaired local proinflammatory response in the adipocyte leads to increased ectopic lipid accumulation, glucose intolerance, and systemic inflammation. Adipocyte hypertrophy and hypoxia provide ideal environments for the development of adipose tissue inflammation, by promoting the influx of macrophages and other immune cells. The inflammation is mediated by producing a large number of cytokines and chemokines which in turn promote further recruitment of pro-inflammatory immune cells into the adipose tissue. The inventors have shown that FKBP-L/ALM201 regulates cytokine networks associated with obesity, reducing secreted leptin, TIMP1 and IL-8 levels.

FKBP-L fragments—for example AD-01 (24 aa peptide)—can inhibit lipopolysaccharide induced NFkB signalling in the THP1 monocyte cell line and this results in a dramatic reduction in the pro-inflammatory cytokine IL-1β secretion. Macrophages within the adipose tissue are polarized to the M1 inflammatory phenotype, producing this proinflammatory cytokine. The inventors therefore consider endogenous FKBP-L and its therapeutic peptides may also be protective of obesity through abrogation of inflammatory signalling in both adipocytes and macrophages.

It is further considered that FKBP-L and its peptides can protect against TLR-mediated signalling pathway associated with obesity, leading to reduced NFkB signalling and IL-1β secretion. The mechanism by which IL-1β is secreted, culminates from the activation of a common receptor complex, the NLRP3 inflammasome, triggered by Toll-like receptor activation. TLR receptors, initially thought to be involved in recognizing microbial danger signals, may also mediate immune responses to endogenous danger signals, including those arising in metabolic dysfunction, such as T2D.

It is further considered that FKBP-L can regulate SIRT1 levels. SIRT1 is a protein deacetylase which controls both glucose and lipid metabolism in the liver, promotes fat mobilization and stimulates brown remodeling of the white fat in white adipose tissue, controls insulin secretion in the pancreas, senses nutrient availability in the hypothalamus, influences obesity-induced inflammation in macrophages, and modulates the activity of circadian clock in metabolic tissues (Xiaoling Li, Acta Biochim Biophys Sin (Shanghai) SIRT1 and energy metabolism). 2013 January; 45(1): 51-60. doi: 10.1093/abbs/gms108 PMCID: PMC3527007). The inventors consider that when FKBP-L levels are low, as observed in FKBPL+/− mice, SIRT1 levels fall. This fall in SIRT1 could also help to explain the weight gain in our mice and the glucose intolerance. FKBPL-1 polypeptides (ALM201) can increase SIRT1 levels.

WO 2007141533 discloses the use of FKBP-L polypeptides and pro-drugs thereof to modulate angiogenesis and cell migration to treat or prevent a disorder associated with angiogenesis specifically including carcinomas/tumours, inflammation, ocular disorders or wound healing.

Combinations of FKBP-L polypeptides with existing therapeutic agents for use in such diseases are also disclosed in WO 2007141533.

WO 2007141533 does not disclose or teach the use of FKBP-L polypeptides in the treatment of obesity and/or obesity-related disorders.

In obesity, adipose tissue angiogenesis plays a complex role to support tissue growth and promote metabolic disease. However, whilst some teaching in the art has suggested anti-angiogenic therapy may reduce adiposity, others have shown that reduction of angiogenesis leading to reduced blood vessels can enhance adipose tissue perturbations such as hypoxia, inflammation, and apoptosis, eventually leading to systemic insulin resistance, and worsening obesity (Lemoine AY1, Ledoux S, Larger E. Adipose tissue angiogenesis in obesity. Thromb Haemost. 2013 October; 110(4):661-8. doi: 10.1160/TH13-01-0073. Epub 2013 Apr. 18. and Sung, H. K., Doh, K. O., Son, J. E., Park, J. G., Bae, Y., Choi, S., Nelson, S. M., Cowling, R., Nagy, K., Michael, I. P. et al. Adipose vascular endothelial growth factor regulates metabolic homeostasis through angiogenesis. Cell Metab. 2013; 17: 61-72). In particular, although the inhibition of adipose tissue angiogenesis had originally been proposed as a means of treating obesity, this concept has subsequently been challenged by the paradox that energy expenditure might also require angiogenesis. This is particularly true for the development of BAT for protection against obesity (Cao, Y. 'Angiogenesis modulates adipogenesis and obesity.' *J. Clin. Invest.* 117, 2362-2368 (2007) and Xue, Y. et al. 'Hypoxia-independent angiogenesis in adipose tissues during cold acclimation.' *Cell Metab.* 9, 99-109 (2009)).

Obesity and metabolic syndrome is thus a complicated and dynamic process and therapeutic treatments of obesity and metabolic diseases, targeting angiogenesis, remains a disputed issue.

The present invention provides a FKBP-L polypeptide, a biologically active fragment of an FKBP-L polypeptide, a derivative of FKBP-L polypeptide, or a derivative of a biologically active fragment of an FKBP-L polypeptide, or a nucleic acid sequence capable of being expressed in a subject to provide FKBP-L or a biologically active fragment or derivative thereof for use in the treatment of obesity and obesity-related disorders.

It is considered that the FKBP-L polypeptides/peptides, prodrugs, nucleic acids and combinations discussed in WO20071411533 can be utilised in the present invention to treat obesity and/or obesity related disorders.

The present invention also provides methods for treatment of obesity and obesity-related disorders in a human or animal subject or patient by administration of a FKBP-L polypeptide, a biologically active fragment of an FKBP-L polypeptide, a derivative of FKBP-L polypeptide, or a derivative of a biologically active fragment of an FKBP-L polypeptide, or a nucleic acid sequence capable of being expressed in a subject to provide FKBP-L or a biologically active fragment or derivative thereof.

The present invention also provides the use of a FKBP-L polypeptide, a biologically active fragment of an FKBP-L polypeptide, a derivative of FKBP-L polypeptide, or a derivative of a biologically active fragment of an FKBP-L polypeptide, or a nucleic acid sequence capable of being expressed in a subject to provide FKBP-L or a biologically active fragment or derivative thereof for use in the preparation of a medicament for the treatment of obesity and obesity-related disorders.

Further in accordance with the present invention, there is provided a pharmaceutical composition comprising a FKBP-L polypeptide, a biologically active fragment of an FKBP-L polypeptide, a derivative of FKBP-L polypeptide, or a derivative of a biologically active fragment of an FKBP-L polypeptide, or a nucleic acid sequence capable of being expressed in a subject to provide FKBP-L or a biologically active fragment or derivative thereof and at least one pharmaceutical carrier, wherein a FKBP-L polypeptide, a biologically active fragment or a derivative thereof is present in an amount effective for use in the treatment of obesity and obesity-related disorders.

In a further aspect of the invention, there is provided a FKBP-L polypeptide, a biologically active fragment of an FKBP-L polypeptide, a derivative of FKBP-L polypeptide, or a derivative of a biologically active fragment of an FKBP-L polypeptide thereof, or a nucleic acid sequence capable of being expressed in a subject to provide FKBP-L or a biologically active fragment or derivative thereof in combination with at least one pharmacologically active agent (s) that is (are) useful in the treatment of obesity or obesity-related disorders.

In a yet further aspect of the invention, there is provided the use of a FKBP-L polypeptide, a biologically active fragment of an FKBP-L polypeptide, a derivative of FKBP-L polypeptide, or a derivative of a biologically active fragment of an FKBP-L polypeptide thereof, or a nucleic acid sequence encoding FKBP-L as expressed in a subject to provide FKBP-L or a biologically active fragment or derivative as a biomarker for obesity. By determining endogenous expression or activity levels of FKBP-L and determining whether these are considered to be in a 'normal range' or 'reduced', where the expression or activity level is reduced it would be indicative of obesity or obesity related disorders. The inventors have determined lower serum FKBP-L in obese compared to normal individuals and further have correlated FKBP-L with the level of BMI. According to an aspect of the invention, low levels of FLBP-L could be used as a predictive biomarker whereby individuals with obesity or predisposed to obesity could be treated with FKBP-L polypeptides/nucleic acids. Treatment with FKBP-L may cause an enhanced response in obese individuals deficient in FKBP-L In embodiments the expression level or activity of FKBP-L can be determined as a biomarker for obesity. Suitably, the expression level or activity of FKBP-L may be determined by determining SNP(s) of FKBP-L, preferably SNP(s) within the FKBP-L gene of the subject being tested.

An embodiment of the present invention will now be described by way of example only with reference to the accompanying figures in which:

BRIEF DESCRIPTION OF THE DRAWINGS

FIGS. 8A to 8C illustrate amino acid sequences of FKBP-L and derivatives and fragments thereof.

FIGS. 9A to 9E illustrate nucleic acid sequences encoding for FKBP-L and deletion mutants and variants.

FIG. 10 illustrates subcutaneous adipose tissue from Fkbpl$^{+/-}$ mice and demonstrates hypertrophic adipocytes: Images of H&E stained subcutaneous adipose tissue in female mice aged 6-8 weeks. Adipocytes are significantly enlarged (hypertrophic) in mice from Fkbpl$^{+/-}$ mice.

A) Weight change (g) of male C57BL/6N mice during four weeks of HFD feeding with no treatment (control; n=4), or weekly IV pFKBPL (n=5) or IV RALA-pFKBPL (n=5);

B) Weight change (g) of male C57BL/6N mice during four weeks of standard chow feeding with no treatment (control; n=4), or weekly IV pFKBPL (n=5) or IV RALA-pFKBPL (n=4), wherein results are displayed as mean±SEM. Statistical analysis was by two-way ANOVA with Bonferroni post hoc test, where * represents $p<0.05$,  represents $p<0.01$, and * represents $p<0.001$ for control vs IV RALA-pFKBPL, and where + represents $p<0.05$, ++ represents $p<0.01$, and +++ represents $p<0.001$ for control vs IV pFKBPL.

Figure 17:
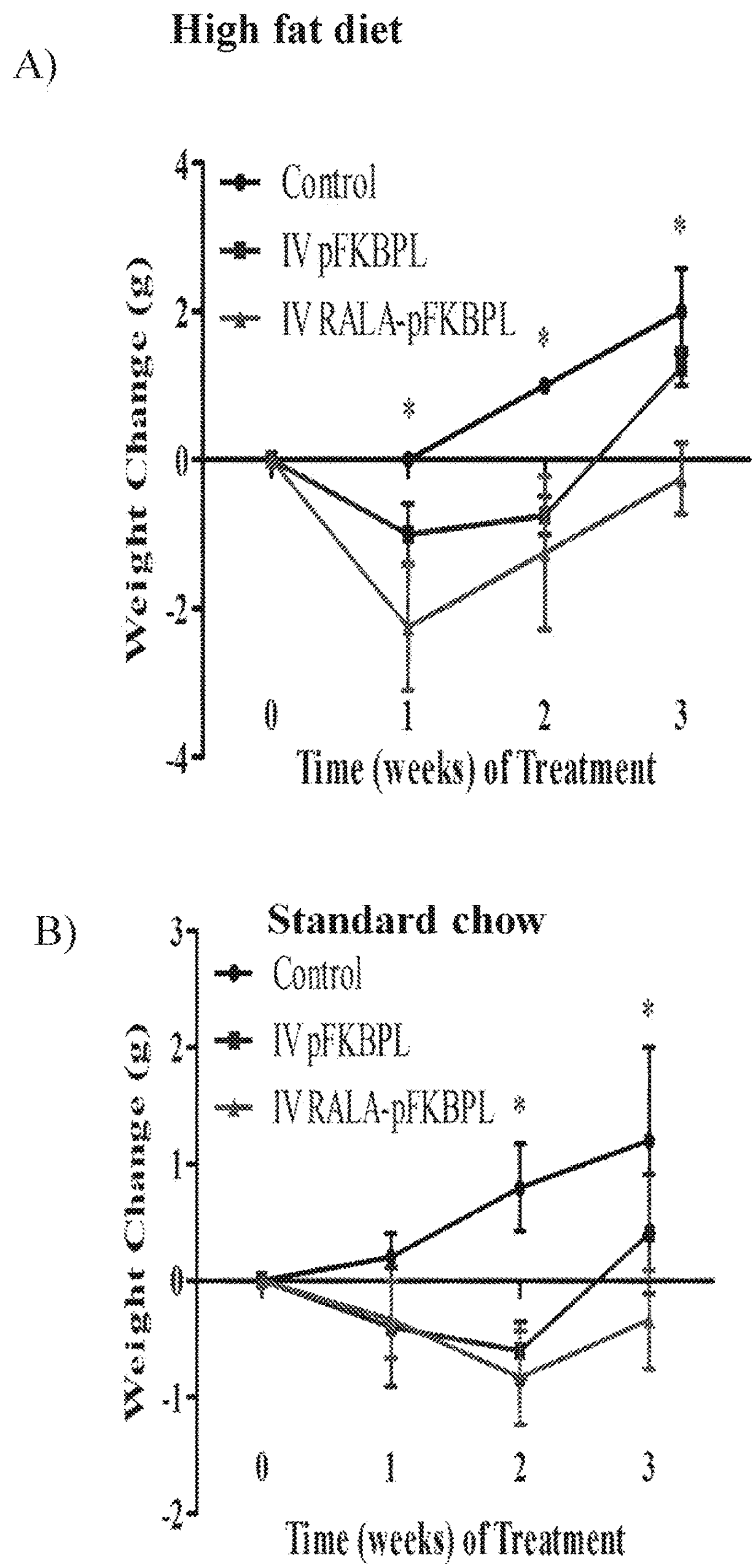

FIG. 17 illustrates that male C57BL/6N mice, age 8 weeks, which had been fed a HFD, or standard chow, for the following 14 weeks could be induced to lose weight when mice were treated via i.v. injection of naked plasmid DNA containing the full length FKBPL gene (pFKBPL) or plasmid DNA containing the full length FKBPL gene delivered using a novel peptide delivery system, RALA (RALA-pFKBPL), when these were delivered once weekly. Control mice received no treatment. A) Weight change (g) of male C57BL/6N mice during three weeks of either no treatment (control; n=3), or weekly IV pFKBPL (n=4) or IV RALA-pFKBPL (n=4); following 14 weeks of HFD feeding;

B) Weight change (g) of male C57BL/6N mice during three weeks of either no treatment (control; n=4), or weekly IV pFKBPL (n=5) or IV RALA-pFKBPL (n=6); following 14 weeks of standard chow feeding.

Results are displayed as mean±SEM. Statistical analysis was by two-way ANOVA with Bonferroni post hoc test, where * represents $p<0.05$,  represents $p<0.01$, and * represents $p<0.001$ for control vs IV RALA-pFKBPL.

Figure 18:
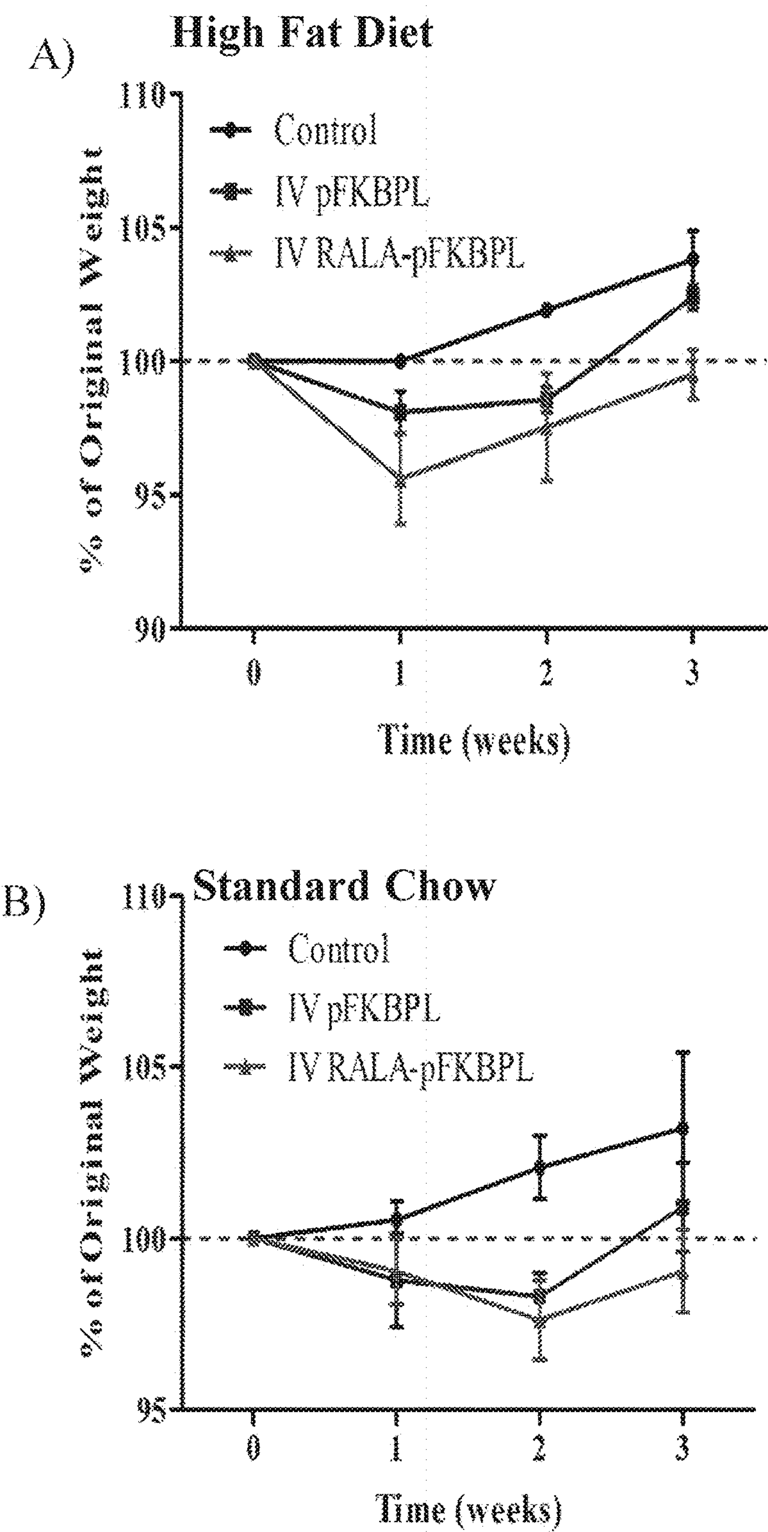

FIG. 18 illustrates the same data as FIG. 17, but is presented as % of original body weight—there is approximately a 5% decrease in body weight with RALA-pFKBPL compared to control mice and the 5% decrease is maintained for the 3 weeks of treatment; this decrease is in line with European Medicines Agency Guidelines for medicinal products used in weight management.

DETAILED DESCRIPTION

The following detailed description and the accompanying drawings to which it refers are intended to describe some, but not necessarily all, examples or embodiments of the invention. The described embodiments are to be considered in all respects only as illustrative and not restrictive.

The contents of this detailed description and the accompanying drawings do not limit the scope of the invention in any way.

Definitions

Abbreviations for amino acid residues are the standard 3-letter and/or 1-letter codes used in the art to refer to one of the 20 common L-amino acids. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10. Additionally, any reference referred to as being "incorporated herein" is to be understood as being incorporated in its entirety.

As used in this specification, the singular forms "a," "an," and "the" include plural referents unless expressly and unequivocally limited to one referent. The term "or" is used interchangeably with the term "and/or" unless the context clearly indicates otherwise. Also, the terms "portion" and "fragment" are used interchangeably to refer to parts of a polypeptide, nucleic acid, or other molecular construct.

As used herein, the term FKBP-L polypeptides and nucleic acids that encode FKBP-L are used in the specification according to its broadest meaning. FKBP-L designates the naturally occurring proteins as described in WO2007141533 which include those having the following sequences:

```
SEQ ID No. 2:
METPPVNTIGEKDTSQPQQEWEKNLRENLDSVIQIRQQPRDPPTETLELE

VSPDPASQILEHTQGAEKLVAELEGDSHKSHGSTSQMPEALQASDLWYCP

DGSFVKKIVIRGHGLDKPKLGSCCRVLALGFPFGSGPPEGWTELTMGVGP

WREETWGELIEKCLESMCQGEEAELQLPGHTGPPVGLTLASFTQGRDSWE

LETSEKEALAREERARGTELFRAGNPEGAARCYGRALRLLLTLPPPGPPE

RTVLHANLAACQLLLGQPQLAAQSCDRVLEREPGHLKALYRRGVAQAALG

NLEKATADLKKVLAIDPKNRAAQEELGINVIQGKNQDAGLAQGLRKMFG

SEQ ID No. 29:
METPPVNTIGEKDTSQPQQEWEKNLRENLDSVIQIRQQPRDPPTETLELE

VSPDPASQILEHTQGAEKLVAELEGDSHKSHGSTSQMPEALQASDLWYCP
```

-continued

```
DGSFVKKIVIRGHGLDKPKLGSCCRVLALGFPFGSGPPEGWTELTMGVGP

WREETWGELIEKCLESMCQGEEAELQLPGHSGPPVRLTLASFTQGRDSWE

LETSEKEALAREERARGTELFRAGNPEGAARCYGRALRLLLTLPPPGPPE

RTVLHANLAACQLLLGQPQLAAQSCDRVLEREPGHLKALYRRGVAQAALG

NLEKATADLKKVLAIDPKNRAAQEELGINVIQGKNQDAGLAQGLRKMFG
```

FKBP-L (SEQ ID NO: 2) can be encoded by the nucleotide sequence:

```
(Accesion number NM_022110)
atggagacgc caccagtcaa tacaattgga gaaaaggaca

cctctcagcc gcaacaagag tgggaaaaga accttcggga

gaaccttgattcagttattc agattaggca gcagccccga

gaccctccta ccgaaacgct tgagctggaagtaagcccag

atccagccag ccaaattcta gagcatactc aaggagctga

aaaactggttgctgaacttg aaggagactc tcataagtct

catggatcaa ccagtcagat gccagaggcccttcaagctt

ctgatctctg gtactgcccc gatgggagct ttgtcaagaa

gatcgtaatccgtggccatg gcttggacaa acccaaacta

ggctcctgct gccgggtact ggctttggggtttcctttcg

gatcagggcc gccagagggc tggacagagc taactatggg

cgtagggccatggagggagg aaacttgggg ggagctcata

gagaaatgct tggagtccat gtgtcaaggtgaggaagcag

agcttcagct gcctgggcac tctggacctc ctgtcaggct

cacactggcatccttcactc aaggccgaga ctcctgggag

ctggagacta gcgagaagga agccctggccagggaagaac

gtgcaagggg cacagaacta tttcgagctg ggaaccctga

aggagctgcccgatgctatg gacgggctct tcggctgctc

ctgactttac ccccacctgg ccctccagaacgaactgtcc

ttcatgccaa tctggctgcc tgtcagttgt tgctagggca

gcctcagttggcagcccaga gctgtgaccg ggtgttggag

cgggagcctg gccatttaaa ggccttataccgaagggggg

ttgcccaggc tgcccttggg aacctggaaa aagcaactgc

tgacctcaagaaggtgctgg cgatagatcc caaaaaccgg

gcagcccagg aggaactggg gaaggtggtcattcagggga

agaaccagga tgcagggctg gctcagggtc tgcgcaagat

gtttggctgattaaaagtta aaccttaaaa gagaaaaaaa

aaaaaaa
```

A FKBP-L variant (SEQ ID NO:29) may be encoded by a nucleic acid sequence comprising:

-continued

```
atggagacgc caccagtcaa tacaattggagaaaaggaca

cctctcagcc gcaacaagag tgggaaaaga accttcggga

gaaccttgattcagttattc agattaggca gcagccccga

gaccctccta ccgaaacgct tgagctggaagtaagcccag

atccagccag ccaaattcta gagcatactc aaggagctga

aaaactggttgctgaacttg aaggagactc tcataagtct

catggatcaa ccagtcagat gccagaggcccttcaagctt

ctgatctctg gtactgcccc gatgggagct ttgtcaagaa

gatcgtaatccgtggccatg gcttggacaa acccaaacta

ggctcctgct gccgggtact ggctttggggtttcctttcg

gatcagggcc gccagagggc tggacagagc taactatggg

cgtagggccatggagggagg aaacttgggg ggagctcata

gagaaatgct tggagtccat gtgtcaaggtgaggaagcag

agcttcagct gcctgggcac actggacctc ctgtcgggct

cacactggcatccttcactc aaggccgaga ctcctgggag

ctggagacta gcgagaagga agccctggccagggaagaac

gtgcaagggg cacagaacta tttcgagctg ggaaccctga

aggagctgcccgatgctatg gacgggctct tcggctgctc

ctgactttac ccccacctgg ccctccagaacgaactgtcc

ttcatgccaa tctggctgcc tgtcagttgt tgctagggca

gcctcagttggcagcccaga gctgtgaccg ggtgttggag

cgggagcctg gccatttaaa ggccttataccgaagggggg

ttgcccaggc tgcccttggg aacctggaaa aagcaactgc

tgacctcaagaaggtgctgg cgatagatcc caaaaaccgg

gcagcccagg aggaactggg gaaggtggtcattcagggga

agaaccagga tgcagggctg gctcagggtc tgcgcaagat

gtttggctgattaaaagtta aaccttaaaa gagaaaaaaa

aaaaaaa
```

Further derivatives and fragments are illustrated in FIG. 8. In embodiments a FKBP-L derivative can be an amino acid sequence having at least 90% identity to SEQ ID NO: 2 and includes sequences that have 91, 91.5, 92, 92.5, 93, 93.5. 94, 94.5, 95, 95.5, 96, 96.5, 97, 97.5, 98, 98.5, 99, 99.5 percent identity to SEQ ID NO: 2.

Nucleic acids that encode FKBP-L or fragments thereof are provided, for example, by SEQ ID Nos: 30-39, or fragments thereof, for example that can encode a polypeptide having an amino acid sequence as set forth in SEQ ID NOs:1 to 29. In embodiments, degenerate sequences wherein the third 'wobble' position of the encoded amino acid codon is altered may be provided such that the degenerate nucleic acid sequences still encode the polypeptides of the invention with the amino acid sequences set forth herein.

As used herein, the term "biologically active fragments or derivative of FKBP-L polypeptide", is used to refer to a polypeptide that displays the same or similar amount and type of activity as the full-length FKBP-L polypeptide. Suitably, such a fragment may comprise or consist of at least 6, suitably 12, more suitably 18 contiguous amino acids of SEQ ID NO: 10 or a nucleic acid that encodes at least 18 contiguous amino acids of SEQ ID: 10. In embodiments, a fragment can be for example up to 200 amino acids of SEQ ID NO: 2 or SEQ ID NO: 29 or a nucleic acid that encodes up to 200 amino acids of SEQ ID NO: 2 or SEQ ID NO: 29. In embodiments an FKBP-L fragment can be any length that retains its anti-obesity activity such that it can be used according to the present invention.

Thus, biologically active fragments or derivatives of FKBP-L polypeptide can comprise the amino acid sequence shown in any one of SEQ ID NOs: 3 to 7, or 11 to 28, or an amino acid sequence at least 90% identical to the amino acid sequence shown in any one of SEQ ID NOs: 1 to 29 as described in WO2007141533, the entire disclosure of which is expressively incorporated herein by reference. As discussed by WO2007141533, truncated mutants, for example Δ48, Δ58, Δ86, Δ151, Δ200 can provide significant FKBP-L activity.

In embodiments biologically active fragments or derivatives of FKBP-L polypeptide can comprise an amino acid sequence that are at least 91%, 91.5%, 92%, 92.5%, 93%, 93.5%, 94%, 94.5%, 95%, 95.5%, 96%, 96.5%, 97%, 97.5%, 98%, 98.5%, 99%, 99.5% identical to SEQ ID No. 2. Suitably derivatives may be provided by incorporation of deliberate amino acid substitutions in the polypeptide on the basis of similarity in polarity, charge, solubility, hydrophobicity or hydrophilicity of the amino acid residues as long as specificity of function (activity) is retained. Further, polypeptides may be modified by the addition of a functional group, for example PEG or the like.

Moreover, derivatives can include analogues of the natural FKBP-L amino acid sequence which are capable of providing similar functional activity. Derivatives can also include multimeric peptides such that FKBP-L polypeptides are provided as multimers through the formation of disulphide bonds between monomers of the FKBP-L polypeptide. Derivatives can also include wherein the polypeptide is linked to a coupling partner such as a label, drug, or carrier or transport molecule. FKBP-L derivatives can also include fusion proteins, for example wherein FKBP-L is linked to an antibody to allow targeting or to facilitate purification as provided for example, in SEQ ID No. 1.

Suitably, derivatives can provide increased half-life or stability against proteolysis through addition of further moieties or by incorporation of an unnatural amino acid or via backbone modifications. Derivatives may also be provided by providing reverse or retro analogues of the FKBP-L polypeptides and/or their synthetic derivatives. Suitably derivatives of FKBP-L can be provided as pro-drugs of the polypeptides wherein following administration, for example, by intravenous, subcutaneous or intramuscular injection or via the intranasal cavity, they can be metabolised by plasma proteases to provide an active form of FKBP-L. Ways of forming pro-drugs would be known to those of skill in the art for example as discussed in WO 2007/141533 at pages 48-53 incorporated herein by reference.

As used herein, biologically active FKBP-L or biologically active fragments or derivatives of FKBP-L may be tested for activity in comparison to full length FKBP-L using in vitro or in vivo assays. Suitable assays to demonstrate anti-obesity effects are provided by the examples provided herein.

As known in the art, "protein", "peptides" and "polypeptide" are chains of amino acids (typically L-amino acids) whose alpha-carbons are linked through peptide bonds formed by condensation reactions between the carboxyl group of the alpha-carbon of one amino acid and the amino group of the alpha-carbon of another amino acid. Typically, as used herein, the term polypeptide and peptide have been used interchangeably. A "nucleic acid" is a polynucleotide such as deoxyribonucleic acid (DNA) or ribonucleic acid (RNA). The term is used to include single and double stranded nucleic acids and RNA and DNA made from nucleotide or nucleoside analogues.

The term "composition", as in pharmaceutical composition, is intended to encompass a product comprising the active ingredient(s), suitably a FKBP-L polypeptide or fragment or derivative thereof or a nucleic acid encoding the same, and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions utilized in the present invention encompass any composition made by admixing an active ingredient and one or more pharmaceutically acceptable carriers.

As used herein, the term "pharmacologically effective amount" (including "therapeutically effective amount") means an amount of a peptide according to the invention that is sufficient to induce a desired therapeutic or biological effect.

As used herein, the term "therapeutically effective amount" means the amount of a peptide of the invention that will elicit a biological or medical response in the mammal that is being treated by a medical doctor or other clinician.

The terms "therapy" and "treatment" may include treatment and/or prophylaxis. As used herein all references to polypeptides according to the invention, including a specific chemical formula or name, are intended to include all pharmaceutically acceptable salts, solvates, hydrates, polymorphs, pro-drugs, metabolites, stereoisomers, and tautomeric isomers thereof.

As used herewith, the disease Type 2 Diabetes, which is non-insulin-dependent diabetes mellitus as diagnosed according to criteria published in the Report of the Expert Committee on the Diagnosis and Classification of Diabetes Mellitus whereby fasting plasma glucose level is greater than or equal to 126 milligrams per deciliter, and latent autoimmune diabetes mellitus of adults (LADA).

The term "metabolic disorders" refers to glucose and lipid regulatory disorders, including insulin resistance and defective secretion of insulin by pancreatic beta cells, and may further include conditions and states such as abdominal obesity, dyslipidemia, hypertension, glucose intolerance or a prothrombotic state, and which may further result in disorders such as hyperlipidemia, obesity, diabetes, insulin resistance, glucose intolerance, hyperglycemia, and hypertension.

The compositions and methods disclosed herein can be used for both medical applications and animal husbandry or veterinary applications.

Typically, the methods are used in humans, but may also be used in other mammals.

The primary applications of the present invention involve human patients, but the present invention may be applied to laboratory, farm, zoo, wildlife, pet, sport or other animals.

As used herein, the term obesity and related disorders refer to disorders and conditions characterized by excess body weight and/or excess food intake, metabolic disorders, in particular involving energy homeostasis and metabolism such as for example diabetes, in particular type 2 diabetes; dyslipidemia; fatty liver; hypercholesterolemia; hypertriglyceridemia; hyperuricacidemia; impaired glucose tolerance; impaired fasting glucose; insulin resistance syndrome;

and metabolic syndrome; food intake such as for example hyperphagia; binge eating; bulimia; and compulsive eating.

As used herein, the terms "identity" or "percent identity", refer to sequence identity between two amino acid sequences or between two nucleic acid sequences. Percent identity can be determined by aligning two sequences and refers to the number of identical residues (amino acid or nucleotide), a position shared by the compared sequences. Sequence alignment and comparison may be conducted using the algorithms standard in the art.

Suitable packages {e.g. Smith and Waterman, 1981, Adv. Appl. Math. 2:482; Needleman and Wunsch, 1970, J. Mol. Biol. 48:443; Pearson and Lipman, 1988, Proc. Natl. Acad. Sci., USA, 85:2444) or computerized versions of these algorithms (Wisconsin Genetics Software Package Release 7.0, Genetics Computer Group, 575 Science Drive, Madison, Wis.) publicly available as BLAST and FASTA. Also, ENTREZ, available through the National Institutes of Health, Bethesda Md., may be used for sequence comparison. When utilizing BLAST and Gapped BLAST programs, the default parameters of the respective programs (e.g., BLASTN; available at the Internet site for the National Center for Biotechnology Information) may be used. In one embodiment, the percent identity of two sequences may be determined using GCG with a gap weight of 1, such that each amino acid gap is weighted as if it were a single amino acid mismatch between the two sequences. Alternatively, the ALIGN program (version 2.0), which is part of the GCG (Accelrys, San Diego, Calif.) sequence alignment software package may be used.

As used herein, the term "conserved residues" refers to amino acids that are the same among a plurality of proteins having the same structure and/or function. A region of conserved residues may be important for protein structure or function. Thus, contiguous conserved residues as identified in a three-dimensional protein may be important for protein structure or function. To find conserved residues, or conserved regions of 3-D structure, a comparison of sequences for the same or similar proteins from different species, or of individuals of the same species, may be made.

As used herein, the term at least 90% identical thereto includes sequences that range from 90 to 99.99% identity to the indicated sequences and includes all ranges in between. Thus, the term at least 90% identical thereto includes sequences that are 91, 91.5, 92, 92.5, 93, 93.5. 94, 94.5, 95, 95.5, 96, 96.5, 97, 97.5, 98, 98.5, 99, 99.5 percent identical to the indicated sequence. The determination of percent identity is determined using the algorithms described herein.

As used herein, a polypeptide or protein "domain" comprises a region along a polypeptide or protein that comprises an independent unit. Domains may be defined in terms of structure, sequence and/or biological activity. In one embodiment, a polypeptide domain may comprise a region of a protein that folds in a manner that is substantially independent from the rest of the protein. Domains may be identified using domain databases such as, but not limited to PFAM, PRODOM, PROSITE, BLOCKS, PRINTS, SBASE, ISREC PROFILES, SAMRT, and PROCLASS.

The inventors have determined that a FKBP-L polypeptide, or a biologically active fragment or a derivative of FKBP-L or a derivative of a fragment of FKBP-L or a nucleic acid encoding FKBP-L thereof, can mediate regulation of Sirtuin 1, a family of NAD+-dependent deacetylase. Sirtuin 1 is considered to be significant in metabolic diseases and disorders. The inventors have also demonstrated that treatment with FKBP-L can reduce NFkB and IL-1β.

Thus, in certain embodiments the FKBP-L polypeptides of the present invention can be used to treat metabolic disorders. In particular it is considered that the FKBP-L polypeptides of the invention or expression of nucleic acids that encode FKBP-L upon administration to an animal including man, will reduce body weight and/or body weight gain in that animal, and/or improve obesity-related disease.

Thus, in one embodiment, the present invention comprises an isolated FKBP-L encoding nucleic acid or FKBP-L polypeptide, or a biologically active fragment or derivative thereof, for use in the treatment of obesity and obesity-related disorders.

The FKBP-L encoding nucleic acids and polypeptides of the present invention are particularly useful for treatment of obesity disorders and/or conditions characterized by excess body weight, including obesity and overweight (by promotion of weight loss, maintenance of weight loss, and/or prevention of weight gain, including medication-induced weight gain or weight gain subsequent to cessation of smoking), and diseases, disorders and/or conditions associated with obesity and/or overweight, such as insulin resistance; impaired glucose tolerance; type 2 diabetes; metabolic syndrome; dyslipidemia (including hyperlipidemia); hypertension; heart disorders (e.g. coronary heart disease, myocardial infarction); cardiovascular disorders; nonalcoholic fatty liver disease (including non-alcoholic steatohepatitis); joint disorders (including secondary osteoarthritis); gastroesophageal reflux; sleep apnea; atherosclerosis; stroke; macro and micro vascular diseases; steatosis (e.g. in the liver); gall stones; and gallbladder disorders.

The FKBP-L encoding nucleic acids and polypeptides of the invention are considered to be useful for treatment of obesity and type 2 diabetes, more specifically obesity.

It will be understood that there are medically accepted definitions of obesity and overweight. Subjects who are candidates for treatment by the present invention may be identified by, for example, measuring body mass index (BMI), which is calculated by dividing weight in kilograms by height in meters squared, and comparing the result with the definitions. The recommended classifications for BMI in humans, adopted by the Expert Panel on the Identification, Evaluation and Treatment of Overweight and Obesity in Adults, and endorsed by leading organizations of health professionals, are as follows: underweight <18.5 kg/m2, normal weight 18.5-24.9 kg/m2, overweight 25-29.9 kg/m2, obesity (class 1) 30-34.9 kg/m2, obesity (class 2) 35-39.9 kg/m2, extreme obesity (class 3) is 40 kg/m2 (Practical Guide to the Identification, Evaluation, and Treatment of Overweight and Obesity in Adults, The North American Association for the Study of Obesity (NAASO) and the National Heart, Lung and Blood Institute (NHLBI) 2000). Modifications of this classification may be used for specific ethnic groups and for children.

Another alternative for assessing overweight and obesity is by measuring waist circumference. There are several proposed classifications and differences in the cutoffs based on ethnic group. For instance, according to the classification from the International Diabetes Federation, men having waist circumferences above 94 cm (cut off for europids) and women having waist circumferences above 80 cm (cut off for europids) are at higher risk of diabetes, dyslipidemia, hypertension and cardiovascular diseases because of excess abdominal fat. Another classification is based on the recommendation from the Adult Treatment Panel III where the recommended cut-offs are 102 cm for men and 88 cm for women. It will however be appreciated by persons skilled in the art that obesity is inherently difficult to classify, and that the cut-off point for the definition of obesity is necessarily arbitrary, in part because body fatness is a continuum.

However, in general terms treatment according to the present invention desirably prevents or alleviates obesity to an extent whereby there is no longer a significant health risk to the patient.

In one embodiment, the FKBP-L polypeptides for use according to the invention comprises the amino acids sequence shown in SEQ ID NO: 1, SEQ ID NO: 2 or SEQ ID NO: 29.

In a further embodiment, biologically active fragments or derivative of FKBP-L polypeptide comprises the amino acid sequence shown in any one of SEQ ID NOs: 3 to 7, or 11 to 28.

In one embodiment the biologically active fragments or derivative of FKBP-L polypeptide can be

```
ALM201 (23 mer) (SEQ ID NO: 40):
NH2-IRQQPRDPPTETLELEVSPDPAS-OH
or

AD-01 (24 mer) (SEQ ID NO: 10):
NH2-QIRQQPRDPPTETLELEVSPDPAS-OH
```

In embodiments biologically active fragments of FKBP-L may be provided by determining an effective portion of n-terminal amino acid sequence of naturally occurring FKBP-L. Suitable embodiments are provided in FIG. 8.

The peptide may comprise or consist of a sequence that comprises at least 18 continuous amino acids of SEQ ID No. 2 or 29. Alternatively, a nucleic acid may be provided which can encode a polypeptide fragment as described herein. In embodiments a nucleic acid encoding a fragment of FKBP-L comprising or consisting of at least 18 continuous amino acids of SEQ ID No. 2 or 29, can include degenerate nucleic acid molecules comprising a degenerate variation on the third position of the amino acid code such that the same amino acid is encoded to generate sequence.

In embodiments a peptide mimetic of a polypeptide sequence of the invention can be provided which has functional activity. Suitably, the FKBP-L polypeptide can be provided as a cyclic peptide or a peptide containing a D or unnatural amino acids, the peptide may be linked to antibodies, carbohydrates, oligosaccharides, polysaccharides, glycolipids, nucleosides or nucleotides or part thereof or small molecules. Further, the FKBP-L polypeptides of the invention can be chemically modified and include isomeric or racemic forms.

Targeting systems such as antibody or cell specific ligands can be used to target FKBP-L to specific cells. For example, targeting systems can be covalently linked to a peptide sequence or to a drug delivery vehicle including the polypeptide sequence for example liposomes, microsomes, microparticles, microcapsules, nanopolymers or the like.

Nucleic acids of the present invention may be provided via an expression system. Nucleic acid constructs that encode FKBP-L or fragments or derivatives thereof may comprise DNA or RNA and may be produced recombinantly, synthetically, or by any other techniques as known in the art. Suitably a nucleic acid of the invention may be provided in a vector, for example an expression vector. Suitably, the nucleic acid of the invention may be operably linked to a control sequence such that the control sequence can provide expression of the nucleic acid in a host. Suitable a control sequence may include a mammalian promoter sequence, for example a constitutive mammalian promoter. Suitably a promoter may not be constitutive, but inducible, for example by particular developmental or other factors, for example metal ions, external drugs, hormones, enzyme substrates or the like. Suitably, viral promoters, for example CMV promoter, SV40 promoter, or LTR, HBV, HCV, HSV, HPV, EBV, HTLV, HIV promoters could be used. Enhancer and other regulatory elements may also be provided in a vector. A vector that may be utilised may include viral vectors, yeast vectors, phage, chromosomes, artificial chromosomes, plasmids, cosmid DNA, liposomes, polyplexes, or cells such as stem cells, mesenchymal cells or the like. Suitably viral vectors may include adenovirus, vaccina virus, lentivirus, retrovirus or baclovirus.

Suitably a vector provides a nucleic acid into a host cells to allow expression of the FKBP-L. Suitably, the host cell may provide for post translational modification of the expressed FKBP-L, for example glycosylation, disulphide bond formation, post translational modification and the like. Details of known techniques for the preparation of nucleic acids may be obtained from, for example Current Protocols in Molecular Biology, $2^{nd}$ ed., Ausubel et al. eds., John Wiley & Sons, 1992 and, Molecular Cloning: a Laboratory Manual: $3^{rd}$ edition Sambrook et al., Cold Spring Harbour Laboratory Press, 2000. Suitably the methods as discussed at pages 58 to 67 of WO2007/141533 could be utilised to provide nucleic acids encoding FKBP-L.

In embodiments RALA as discussed by WO 2014/087023 and 30mer amphipathic peptides can be used to deliver the FKBP-L gene/nucleic acid encoding FKBP-L. Suitably RALA as discussed by WO 2014/087023 and 30mer amphipathic peptides can be used to deliver the FKBP-L gene/nucleic acid encoding FKBP-L via IV injection for systemic delivery.

RALA allows the delivery of FKBP-L systemically and/or to targeted cells for example to cells associated to obesity related disorders.

Methods of Making Polypeptides

A. Solid-State Peptide Synthesis

Polypeptides according to the present invention can be synthesized by standard solid-state peptide synthesis methods, such as those described in M. Bodanszky, "Principles of Peptide Synthesis" (Springer-Verlag, Berlin, 2d ed., 1993). This involves synthesis on an insoluble polymer such as a styrene-divinylbenzene copolymer that is derivatized. The sequence of reactions used is standard.

B. Genetic Engineering

Polypeptides/peptides according to the present invention can be prepared by genetic engineering. In general, a method of producing a substantially purified peptide according to the present invention having a physiological activity comprises the steps of: (1) culturing a host cell transfected with a vector comprising DNA encoding the peptide operably linked to at least one control element that influences the expression of the DNA; and (2) isolating the peptide produced by the host cell to produce the substantially purified peptide. Expression methods are described in, e.g., D. V. Goeddel, "Gene Expression Technology" (Academic Press, San Diego, 1991). In general, such methods are well known in the art.

Once expressed, the polypeptides/peptides of the present invention can be isolated by standard protein isolation techniques including ion-exchange chromatography on resins such as diethylaminoethylcellulose or carboxymethylcellulose, chromatography on size exclusion media (gel filtration), isoelectric focusing, chromatofocusing, and other standard methods, such as those described in R. K. Scopes, "Protein Purification: Principles and Practice" (3d Ed., Springer-Verlag, New York, 1994).

Polypeptides/peptides of the present invention may be in the form of any pharmaceutically acceptable salt.

The term "pharmaceutically acceptable salts" refers to salts prepared from pharmaceutically acceptable non-toxic bases or acids including inorganic or organic bases and inorganic or organic acids (see "Handbook of Pharmaceutical Salts: Properties, Selection and Use", P. H. Stahl, P. G. Wermuth, IUPAC, Wiley-VCH, 2002). Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the peptide of the present invention is basic, acid addition salts may be prepared from pharmaceutically acceptable non-toxic acids, including inorganic and organic acids. Such acids include acetic, benzenesulfonic, benzoic, camphorsulfonic, carboxylic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Acid addition salts of polypeptides of the present invention are prepared in a suitable solvent for the peptide and an excess of an acid, such as hydrochloric, hydrobromic, sulfuric, phosphoric, acetic, trifluoroacetic (TFA), citric, tartaric, maleic, succinic or methanesulfonic acid. Acetate, ammonium acetate and TFA acid salt forms may be especially useful.

Pharmaceutical Compositions.

The invention provides a pharmaceutical composition that includes one or more polypeptides of the present invention and a pharmaceutically acceptable carrier. When formulated with a pharmaceutically acceptable carrier, the compound of the invention may be present in the pharmaceutical composition in a concentration from 0.0001 to 99.5%, such as from 0.001 to 95%, by weight of the total composition. The choice of carrier is within the knowledge of a person skilled in the art and depends on, for instance, the mode of administration, the dosage form, and the physical properties of the active compound, such as solubility and stability. The term "carrier" as used herein relates to a therapeutically inactive ingredient. The dosage form may be a solid, semi-solid, liquid or self-gelling system. The formulation may be an immediate and/or modified release, including delayed-, sustained-, pulsed-, controlled-, targeted and programmed release formulation. The carrier may be a liquid formulation, and is preferably a buffered, isotonic, aqueous solution. Pharmaceutically acceptable carriers also include excipients, such as diluents, carriers and the like, and additives, such as stabilizing agents, preservatives, solubilizing agents, buffers and the like, as hereafter described. Formulation excipients may include polyvinylpyrrolidone, gelatin, hydroxy propyl cellulose (HPC), acacia, polyethylene glycol, mannitol, sodium chloride and sodium citrate. For injection or other liquid administration formulations, water containing at least one or more buffering constituents is preferred, and stabilizing agents, preservatives and solubilizing agents may also be employed. A preferred embodiment includes a liquid formulation containing 1, 10, or 25 mg/mL peptide in a solution composed of 10 mM sodium phosphate, 0.8% (w/v) NaCl, 0.05% (w/v) polysorbate 20, in water for injection (pH 6).

For solid administration formulations, any of a variety of thickening, filler, bulking and carrier additives may be employed, such as starches, sugars, cellulose derivatives, fatty acids and the like. For topical administration formulations, any of a variety of creams, ointments, gels, lotions and the like may be employed.

For most pharmaceutical formulations, non-active ingredients will constitute the greater part, by weight or volume, of the preparation. For pharmaceutical formulations, it is also contemplated that any of a variety of measured-release, slow-release or sustained-release formulations and additives may be employed, so that the dosage may be formulated so as to provide delivery of a peptide of the present invention over a period of time. In general, the actual quantity of polypeptides of the present invention administered to a patient will vary between fairly wide ranges depending on the mode of administration, the formulation used, and the response desired. In practical use, the peptides of the invention can be combined as the active ingredient in an admixture with a pharmaceutical carrier according to conventional pharmaceutical compounding techniques. The carrier may take a wide variety of forms depending on the form of preparation desired for administration, for example, oral, parenteral (including intravenous), urethral, vaginal, nasal, buccal, sublingual, or the like.

In preparing the compositions for an oral dosage form, any of the usual pharmaceutical media may be employed, such as, for example, water, glycols, oils, alcohols, flavoring agents, preservatives, coloring agents and the like in the case of oral liquid preparations such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets. Because of their ease of administration, tablets and capsules represent an advantageous oral dosage unit form. If desired, tablets may be coated by standard aqueous or nonaqueous techniques. The amount of active peptide in such therapeutically useful compositions is such that an effective dosage will be obtained. In another dosage unit form, sublingual constructs may be employed, such as sheets, wafers, tablets or the like.

The tablets, pills, capsules, and the like may also contain a binder such as povidone, gum tragacanth, acacia, corn starch or gelatin; diluents; fillers such as microcrystalline cellulose; excipients such as dicalcium phosphate; a disintegrating agent such as corn starch, potato starch or alginic acid; preservatives; colorants; a lubricant such as magnesium stearate; and a sweetening agent such as sucrose, lactose or saccharin. When a dosage unit form is a capsule, it may contain, in addition to materials of the above type, a liquid carrier such as fatty oil. Various other materials may be utilized as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

If formulated for oral delivery, the peptide is preferably formulated and made such that it is encased in an enteric protectant, more preferably such that it is not released until the tablet or capsule has transited the stomach, and optionally has further transited a portion of the small intestine. In the context of this application it will be understood that the term enteric coating or material refers to a coating or material that will pass through the stomach essentially intact but will disintegrate after passing through the stomach to release the active drug substance. Materials that may be used includes cellulose acetate phthalate, hydroxypropylmethylethylcellulose succinate, hydroxypropylmethylcellulose phthalate, polyvinyl acetate phthalate, and methacrylic acid methyl methacrylate copolymer. The enteric coating employed promotes dissolution of the dosage form primarily at a site outside the stomach, and may be selected such that the enteric coating dissolves at a pH of approximately at least 5.5, more preferable at a pH of from about 6.0 to about 8.0.

Any of a variety of permeation enhancers may be employed, to increase uptake in the intestines upon dissolution of the enteric coating. In one aspect, permeation enhancers increase either paracellular or transcellular transport systems.

Representative, non-limiting examples of such permeation enhancers include calcium chelators, bile salts (such as sodium cholate), and fatty acids. In some embodiments, peptides or polypeptides that act as substrates for intestinal proteases are further added. Peptides may also be administered parenteral. Solutions or suspensions of these active peptides may for instance be prepared in water mixed with for instance hydroxy-propylcellulose. Dispersions can also be prepared in glycerol, liquid polyethylene glycols and mixtures thereof in oils. These preparations may optionally contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that it may be administered by syringe. The form must be stable under the conditions of manufacture and storage and must be preserved against the contaminating action of microorganisms such as bacteria and fungi. The carrier can be a solvent or dispersion medium containing, for example, water, ethanol, a polyol, for example glycerol, propylene glycol or liquid polyethylene glycol, suitable mixtures thereof, and vegetable oils.

Polypeptides or nucleic acids encoding the same of the present invention may be therapeutically applied by means of nasal administration. By “nasal administration” is meant any form of intranasal administration of any of the polypeptides of the present invention. The polypeptides may be in an aqueous solution, such as a solution including saline, citrate or other common excipients or preservatives. The polypeptides may also be in a dry or powder formulation. Suitably the polypeptides for nasal administration may be cyclic peptides.

If in an aqueous solution, the polypeptides may be appropriately buffered by means of saline, acetate, phosphate, citrate, acetate or other buffering agents, which may be at any physiologically acceptable pH, such as from about pH 4 to about pH 7. A combination of buffering agents may also be employed, such as phosphate buffered saline, a saline and acetate buffer, and the like. In the case of saline, a 0.9% saline solution may be employed. In the case of acetate, phosphate, citrate, and the like, a 50 mM solution may be employed. In addition to buffering agents, a suitable preservative may be employed, to prevent or limit bacteria and other microbial growth. One such preservative that may be employed is 0.05% benzalkonium chloride.

The polypeptides or nucleic acids encoding the same of the present invention may be therapeutically administered by means of an injection of a sustained release formulation. In general, any of a number of injectable and bioerodible polymers may be employed in a sustained release injectable formulation. Alternatively other sustained release formulations may be employed, including formulations permitting subcutaneous injection, which other formulations may include one or more of nano/microspheres, liposomes, emulsions (such as water-in-oil emulsions), gels, insoluble salts or suspensions in oil. The formulation may be such that an injection is required on a daily, weekly, monthly or other periodic basis, depending on the concentration and amount of peptide, the sustained release rate of the materials employed, and other factors known to those of skill in the art.

Routes of Administration.

If a composition including one or more polypeptides of the present invention or a nucleic acid encoding the same is administered by injection, the injection may be intravenous, subcutaneous, intramuscular, intraperitoneal or other means known in the art. In general, any route of administration by which the peptides of invention are introduced across an epidermal layer of cells may be employed. Administration means may thus include administration through mucous membranes, buccal administration, oral administration, dermal administration, inhalation administration, nasal administration, urethral administration, vaginal administration, topical administration to a site to be treated and the like.

Therapeutically Effective Amount.

In general, the actual quantity of polypeptide/peptide of the present invention or nucleic acid to be administered to a patient will vary between fairly wide ranges depending upon the mode of administration, the patient (including weight, sex, health condition and diet), the formulation used, and the response desired. The dosage for treatment is administration, by any of the foregoing means or any other means known in the art, of an amount sufficient to bring about the desired therapeutic effect. The polypeptides/peptides of the present invention are highly active. For example, the polypeptide/peptide can be administered (as a single dose or in divided daily doses) at about 0.001, 0.01, 0.5, 1, 5, 50, 100, 500, 1000, 5000, 10000, or 25000 ug/kg body weight, depending on the specific polypeptide/peptide selected, the desired therapeutic response, the route of administration, the formulation and other factors known to those of skill in the art.

The invention is further intended to include prodrugs of the present polypeptides/peptides, which on administration undergo chemical conversion by metabolic processes before becoming active pharmacological peptides. In general, such prodrugs will be functional derivatives of the present peptides, which are readily convertible in vivo. Prodrugs are any covalently bonded compounds, which release the active parent peptide drug in vivo. Conventional procedures for the selection and preparation of suitable prodrug derivatives are described, for example, in “Design of Prodrugs”, ed. H. Bundgaard, Elsevier, 1985.

Certain modifications of peptides of the present invention may be made in order to enhance the half-life of the peptide (see G. Pasuta and F. M. Veronese (2007) “Polymer-drug conjugation, recent achievements and general strategies” Progress in Polymer Science 32 (8-9): 933-961).

Combination Therapy

The polypeptides and nucleic acids encoding polypeptides compositions and methods of the present invention may be used for treatment of any of the foregoing diseases, indications, conditions or syndromes, or any disease, indication, condition or syndrome by administration in combination with one or more other pharmaceutically active compounds. Such combination administration may be by means of a single dosage form which includes both a peptide of the present invention and one more other pharmaceutically active compound, such single dosage form including a tablet, capsule, spray, inhalation powder, injectable liquid or the like. Alternatively, combination administration may be by means of administration of two different dosage forms, with one dosage form containing a peptide of the present invention, and the other dosage form including another pharmaceutically active compound. In this instance, the dosage forms may be the same or different. Without meaning to limit combination therapies, the following exemplifies certain combination therapies which may be employed.

According to an additional further aspect of the present invention there is provided a combination treatment comprising the administration of a pharmacologically effective amount of a compound according to the invention, optionally together with a pharmaceutically acceptable carrier, with the simultaneous, sequential or separate administration of at least one pharmacologically active agent (s) that is (are) useful in the treatment of various weight and feeding-related disorders, such as obesity and/or overweight.

Thus, polypeptides and nucleic acids encoding polypeptides of the invention may be combined with one or more other pharmacologically active agent (s) that is (are) useful in the treatment of various weight and feeding-related disorders, such as obesity and/or overweight, in particular other anti-obesity drugs that affect energy expenditure, glycolysis, gluconeogenesis, glycogenolysis, lipolysis, lipogenesis, fat absorption, fat storage, fat excretion, hunger and/or satiety and/or craving mechanisms, appetite/motivation, food intake, or gastrointestinal motility. Drugs that reduce energy intake include, in part, various pharmacological agents, referred to as anorectic drugs, which are used as adjuncts to behavioural therapy in weight reduction programs.

Generally, a total dosage of the below-described obesity control agents or medications, when used in combination with one or more peptides or nucleic acids of the present invention can range from 0.1 to 3,000 mg/day, preferably from about 1 to 1,000 mg/day and more preferably from about 1 to 200 mg/day in single or 2-4 divided doses. The exact dose, however, is determined by the attending clinician and is dependent on such factors as the potency of the compound administered, the age, weight, condition and response of the patient.

Polypeptides and nucleic acids of the invention may be combined with one or more other pharmacologically active agent (s) that is (are) useful in the treatment of diabetes, such as other anti-diabetic drugs.

Polypeptides and nucleic acids of the invention may in addition or alternatively further be combined with one or more other pharmacologically active agent(s) that is (are) useful in the treatment of diseases, disorders and/or conditions associated with obesity and/or overweight, such as insulin resistance; impaired glucose tolerance; type 2 diabetes; metabolic syndrome; dyslipidemia (including hyperlipidemia); hypertension; heart disorders (e.g. coronary heart disease, myocardial infarction); cardiovascular disorders; non-alcoholic fatty liver disease (including non-alcoholic steatohepatitis); joint disorders (including secondary osteoarthritis); gastroesophageal reflux; sleep apnea; atherosclerosis; stroke; macro and micro vascular diseases; steatosis (e.g. in the liver); gall stones; and gallbladder disorders.

In embodiments, polypeptides and nucleic acids of the invention may be provided for cosmetic purposes to decrease aesthetic dissatisfaction or another cosmetic condition. A cosmetic condition refers to a condition due to normal processes in the body, for example aging, pregnancy, puberty. For example polypeptides and nucleic acids of the invention may be provided to reduce deposits of fat on the face, periorbital area, cheeks, chin, neck, chest, breast, abdomen, buttocks, hips, thighs, legs or arms or combinations thereof. In embodiments, this treatment may improve reduced self-esteem and psychosocial distress.

According to a further aspect of the invention there is provided a combination treatment comprising the administration of a pharmacologically effective amount of a peptide and nucleic acids according to the invention, or a pharmaceutically acceptable salt thereof, optionally together with a pharmaceutically acceptable diluent or carrier, with the simultaneous, sequential or separate administration of one or more of the following agents selected from: (1) insulin and insulin analogues; (2) insulin secretagogues, including sulphonylureas (e.g. glipizide) and prandial glucose regulators (sometimes called "short-acting secretagogues"), such as meglitinides (e.g. repaglinide and nateglinide); (3) agents that improve incretin action, for example dipeptidyl peptidase IV (DPP-4) inhibitors (e.g. vildagliptin, saxagliptin, and sitagliptin), and glucagon-like peptide-1 (GLP-1) agonists (e.g. exenatide); (4) insulin sensitising agents including peroxisome proliferator activated receptor gamma (PPARy) agonists, such as thiazolidinediones (e.g. pioglitazone and rosiglitazone), and agents with any combination of PPAR alpha, gamma and delta activity; (5) agents that modulate hepatic glucose balance, for example biguanides (e.g. metformin), fructose 1,6-bisphosphatase inhibitors, glycogen phosphorylase inhibitors, glycogen synthase kinase inhibitors, and glucokinase activators; (6) agents designed to reduce/slow the absorption of glucose from the intestine, such as alpha-glucosidase inhibitors (e.g. miglitol and acarbose); and (7) agents which antagonise the actions of or reduce secretion of glucagon, such as amylin analogues (e.g. pramlintide); (8) agents that prevent the reabsorption of glucose by the kidney, such as sodium-dependent glucose transporter 2 (SGLT-2) inhibitors (e.g. dapagliflozin); (9) agents designed to treat the complications of prolonged hyperglycaemia, such as aldose reductase inhibitors (e.g. epalrestat and ranirestat); and agents used to treat complications related to micro-angiopathies; (10) anti-dyslipidemia agents, such as HMG-CoA reductase inhibitors (statins, e.g. rosuvastatin) and other cholesterol-lowering agents; PPARa agonists (fibrates, e.g. gemfibrozil and fenofibrate); bile acid sequestrants (e.g. cholestyramine); (11) cholesterol absorption inhibitors (e.g. plant sterols (i.e. phytosterols), synthetic inhibitors); cholesteryl ester transfer protein (CETP) inhibitors; inhibitors of the ileal bile acid transport system (I BAT inhibitors); bile acid binding resins; nicotinic acid (niacin) and analogues thereof; anti-oxidants, such as probucol; and omega-3 fatty acids; (12) antihypertensive agents, including adrenergic receptor antagonists, such as beta blockers (e.g. atenolol), alpha blockers (e.g. doxazosin), and mixed alpha/beta blockers (e.g. labetalol); adrenergic receptor agonists, including alpha-2 agonists (e.g. clonidine); angiotensin converting enzyme (ACE) inhibitors (e.g. lisinopril), calcium channel blockers, such as dihydropyridines (e.g. nifedipine), phenylalkylamines (e.g. verapamil), and benzothiazepines (e.g. diltiazem); angiotensin 11 receptor antagonists (e.g.

candesartan); aldosterone receptor antagonists (e.g. eplerenone); centrally acting adrenergic drugs, such as central alpha agonists (e.g. clonidine); and diuretic agents (e.g. furosemide); (13) haemostasis modulators, including antithrombotics, such as activators of fibrinolysis; thrombin antagonists; factor Vila inhibitors; anticoagulants, such as vitamin K antagonists (e.g. warfarin), heparin and low molecular weight analogues thereof, factor Xa inhibitors, and direct thrombin inhibitors (e.g. argatroban); antiplatelet agents, such as cyclooxygenase inhibitors (e.g. aspirin), adenosine diphosphate (ADP) receptor inhibitors (e.g. clopidogrel), phosphodiesterase inhibitors (e.g. cilostazol), glycoprotein I IB/I I A inhibitors (e.g. tirofiban), and adenosine reuptake inhibitors (e.g. dipyridamole); (14) anti-obesity agents, such as appetite suppressant (e.g. ephedrine), including noradrenergic agents (e.g. phentermine) and serotonergic agents (e.g. sibutramine), pancreatic lipase inhibitors (e.g. orlistat), microsomal transfer protein (MTP) modulators, diacyl glycerolacyltransferase (DGAT) inhibitors, and cannabinoid (CB1) receptor antagonists (e.g. rimonabant); (15) feeding behavior modifying agents, such as orexin receptor modulators and melanin-concentrating hormone (MCH) modulators; (16) glucagon like peptide-1 (GLP-1) receptor modulators; (17) neuropeptideY (NPY)/NPY receptor modulators; (18) pyruvate dehydrogenase kinase (PDK) modulators; (19) serotonin receptor modulators; (20) leptin/leptin receptor modulators; (21) ghrelin/ghrelin receptor modulators; or (22) monoamine transmission-modulating agents, such as selective serotonin reuptake inhibitors (SSRI) (e.g. fluoxetine), noradrenaline reuptake inhibitors (NARI), noradrenaline-serotonin reuptake inhibitors (SNRI), triple monoamine reuptake blockers (e.g. tesofensine), and monoamine oxidase inhibitors (MAOI) (e.g. toloxatone and amiflamine), or a pharmaceutically acceptable salt, solvate, solvate of such a salt or a prodrug thereof, optionally together with a pharmaceutically acceptable carrier to a mammal, such as man, in need of such therapeutic treatment.

According to an additional further aspect of the present invention there is provided a combination treatment comprising the administration of a pharmacologically effective amount of a compound according to the invention, or a pharmaceutically acceptable salt thereof, optionally together with a pharmaceutically acceptable carrier, with the simultaneous, sequential or separate administration of very low calorie diets (VLCD) or low-calorie diets (LCD).

According to a further aspect of the present invention there is provided a kit comprising FKBP-L polypeptide, a biologically active fragment of an FKBP-L polypeptide, a derivative of FKBP-L polypeptide, or a derivative of a biologically active fragment of an FKBP-L polypeptide thereof, or a nucleic acid sequence encoding FKBP-L and instructions for use of the same to reduce obesity or obesity related diseases or for cosmetic purposes. Optionally, the kit can comprise one or more of the following agents selected from: (1) insulin and insulin analogues; (2) insulin secretagogues, including sulphonylureas (e.g. glipizide) and prandial glucose regulators (sometimes called "short-acting secretagogues"), such as meglitinides (e.g. repaglinide and nateglinide); (3) agents that improve incretin action, for example dipeptidyl peptidase IV (DPP-4) inhibitors (e.g. vildagliptin, saxagliptin, and sitagliptin), and glucagon-like peptide-1 (GLP-1) agonists (e.g. exenatide); (4) insulin sensitising agents including peroxisome proliferator activated receptor gamma (PPARy) agonists, such as thiazolidinediones (e.g. pioglitazone and rosiglitazone), and agents with any combination of PPAR alpha, gamma and delta activity; (5) agents that modulate hepatic glucose balance, for example biguanides (e.g. metformin), fructose 1,6-bisphosphatase inhibitors, glycogen phosphorylase inhibitors, glycogen synthase kinase inhibitors, and glucokinase activators; (6) agents designed to reduce/slow the absorption of glucose from the intestine, such as alpha-glucosidase inhibitors (e.g. miglitol and acarbose); and (7) agents which antagonise the actions of or reduce secretion of glucagon, such as amylin analogues (e.g. pramlintide); (8) agents that prevent the reabsorption of glucose by the kidney, such as sodium-dependent glucose transporter 2 (SGLT-2) inhibitors (e.g. dapagliflozin); (9) agents designed to treat the complications of prolonged hyperglycaemia, such as aldose reductase inhibitors (e.g. epalrestat and ranirestat); and agents used to treat complications related to micro-angiopathies; (10) anti-dyslipidemia agents, such as HMG-CoA reductase inhibitors (statins, e.g. rosuvastatin) and other cholesterol-lowering agents; PPARa agonists (fibrates, e.g. gemfibrozil and fenofibrate); bile acid sequestrants (e.g. cholestyramine); (11) cholesterol absorption inhibitors (e.g. plant sterols (i.e. phytosterols), synthetic inhibitors); cholesteryl ester transfer protein (CETP) inhibitors; inhibitors of the ileal bile acid transport system (I BAT inhibitors); bile acid binding resins; nicotinic acid (niacin) and analogues thereof; anti-oxidants, such as probucol; and omega-3 fatty acids; (12) antihypertensive agents, including adrenergic receptor antagonists, such as beta blockers (e.g. atenolol), alpha blockers (e.g. doxazosin), and mixed alpha/beta blockers (e.g. labetalol); adrenergic receptor agonists, including alpha-2 agonists (e.g. clonidine); angiotensin converting enzyme (ACE) inhibitors (e.g. lisinopril), calcium channel blockers, such as dihydropyridines (e.g. nifedipine), phenylalkylamines (e.g. verapamil), and benzothiazepines (e.g. diltiazem); angiotensin II receptor antagonists (e.g. candesartan); aldosterone receptor antagonists (e.g. eplerenone); centrally acting adrenergic drugs, such as central alpha agonists (e.g. clonidine); and diuretic agents (e.g. furosemide); (13) haemostasis modulators, including antithrombotics, such as activators of fibrinolysis; thrombin antagonists; factor Vila inhibitors; anticoagulants, such as vitamin K antagonists (e.g. warfarin), heparin and low molecular weight analogues thereof, factor Xa inhibitors, and direct thrombin inhibitors (e.g. argatroban); antiplatelet agents, such as cyclooxygenase inhibitors (e.g. aspirin), adenosine diphosphate (ADP) receptor inhibitors (e.g. clopidogrel), phosphodiesterase inhibitors (e.g. cilostazol), glycoprotein I IB/I I A inhibitors (e.g. tirofiban), and adenosine reuptake inhibitors (e.g. dipyridamole); (14) anti-obesity agents, such as appetite suppressant (e.g. ephedrine), including noradrenergic agents (e.g. phentermine) and serotonergic agents (e.g. sibutramine), pancreatic lipase inhibitors (e.g. orlistat), microsomal transfer protein (MTP) modulators, diacyl glycerolacyltransferase (DGAT) inhibitors, and cannabinoid (CB1) receptor antagonists (e.g. rimonabant); (15) feeding behavior modifying agents, such as orexin receptor modulators and melanin-concentrating hormone (MCH) modulators; (16) glucagon like peptide-1 (GLP-1) receptor modulators; (17) neuropeptideY (NPY)/NPY receptor modulators; (18) pyruvate dehydrogenase kinase (PDK) modulators; (19) serotonin receptor modulators; (20) leptin/leptin receptor modulators; (21) ghrelin/ghrelin receptor modulators; or (22) monoamine transmission-modulating agents, such as selective serotonin reuptake inhibitors (SSRI) (e.g. fluoxetine), noradrenaline reuptake inhibitors (NARI), noradrenaline-serotonin reuptake inhibitors (SNRI), triple monoamine reuptake blockers (e.g. tesofensine), and monoamine oxidase inhibitors (MAOI) (e.g.

toloxatone and amiflamine), or a pharmaceutically acceptable salt, solvate, solvate of such a salt or a prodrug thereof.

In a further aspect of the invention there is provided the use of FKBP-L polypeptides and nucleic acid sequences encoding the same as a biomarker for obesity and obesity-related disorders. This could be measured by assessing the expression levels of FKBP-L in blood/tissue samples by ELISA/IHC; low FKBP-L expression levels would be associated with obesity. Alternatively, levels of mRNA encoding FKBP-L could be measured. In further alternative methods SNPs of FKBP-L could be determined and used to measure expected expression or activity of FKBP-L. This would allow subjects with decreased levels of expression or activity of FKBP-L to be selected for treatment with FKBP-L polypeptides or nucleic acids as discussed herein.

Suitably low expression levels of FKBP-L may be levels which provide 50% of FKBP-L levels relative to a control/normal sample. For example, typically FKBP-L may be about 1.4 ng/ml, more particularly 1.423 ng/ml (±0.1694SD) in control subjects. Suitably a value of less than 0.9 ng/ml, suitably 0.7 ng/ml, in particular less than 0.66 ng/ml may be considered as 'low' or 'reduced'. Suitably a low level of FKBP-L may be assessed in serum by ELISA (as discussed in FIGS. 14 and 15) or is tissues using immunohistochemical staining wherein the differences in intensity in the signal obtained can be assigned values such as high, medium and low.

Accordingly, there is provided a method of identifying patients with mutation of the FKBP-L gene or regulatory sequences which result in decreased expression of FKBP-L or results in expression of a less active form of FKBP-L. Likewise, mutations will be detected in blood samples using direct sequencing or allele-specific qPCR using primers designed to detect specific mutations associated with obesity.

Assessing the expression levels of FKBP-L in blood/tissue samples can be by determining an interaction between two agents for example determining whether an interaction between two proteins or two nucleic acids is present or absent. For example, the interaction of FKBP-L with an antibody specific for FKBP-L; or FKBP-L mRNA with a nucleic acid probe specific for the FKBP-L gene.

Detection may include quantification. Detection may include the use of an agent which is capable of detection (a label) using for example spectrophotometry, flow cytometry, or microscopy. Exemplary labels include radioactive isotopes (such as $^{3}H$, $^{14}C$, $^{15}N$, $^{35}S$, $^{90}V$, $^{99}Tc$, $^{111}Ln$, $^{125}I$, or $^{131}I$), fluorophores (such as fluorescein, fluorescein isothiocyanate, rhodamine or the like), chromophores, ligands, chemiluminescent agents, bioluminescent agents (such as luciferase, green fluorescent protein (GFP) or yellow fluorescent protein), enzymes that can produce a detectable reaction product (such as horseradish peroxidise, luciferase, alkaline phosphatase, beta-galactosidase) and combinations thereof. An example of an antibody which specifically binds FKBP-L is the FKBP-L rabbit polyclonal primary antibody (ProteinTech IL, USA, Cat no. 10060-1-AP). To detect this primary antibody, an anti-rabbit IgG horseradish peroxidase secondary antibody (GE Healthcare, Cat no. NA934V) may be used.

Preferred features and embodiments of each aspect of the invention are as for each of the other aspects mutatis mutandis unless context demands otherwise.

Each document, reference, patent application or patent cited in this text is expressly incorporated herein in their entirety by reference, which means it should be read and considered by the reader as part of this text. That the document, reference, patent application or patent cited in the text is not repeated in this text is merely for reasons of conciseness.

Reference to cited material or information contained in the text should not be understood as a concession that the material or information was part of the common general knowledge or was known in any country.

As used herein, the articles "a" and "an" refer to one or to more than one (for example to at least one) of the grammatical object of the article.

"About" shall generally mean an acceptable degree of error for the quantity measured given the nature or precision of the measurements.

Throughout the specification, unless the context demands otherwise, the terms 'comprise' or 'include', or variations such as 'comprises' or 'comprising', 'includes' or 'including' will be understood to imply the includes of a stated integer or group of integers, but not the exclusion of any other integer or group of integers.

The present invention is further illustrated by the accompanying Examples which do not limit the scope of the invention.

EXAMPLES

The activity of the polypeptides and nucleic acids according to the invention was assessed in following experiments to determine their use as anti-obesity agents. The importance of FKBP-L levels through generation of FKBP-L deficient mice, and FKBP-L in obese patient serum, also highlight how a deficiency in FKBP-L levels or function could be used as biomarkers of obesity or obesity-related disorders.

Example 1

Comparison of Weight Gain and Increased Adiposity in $Fkbpl^{+/-}$ Mice with their Wild-Type (WT) Littermates, $Fkbpl^{+/+}$ on a Normal and on a High Fat Diet.

To generate FKBP-$L^{+/-}$ mice, C57BL/6N mice were used for microinjection of the Fkbpl-targeted embryonic stem cell line, JM8A3. The vector, ES cell(s), and/or mouse strain used was generated by the trans-NIH Knock-Out Mouse Project (KOMP) and obtained from the KOMP Repository (www.komp.org). ES cells were obtained from KOMP (USA); exon 2 of Fkbpl was deleted. (Fkbpl—IKMC Project: 41363; Clone number: EPD0466_1_C01), obtained from KOMP (UC Davis Repository, USA) were microinjected at MRC Harwell (UK) into C57BL/6N mice mouse blastocysts to establish germ-line transmission. The resulting chimeric offspring were bred with C57BL mice to obtain germline transmission of the mutated Fkbpl allele and obtain Fkbpl+/neo mice. Subsequently, Fkbpl+/neo mice were crossed with B6N-TgN (ACTB-Cre)3Mrt/H mice (βactin-Cre Tg) to ubiquitously remove the floxed neomycin selective marker from the Fkbpl mutated allele (Fkbpl+l). $Fkbpl^{+/-}$ mice were further bred to remove the β-actin-Cre from the germline. The resulting $Fkbpl^{+/-}$ was used in comparison to their $Fkbpl^{+/+}$ littermates in all further analyses.

Figure 3:
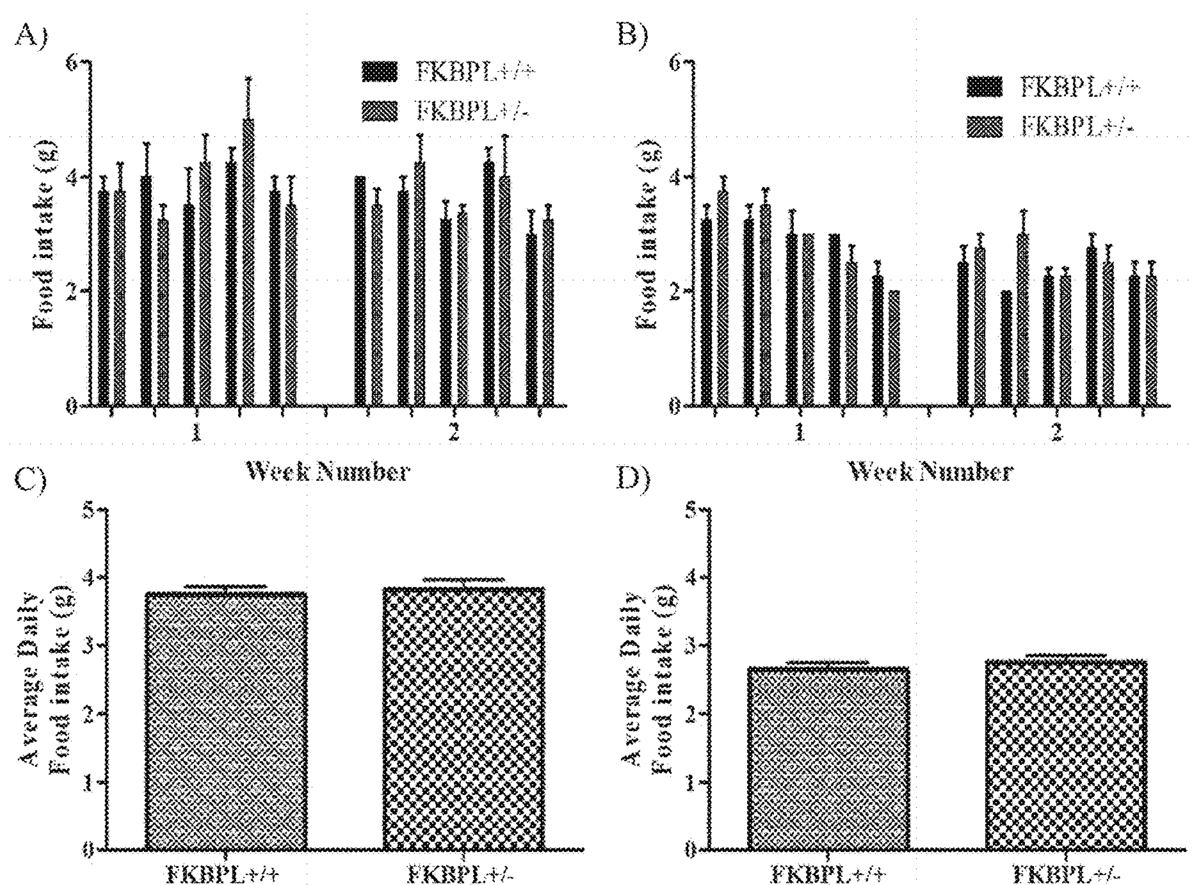
FIG. 3 provides graphs showing the weekly food intake vs the time for Fkbpl$^{+/-}$ mice and WT littermates (Fkbpl$^{+/+}$ mice) fed a normal chow diet or a high fat diet (HFD)—Food intake of male Fkbpl$^{+/+}$ and Fkbpl$^{+/-}$ mice was measured daily for two weeks. Mice were fed either standard chow or high fat diet. They were housed individually. Food intake of Fkbpl$^{+/-}$ mice on a standard chow or high fat diet was not significantly different to wild-type (VVT) littermates, Fkbpl$^{+/+}$. (A) Daily food intake for Fkbpl$^{+/+}$ (n=4) and Fkbpl$^{+/-}$ (n=4) male mice receiving a standard chow diet. (B) Daily food intake for Fkbpl$^{+/+}$ (n=4) and Fkbpl$^{+/-}$ (n=4) male mice receiving a high fat diet. (C) Average daily food intake for Fkbpl$^{+/+}$ (n=4) and Fkbpl$^{+/-}$ (n=4) male mice receiving a standard chow diet. (D) Average daily food intake for Fkbpl$^{+/+}$ (n=4) and Fkbpl$^{+/-}$ (n=4) male mice receiving a high fat diet.

$Fkbpl^{+/+}$ mice from the Fkbpl transgenic strain developed, were housed in open top boxes. Up to four mice were housed per box to avoid stress. Mouse were fed a normal chow diet and allowed to age. $Fkbpl^{+/-}$ mice (n=27) began to develop obesity compared to $Fkbpl^{+/+}$ mice (n=20) between age 2-6 months old on this normal diet, as illustrated in FIGS. 1A and 1B. In a separate study, where mice were individually caged to measure food intake, results suggest that food intake was similar in Fkbpl$^{+/-}$ and Fkbpl$^{+/+}$ mice was similar as provided in FIG. 3.

For the high fat diet study 10 mice per group were used. All mice were weighed at experimental start date, biweekly for the first three weeks to ensure health, and weekly thereafter. Mice were solely fed a high fat diet comprising 60% fat (Cat no. F3282, Dates and, USA). Food provided was weighed biweekly for three weeks, then weekly, to ensure equal food provisions between boxes, with an allowance of 5 g per mouse per day assumed.

After feeding a high fat diet, mice developed obesity between 3-10 weeks as shown in FIG. 10, however Fkbpl$^{+/-}$ mice gained significantly more weight than Fkbpl$^{+/+}$ littermates.

Figure 2:
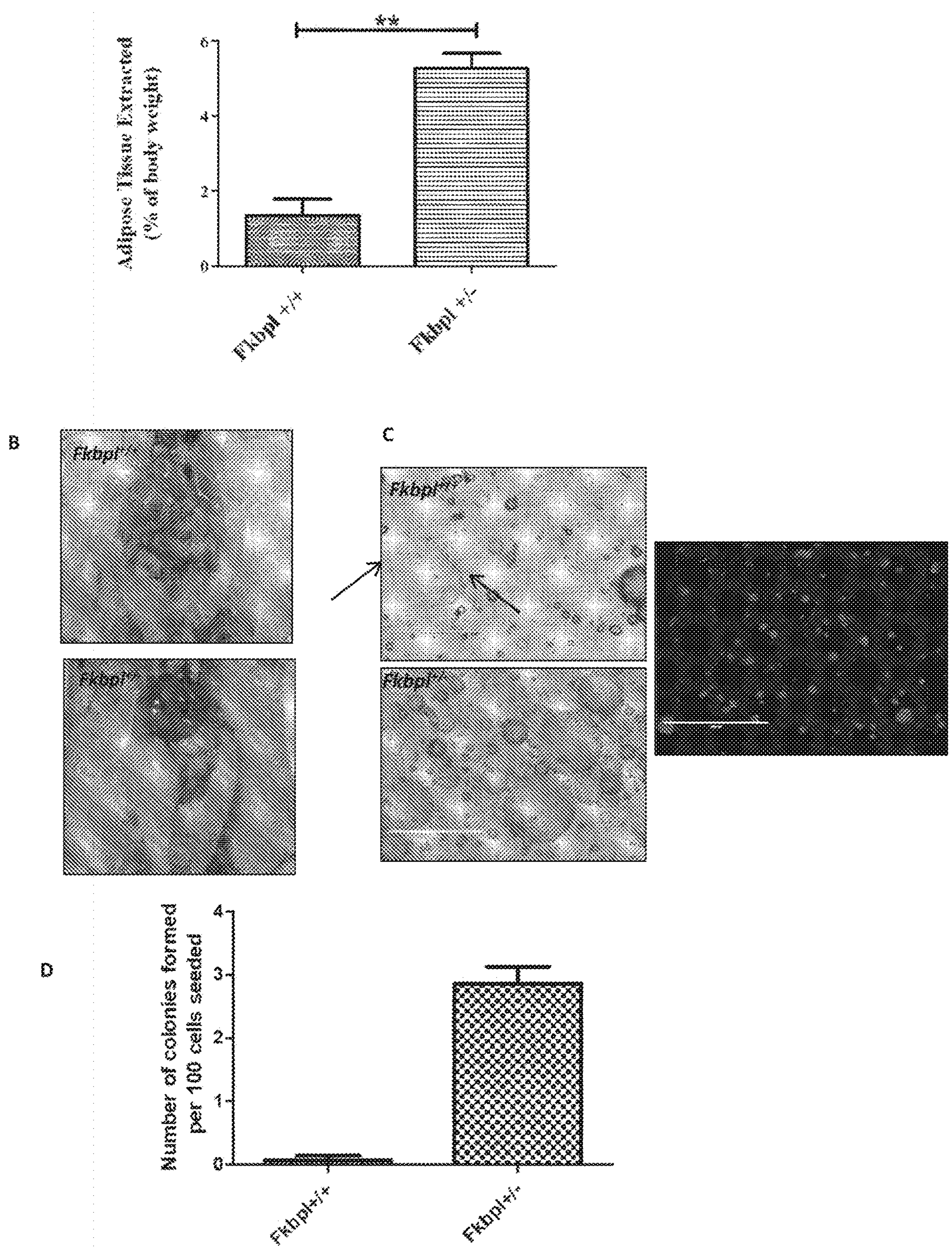
FIG. 2A is a bar graph showing increasing of % adipose tissue by % of body weight in Fkbpl$^{+/-}$ and Fkbpl$^{+/+}$ mice (>5 months) on a normal diet—Fkbpl$^{+/-}$ mice had an increase % of subcutaneous body fat compared to Fkbpl$^{+/+}$ mice of same age (>5 months) (n=3).
FIG. 2B is an image of visceral fat surrounding major organs of Fkbpl$^{+/-}$ and Fkbpl$^{+/+}$ mice—Fkbpl$^{+/-}$ mice have increased visceral fat surrounding major organs than Fkbpl$^{+/+}$ littermates.
FIG. 2C is a representative image of the number and size of adipocytes in Fkbpl$^{+/-}$ and Fkbpl$^{+/+}$ mice—Adipoctyes isolated from Fkbpl$^{+/-}$ mice were more numerous and larger in size than those from Fkbpl$^{+/+}$ and they could be stained by Nile-Red (representative images). ** $p<0.01$, * $p<0.05$.
FIG. 2D is a bar graph showing % increase in adipose stem cells isolated from Fkbpl$^{+/-}$ mice compared to WT littermates (Fkbpl$^{+/+}$ mice). The data have been generated using a protocol based on the method developed by Halvorsen et al.

Fkbpl$^{+/-}$ mice also had increased adiposity associated with their weight gain (FIG. 2A, B) and demonstrate a significant increase in the number and size of adipocytes (FIG. 2C). It is important to note that obese individuals tend to have more adipocytes (hyperplasia) which are larger in size (hypertrophy). These adipocytes were successfully characterised using the adipocyte specific stain, Nile Red (FIG. 2*c*). We were also able to purify more adipocyte stem cells (ASCs) from the fat tissue of Fkbpl$^{+/-}$ mice compared to Fkbpl$^{+/+}$ mice (FIG. 2D).

The above results indicate that a deficiency in FKBP-L is associated with adipogenesis, overweight and obesity.

Example 2

Oral Glucose Tolerance Test (OGTT)

An OGTT was performed by fasting the mice for 4 h, taking baseline blood glucose, administering 40% D-glucose, and recording two further blood glucose readings at 30 and 60 min. As illustrated in FIG. 1D, Fkbpl$^{+/-}$ mice has demonstrated a reduced glucose tolerance compared to wild-type Fkbpl$^{+/+}$ mice.

The results of this experiment indicate that a deficiency in FKBP-L is associated with the development of diabetes mellitus type 2.

Example 3

Weight Gain and Glucose Intolerance Improved Following Administration of FKBP-L's Peptide Derivative ALM201

For the high fat diet study, 40 age and sex matched mice were chosen with an age range of 6-10 weeks at the experimental start date. Mice were randomised into four groups: PBS Fkbpl$^{+/-}$, PBS Fkbpl$^{+/+}$, ALM201 Fkbpl$^{+/-}$ and ALM201 Fkbpl$^{+/+}$. Power calculations were utilised to predict the number of mice needed to show statistical significance. Taking group 1 mean weight to be 25 g and group 2 mean weight to be 45 g, with a standard deviation of 13 gives a sample size of eight mice per group when powered to 0.8, with $\alpha$=0.05. 10 mice per treatment group were used. All mice were weighed at experimental start date, biweekly for the first three weeks to ensure health, and weekly thereafter. Mice were solely fed a high fat diet comprising 60% fat (Cat no. F3282, Dates and, USA). Food provided was weighed biweekly for three weeks, then weekly, to ensure equal food provisions between boxes, with an allowance of 5 g per mouse per day assumed. ALM201 was reconstituted in PBS, stored at −20° C., and injected subcutaneously at a dose of 0.3 mg/kg, 5 days per week. Mice in the control group were injected with a comparable volume of PBS, 5 days per week.

Figure 4:
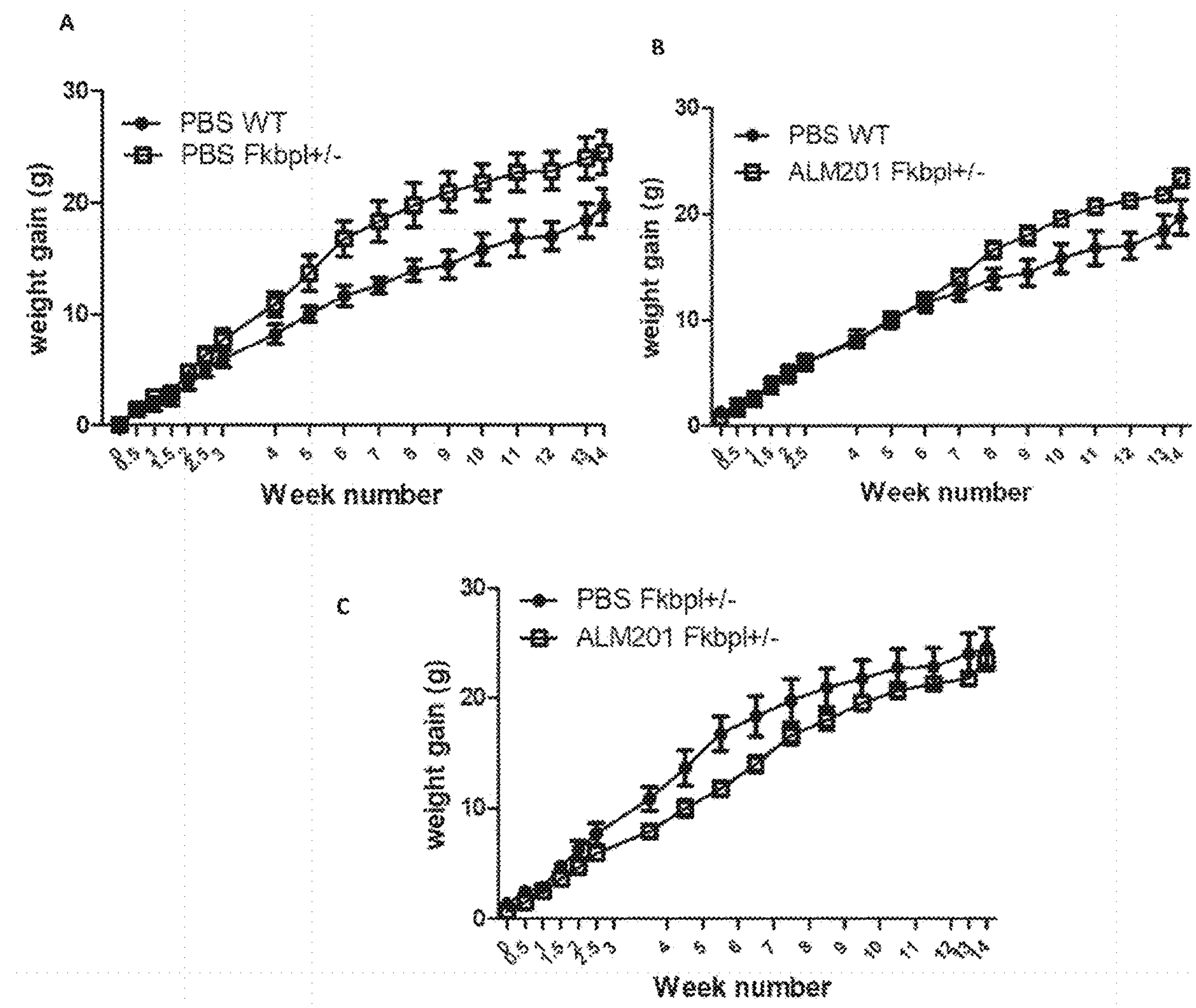
FIG. 4A shows the weight gain of Fkbpl$^{+/+}$ wild-type (WT) and Fkbpl$^{+/-}$ mice vs time after feeding a high fat diet (HFD)—Fkbpl$^{+/-}$ mice have a tendency to gain significantly more weight than Fkbpl$^{+/+}$ wild-type (WT) mice after feeding a high fat diet (HFD) ($p<0.05$; two-way ANOVA).
FIG. 4B shows the weight gain of Fkbpl$^{+/+}$ wild-type (WT) mice and Fkbpl$^{+/-}$ treated with ALM201 (an FKBP-L nucleic acid sequence comprising amino acids) vs time after feeding a high fat diet (HFD)—administering ALM201 (0.3 mg/kg to Fkbpl$^{+/-}$ normalises the mouse weight gain to that of Fkbpl$^{+/+}$ so that the difference is no longer significant.
FIG. 4C shows the weight gain of Fkbpl$^{+/-}$ and Fkbpl$^{+/+}$ treated with ALM201 vs time after feeding a high fat diet (HFD)—ALM201 reduces and normalises weight gain as Fkbpl$^{+/-}$ mice given ALM201 are compared to Fkbpl$^{+/-}$ mice administered PBS.
Figure 5:
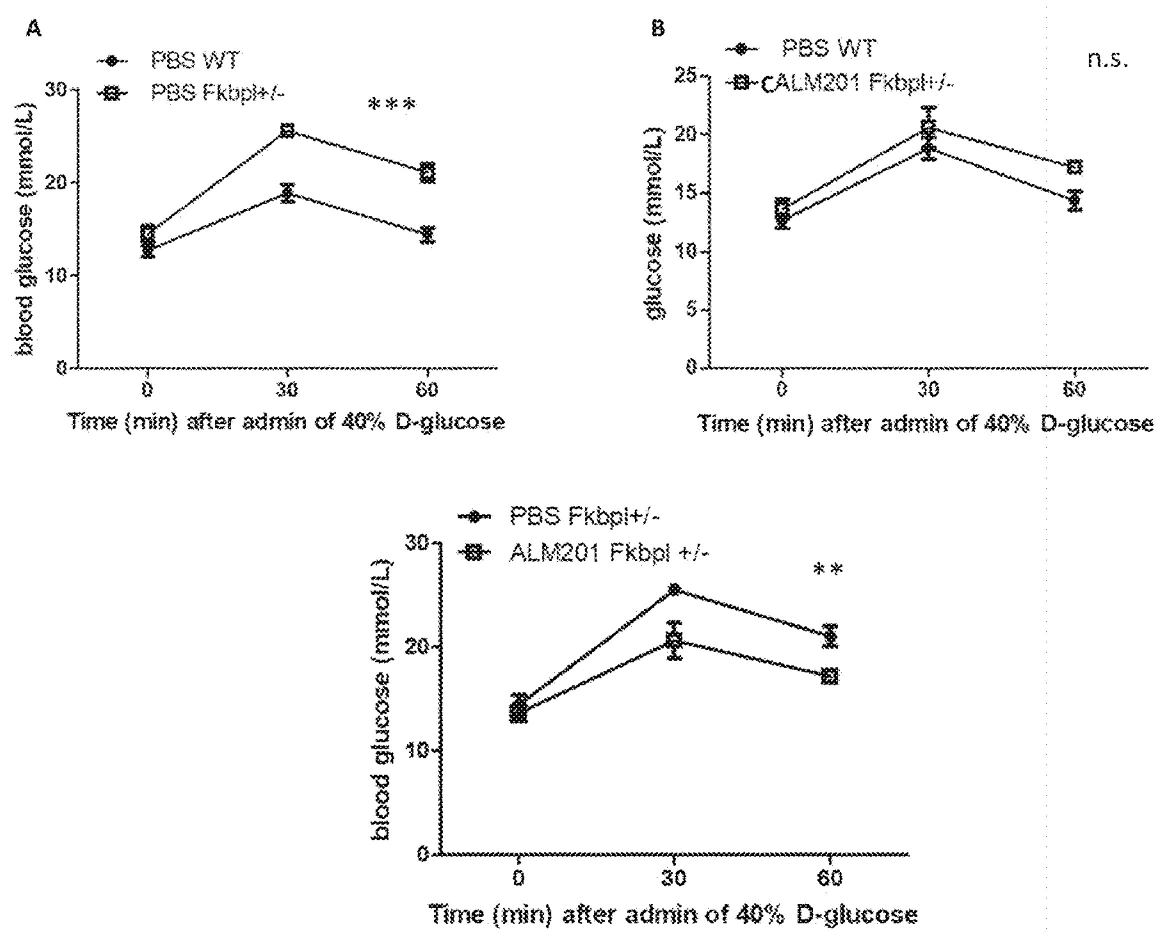
FIG. 5A shows the blood glucose concentration in Fkbpl$^{+/-}$ and Fkbpl$^{+/+}$ mice wild-type (WT) vs. time after administration of 40% glucose solution (Oral Glucose Tolerance Test (OGTT))—Fkbpl$^{+/-}$ had significantly higher blood glucose readings at 30 and 60 min than Fkbpl$^{+/+}$ mice.
FIGS. 5B and 5C show blood glucose concentration in Fkbpl$^{+/-}$ treated with ALM201 and Fkbpl$^{+/+}$ mice wild-type (WT) and Fkbpl$^{+/-}$ treated with ALM201 and Fkbpl$^{+/-}$ mice vs. time after administration of 40% glucose solution (Oral Glucose Tolerance Test (OGTT))—(B) There was no significant difference observed between the blood glucose levels of Fkbpl$^{+/-}$ and Fkbpl$^{+/+}$ mice administered ALM201 (C) Fkbpl$^{+/-}$ given ALM201 had significantly lower blood glucose readings at 30 and 60 min than Fkbpl$^{+/-}$ mice given PBS;  $p<0.01$, * $p<0.001$.

As shown in FIGS. 4 and 5, the weight gain and glucose intolerance in Fkbpl+/− mice fed a high fat diet was significantly reduced following supplementation with ALM201. ALM201 also partially prevented weight gain in wild-type mice.

These data indicate that a pharmacologically-based increase in FKBP-L could potentially be protective in development of obesity and glucose intolerance.

Example 4

Regulation of the Obesity Protein, SIRT1 (mRNA and Protein) by FKBP-L

For mRNA from mouse tissues: Mouse organs from Fkbpl$^{+/+}$ and Fkbpl$^{+/-}$ mice were excised (pooled from three mice), stored in RNA/ater solution (Life Technologies, UK) at −80° C., and then processed for qRT-PCR. In brief, samples were thawed immediately before use, and 30 mg of lung, liver, and kidney, and 20 mg of spleen was added to lysis buffer from the GeneJET RNA Purification Kit (ThermoScientific, UK) in GentleMACS M tubes (Miltenyi Biotec, UK) and tissues disrupted using the RNA program on the GentleMACS Tissue Dissociator (Miltenyi Biotec, UK). Dissociated tissue was then processed as per the manufacturer's protocol in the GeneJET RNA Purification Kit (ThermoScientific, UK). RNA purity was confirmed using the NanoDrop Spectrophotometer (2000c, Thermo Scientific), where 260/280 should be 2.0, and 260/230 should be 2.0-2.2. RNA samples were stored at −80° C. cDNA was prepared from 1 μg of extracted RNA using the Roche first strand cDNA synthesis kit (Roche, UK) following the manufacturer's protocol. cDNA was prepared for quantitative realtime polymerase chain reaction (qRT-PCR) using the Roche Lightcycler Probes 480 Mastermix kit (Roche, UK) and Applied Biosystems TaqMan Gene expression assays for murine Fkbpl (Mm00498192_s1) and Gapdh (Mm99999915_g1) (Applied Biosystems) or Roche Real-time Ready TaqMan gene expression mono hydrolysis Probes for Sirt1 (assay ID 310480, config. No 100052233) (Roche, UK) to amplify the previously obtained cDNA on the LightCycler 480 qRT-PCR machine (Roche, UK). 2 μL cDNA was added to 5 μL Mastermix, along with 2 μL water, and 1 μL of the relevant TaqMan probe mix. Samples containing either no DNA or no reverse transcriptase (RT) mix were also prepared as negative controls for the PCR reaction. A standard curve was determined for each probe and used to determine the efficiency of each PCR reaction. PCR reactions were set up in a 96 well plate (Roche, UK), sealed with a microseal adhesive film (Roche, UK), and loaded into the LightCycler device. Samples were denatured at 95° C. for 10 min and subjected to 45 cycles of denaturing at 95° C. for 10 sec, annealing at 60° C. for 30 sec and 72° C. for 10 sec. Fluorescence was measured every cycle. The resulting crossing points (Cp—first cycle where a sample shows logarithmic amplification) were calculated using the Roche LightCycler 480 software, and quantified using the standard curve efficiency. Cp values less than 32 indicated sufficient RNA expression to quantify differences accurately. Sample Cp values were corrected to sample Gapdh Cp values.

Figure 6:
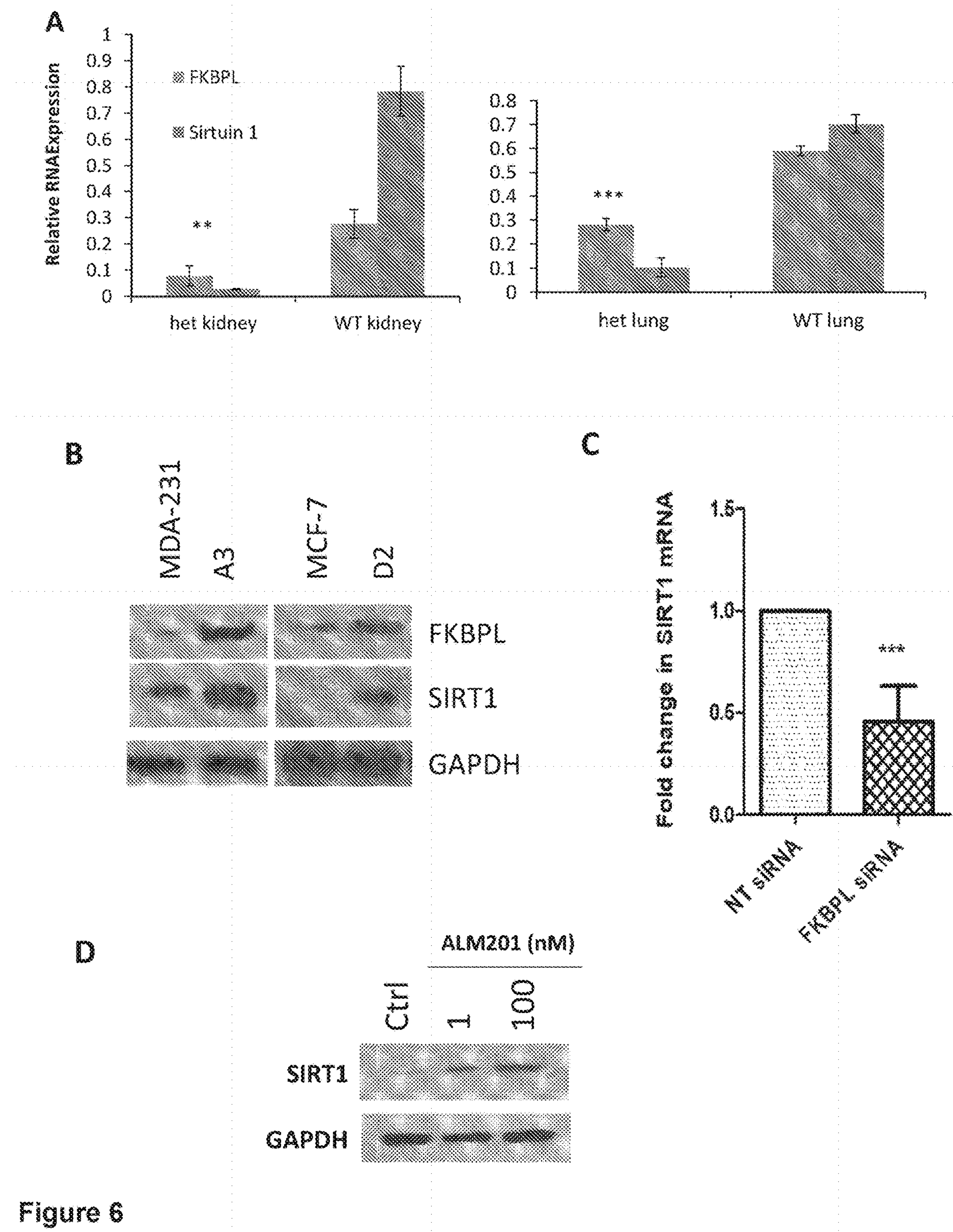
FIG. 6A illustrates qRT-PCR of FKBP-L and SIRT1 mRNA in tissues from Fkbpl$^{+/-}$ (het) mice and Fkbpl$^{+/+}$ (WT) littermates in kidney and lung tissues.
FIG. 6B shows western blots demonstrating increased SIRT1 in FKBP-L over expressing stable cell lines (A3 and D2) compared to parental lines (MDA and MCF-7).
FIG. 6C qRT-PCR demonstrating a reduction in SIRT1 mRNA following FKBP-L siRNA transfection compared to NT control.
FIG. 6D shows SIRT1 protein levels following ALM201 treatment. Data points are mean±SEM. $n\geq3$. $p<0.001$ (one-way ANOVA).

FIG. 6A shows a significant reduction in SIRT1 mRNA levels in Fkbpl+/− mice compared to Fkbpl+/+ mice across a range of tissues.

For assessing protein levels: Cell lysates were prepared in RIPA buffer from MDA-MB-231, A3, MCF-7 and D2 cells and subjected to Western Blotting. The membrane was then probed with a 1:1000 dilution of rabbit FKBP-L IgG polyclonal primary antibody (Proteintech UK, cat: 10060-1-AP), 1:1000 rabbit SIRT1 IgG monoclonal primary antibody (Abcam, UK cat: ab32441) in 3% blocking solution overnight on a rocker at 4° C. The membrane was washed with PBS-Tween and then PBS for 5 min each, and was probed for an hour with a 1:5000 dilution of ECL anti rabbit IgG HRP linked whole secondary antibody (GE Healthcare UK Ltd.) Membranes were washed and developed as in section 2.2.2.11.3. Membranes were then stripped with Restore™ Western Blot Stripping Buffer (Thermo Scientific) for 10 min, washed, re-probed with rabbit GAPDH primary antibody (Sigma-Aldrich), and a 1:5000 dilution of ECL anti rabbit IgG HRP linked whole secondary antibody (GE Healthcare UK Ltd.) and developed as above. SIRT1 was identified as a band around 110 kDa, FKBP-L at 42 kDa.

For FKBP-L siRNA-mediated knockdown: $2\times10^6$MDA-MB-231 cells supplemented with complete media were seeded into a 90 mm plate (Nunc, UK) and left to adhere for 24 h prior to transfection. Complete media was aspirated and 5 mL of Opti-MEM media (Gibco, UK) was added to each well for 2 h. Cells were then transfected with FKBP-L siRNA (Invitrogen, UK). siFKBP-L (Invitrogen, UK) was supplied at a 20 nM concentration, and comes as three siRNA;

```
                                    (SEQ ID NO: 41)
F1 (GGAGACGCCACCAGUCAAUACAAUU),

                                    (SEQ ID NO: 42)
F2 (GCUGAACUUGAAGGAGACUCUCAUA),
and

                                    (SEQ ID NO: 43)
F3 (CAGCCAAAUUCUAGAGCAUACUCAA).
```

These are designed to be used together to achieve transient knockdown. Cells were transfected using Oligofectamine™, with tubes A and B set up for each condition. 15 μL of each siRNA was added to Tube A, and was diluted with 746 μL Opti-MEM per sample. In tube B, 28 μL Oligofectamine™ was diluted to 111.96 μl with Opti-MEM per sample. Tubes were left to incubate at room temperature for 5 min, and were then combined and incubated at room temperature for 20 min before addition of the 900 μL total to the appropriate plate. Cells were incubated with transfection mix for 4 h at 37° C., and then incubated with media containing 30% FCS for 72 h.

A non-targeting siRNA (Invitrogen, UK) was also prepared at the same concentration and added to a separate plate as a control, as well as an untreated plate with no transfection agent added. Cell lystates were stored in RNA/ater solution (Life Technologies, UK) at −80° C., and then processed for qRT-PCR to assess SIRT1 levels as described previously.

FKBP-L overexpression in A3 and D2 cells was associated with increased SIRT1 mRNA and protein levels (FIG. 6B), whilst FKBP-L knockdown led to a reduction in SIRT1 mRNA (FIG. 6C).

These data indicate that the reduction in SIRT1 levels in the obese Fkbpl$^{+/-}$ mice, might be partially responsible for the increased weight gain and adiposity. Importantly, FKBP-L's peptide derivative, ALM201 (SEQ ID NO:10), increased SIRT1 levels as shown in FIG. 6D.

Example 5

Figure 7:
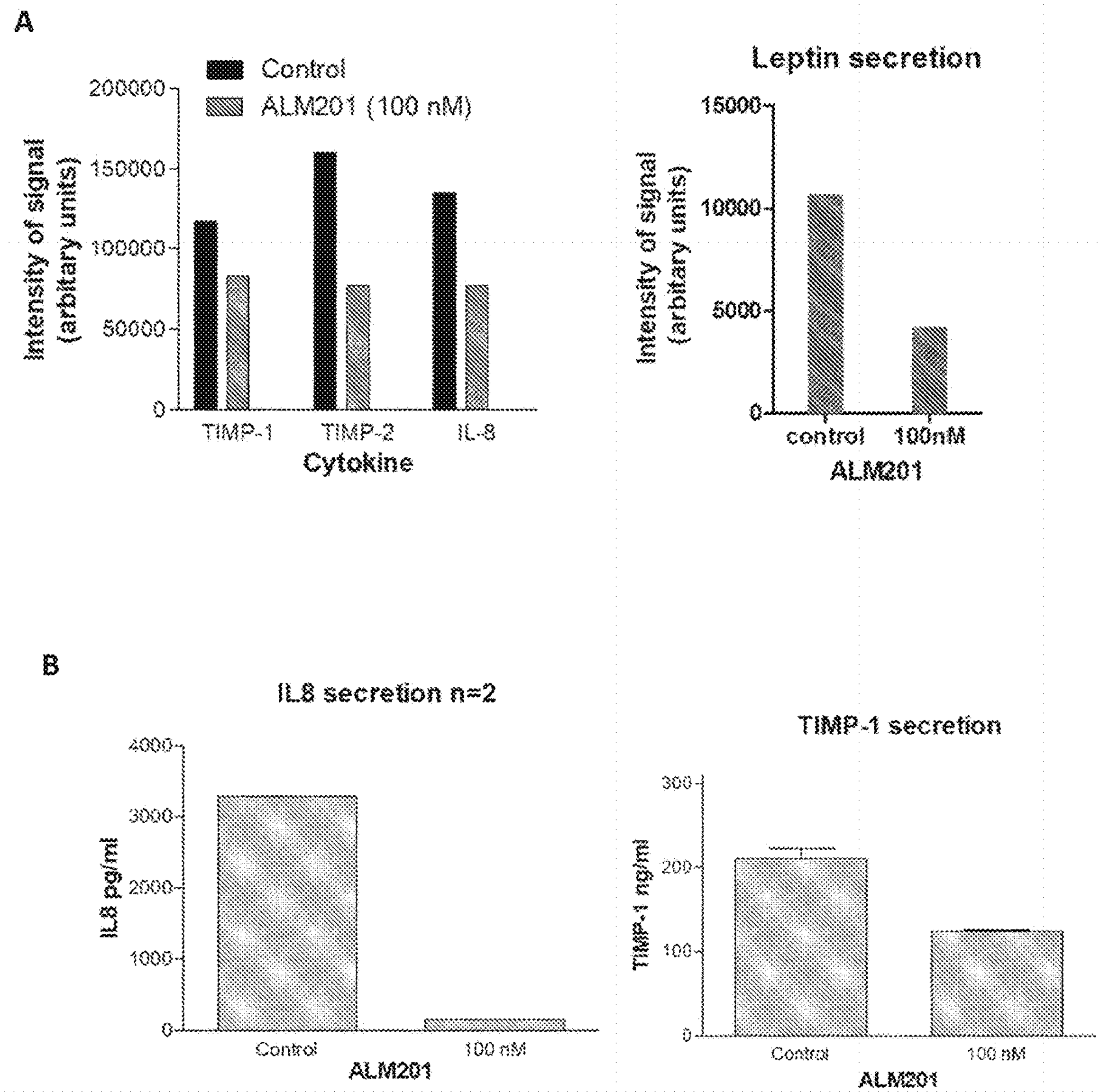
FIGS. 7A and 7B illustrate the level of secretion of leptin, IL8 and TIMP Secretion after treatment with FKBP-L's therapeutic peptide, ALM201—A Ray Biotech cytokine array was used to measure cytokines in the spent medium of MDA231 cells after exposure to ALM201. Blots were then quantitated by densitometric analysis using Ray Biotech software.

Evidence that ALM201 Modifies Cytokine Release Associated with Obesity:

Data provided in FIG. 7 demonstrate that FKBP-L's therapeutic peptide, ALM201, can reduce secreted leptin, TIMP1 and IL-8 levels, such levels are known to be increased in obesity. A Ray Biotech cytokine array was used to measure cytokines in the spent medium of MDA231 cells after exposure to ALM201. Blots were then quantitated by densitometric analysis using Ray Biotech software. IL8 and TIMP1 levels were then validated by ELISA in two or three independent repeats. A reduction in these cytokines would reduce the obesity phenotype.

Example 6

Figure 12:
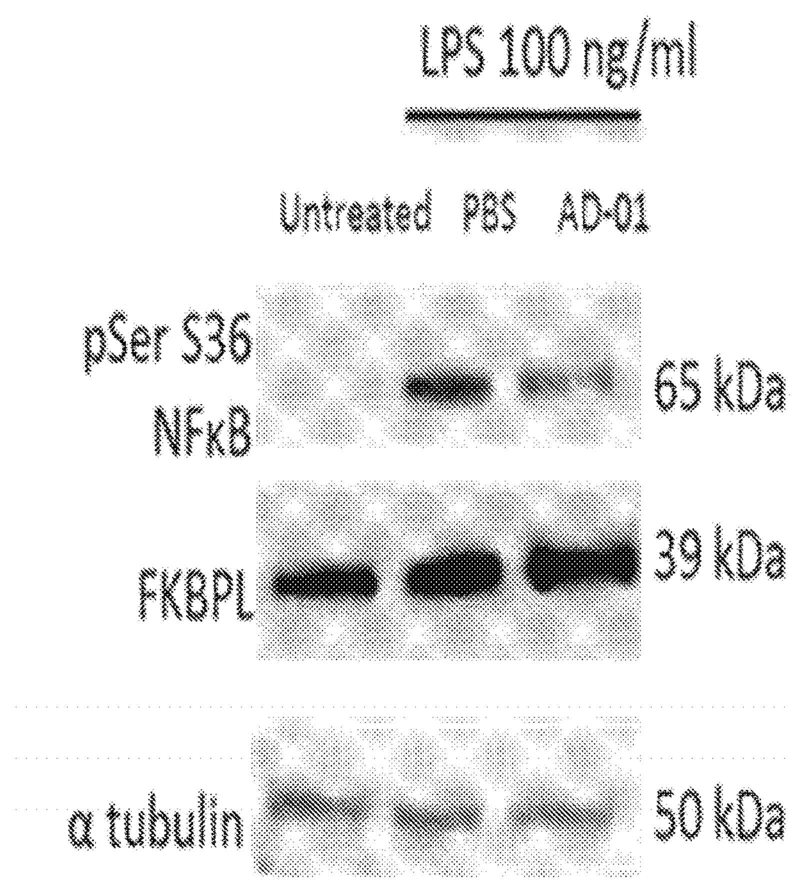
FIG. 12 illustrates the FKBP-L peptide, AD-01 (SEQ ID NO: 10), abrogates LPS-induced activation of NFkB in THP-1 monocytes—Cells were stimulated with 100 ng of LPS which results in activation of NFkB phosphorylation. AD-01 abrogated that increase—cell lysates were collected from THP-1 monocytes 6 hour after treatment and subjected to western blot analysis using specific antibodies indicated.
Figure 13:
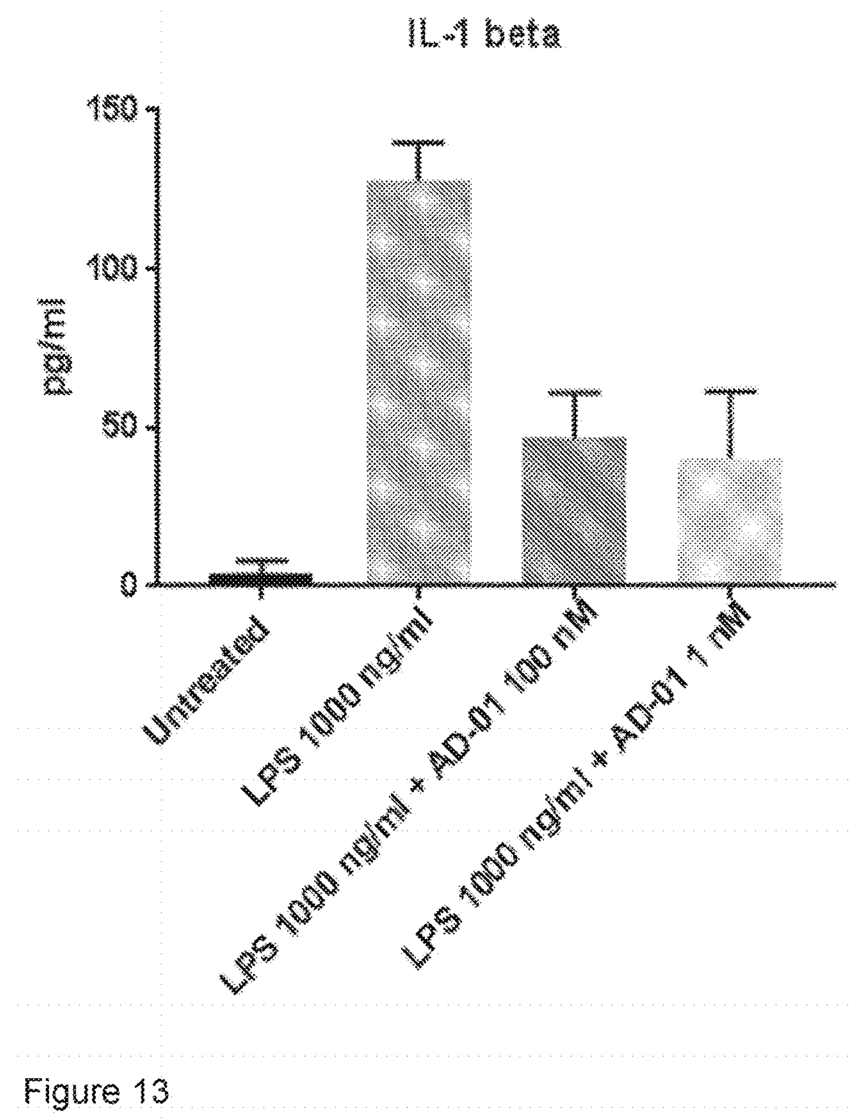
FIG. 13 illustrates the FKBP-L peptide, AD-01, abrogates LPS-induced activation of IL-1β in THP-1 monocytes—Cells were stimulated with 1000 ng of LPS. 24 h later condition medium was collected to assess secretion of cytokines—IL-1β, measured by ELISA was significantly increased by LPS and was significantly abrogated by AD-01.

Evidence that FKBP-L/AD-01 can Reduce Proinflammatory Responses Associated with Obesity Impaired local proinflammatory response in the adipocyte leads to increased ectopic lipid accumulation, glucose intolerance, and systemic inflammation. Adipocyte hypertrophy and hypoxia provide ideal environments for the development of adipose tissue inflammation, by promoting the influx of macrophages and other immune cells. Data provided in FIG. 12 show that FKBP-L fragments, AD-01 (24 aa peptide), can inhibit lipopoylsaccaride induced NFkB signalling in the THP1 monocyte (macrophage) cell line and this results in a dramatic reduction in the pro-inflammatory cytokine IL-1β secretion in obesity as observed in FIG. 13.

THP1 cells were treated with 100 ng/ml LPS and cell lysates harvested and subjected to western blotting as described in Example 4, using primary antibody against pSER36 NFkB (at a 1:1000 dilution) and a 1:5000 dilution of ECL anti rabbit IgG HRP linked whole secondary antibody (GE Healthcare UK Ltd.). To measure IL-1β levels THP1 cells were treated with 1000 ng/ml LPS±AD-01 and conditioned cell culture medium was collected 24 h later and assessed using an IL-1β ELISA.

Macrophages within the adipose tissue are polarized to the M1 inflammatory phenotype, producing this proinflammatory cytokine. The inventors therefore consider endogenous FKBP-L and its therapeutic peptides may be protective of obesity through abrogation of inflammatory signalling in both adipocytes and macrophages.

Example 7

FKBP-L Controls the Adipogenic Process Associated with Obesity

Figure 11:
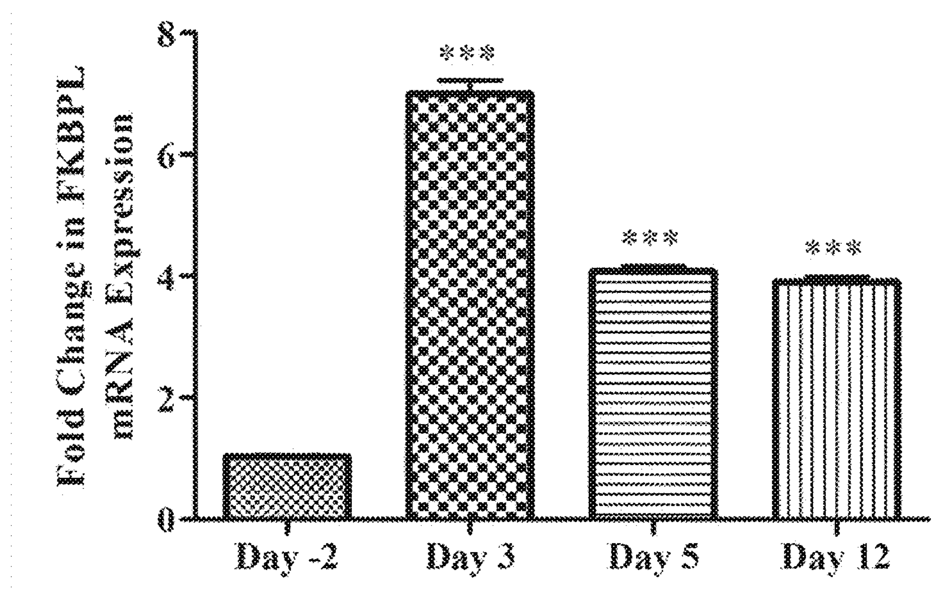
FIG. 11 illustrates FKBP-L mRNA levels increase upon stimulation of 2T3-L1 cells to undergo adipogenesis. 3T3-L1 cells were stimulated with adipocyte medium and mRNA isolated both prior (day −2) and 3-12 days after stimulation. qRT-PCR was used to determine FKBP-L levels. FKBPL levels were increased at day 3 following adipocyte differentiation Since FKBP-L is regulated during adipogenesis, the data suggests that it is involved in the process. Knockdown of FKBP-L (as seen in mice) may lead to inhibition of adipocyte differentiation, leading to adipocyte hypertrophy (observed in FIG. 10); resulting in enhanced inflammation worsening obesity and leading to insulin resistance.

FIG. 2C demonstrates a significant increase in the number and size of adipocytes in Fkbpl$^{+/-}$ mice compared to wild-type Fkbpl$^{+/+}$ mice. It was possible to purify more adipocyte stem cells (ASCs) from the fat tissue of Fkbpl$^{+/-}$ mice compared to Fkbpl$^{+/+}$ mice (FIG. 2D). It is important to note that obese individuals tend to have more adipocytes (hyperplasia) which are larger in size (hypertrophy). Subcutaneous adipose tissue from Fkbpl$^{+/-}$ mice also demonstrated hypertrophic adipocytes (FIG. 10). Hypertrophy is considered to be the main contributor to adipose tissue enlargement and is associated with abnormal adipocyte function leading to impaired insulin sensitivity. A deficiency in FKBP-L may therefore drive adipose tissue hypertrophy which leads to development of obesity in Fkbpl deficient mice. In vitro experiments in FIG. 11 support this where it was shown that FKBP-L mRNA levels are naturally increased during adipogenesis. If levels of FKBP-L were low then adipogenesis would be abrogated leading to hypertrophic adipocytes. This offers a mechanism by which FKBP-L may protect against obesity.

Example 8

FKBP-L (Nucleotides) Gene Therapy can Reduce Obesity in Mice on a Normal and High Fat Diet.

Male C57BL/6N mice at 8 weeks old were fed either HFD or standard chow, and randomised into three groups: no treatment (control; n=4), or weekly IV pFKBPL (n=5) or IV RALA-pFKBPL (n=5 and 4, respectively). The mice were then either fed a HFD comprising 60% fat (Cat no. F3282, Dates and, USA) for 4 weeks or normal chow and injected once a week with either pFKBPL (20 μg) or RALA-pFKBPL (20 μg). All mice were weighed at experimental start date and, weekly for four weeks to ensure health. Food provided was weighed to ensure equal food provisions between boxes, in a separate experiment, to assess difference in food intake, with an allowance of 5 g per mouse per day assumed. No significant changes in food intake were observed between experimental groups.

In another study, male C57BL/6N mice at 8 weeks old were fed either HFD or standard chow, and randomised into three groups: no treatment (control; n=3 and 4, respectively) or weekly IV pFKBPL (n=4 and 5, respectively) or IV RALA-pFKBPL (n=4 and 6, respectively). The mice were then either fed a HFD comprising 60% fat (Cat no. F3282, Dates and, USA) for 14 weeks or normal chow. After 14 weeks of feeding mice were injected once a week, for 3 weeks, with either pFKBPL (20 μg) or RALA-pFKBPL (20 μg), whilst maintaining their diet. All mice were weighed at experimental start date, weekly for the duration. Food provided was weighed to ensure equal food provisions between boxes, in a separate experiment, to assess difference in food intake, with an allowance of 5 g per mouse per day assumed. No significant changes in food intake were observed between experimental groups.

pFKBPL plasmid was made from MAX Efficiency DH5α-competent cells containing relevant plasmids (pFKBPL) cultured in a shaking incubator overnight at 37° C. in Luria broth containing the appropriate antibiotic. Plasmid DNA was isolated and purified using PureLink HiPure Plasmid Maxiprep Kits (Life Technologies) using the manufacturer's protocol. Plasmid DNA was dissolved in ultrapure water and stored at −20° C.

For RALA-pFKBPL, the RALA peptide was custom-synthesized using solid-state synthesis (fluorenylmethyloxycarbonyl [FMOC]) (Biomatik) and supplied as a desalted lyophilized powder. Reconstitution was in ultrapure water to a stock concentration of 11.6 mg/mL. Aliquots were stored at −20° C. until use.

pFKBPL/RALA nanocomplexes were constructed. Briefly, plasmid DNA was mixed with RALA immediately prior to injection, to facilitate electrostatic interaction of the anionic DNA with the cationic peptide. Nanoparticles were complexed at N:P10 (the N:P ratio is the molar ratio of positively charged nitrogen atoms in the peptide to negatively charged phosphates in the pDNA backbone—at N:P10, 290 μg of RALA is used to neutralize 20 μg of DNA). Nanoparticles were previously analyzed in terms of their hydrodynamic size and particle charge using a Nano ZS Zetasizer and DTS software (Malvern Instruments).

Figure 16:
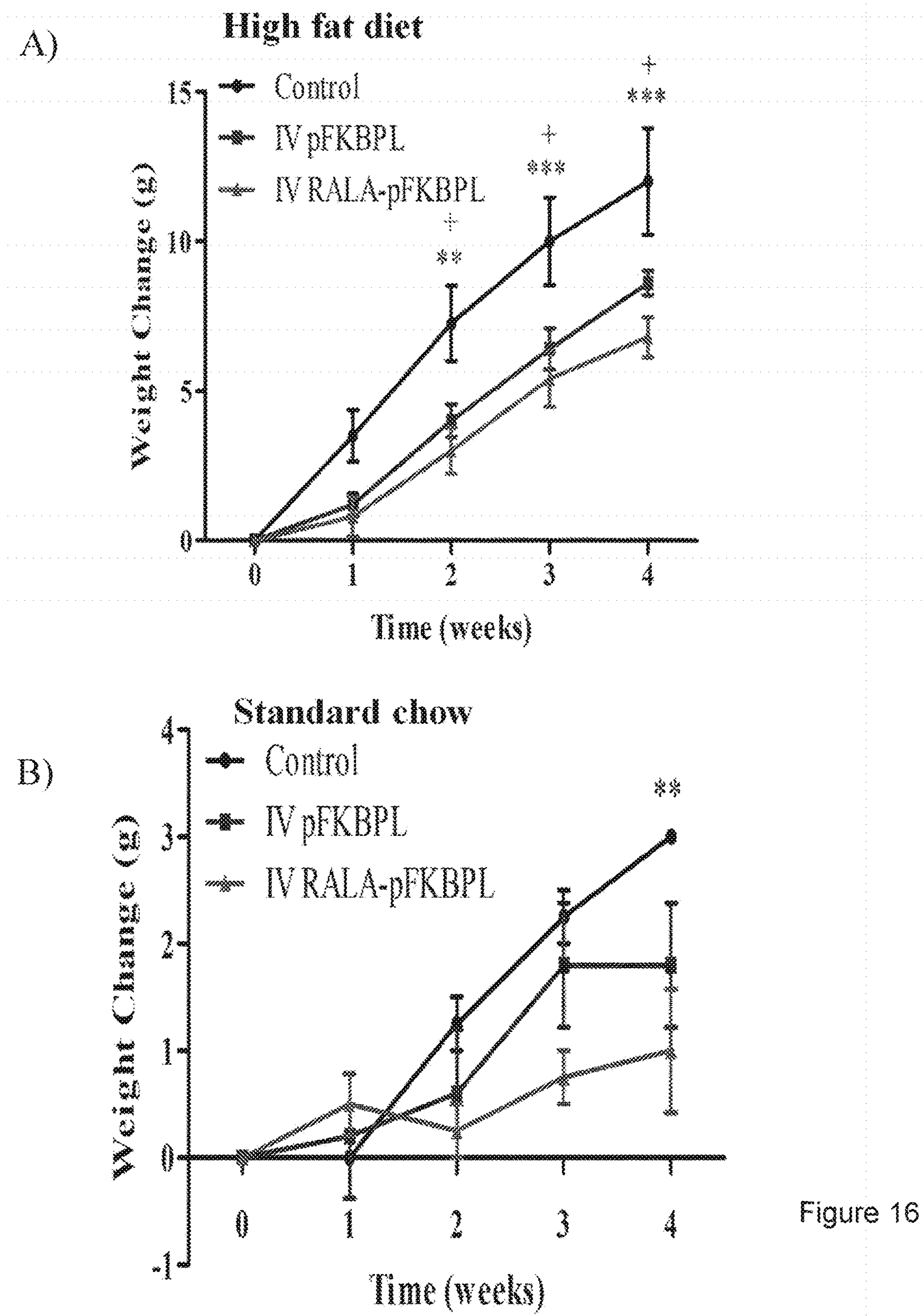
FIG. 16 illustrates that male C57BL/6N mice, age 8 weeks, fed a HFD, or standard chow, could be prevented from gaining weight when mice were treated via i.v. injection of naked plasmid DNA containing the full length FKBP-L gene (pFKBPL) or plasmid DNA containing the full length FKBP-L gene delivered using a novel peptide delivery system, RALA (RALA-pFKBPL), when these were delivered once weekly.

As shown in FIG. 16, the weight gain of mice increased on normal chow, but weight gain was significantly higher on a HFD. Notably, pFKBPL gene therapy significantly reversed weight gain on a HFD and a normal diet; the latter is very impressive as these mice were a normal weight. Finally, delivery of the gene therapy using the delivery peptide RALA (RALA-pFKBPL) significantly improved efficacy. In FIG. 17, where mice were fed a HFD or normal diet for 14 weeks and where HFD mice where severely obese before receiving any treatment, both pFKBPL and RALA-pFKBPL were able to reverse weight gain significantly; again the delivery peptide RALA improved efficacy. This data strongly suggest that an FKBP-L-based gene therapy can be used in obese individuals to reduce weight or could be used to prevent weight gain in individuals who are susceptible to obesity. There was a 50% decrease in weight gain following treatment with RALA-pFKBPL (this equates to a 5% decrease in total body weight compared to controls—FIG. 18). This is highly significant since the primary efficacy endpoint for weight loss medicines stipulated by the European Medicines Agency is 5-10%. This could be further optimised by more frequent agent administration and a higher dosage.

Example 9

Use of FKBP-L as a Biomarker of Obesity

Figure 1:
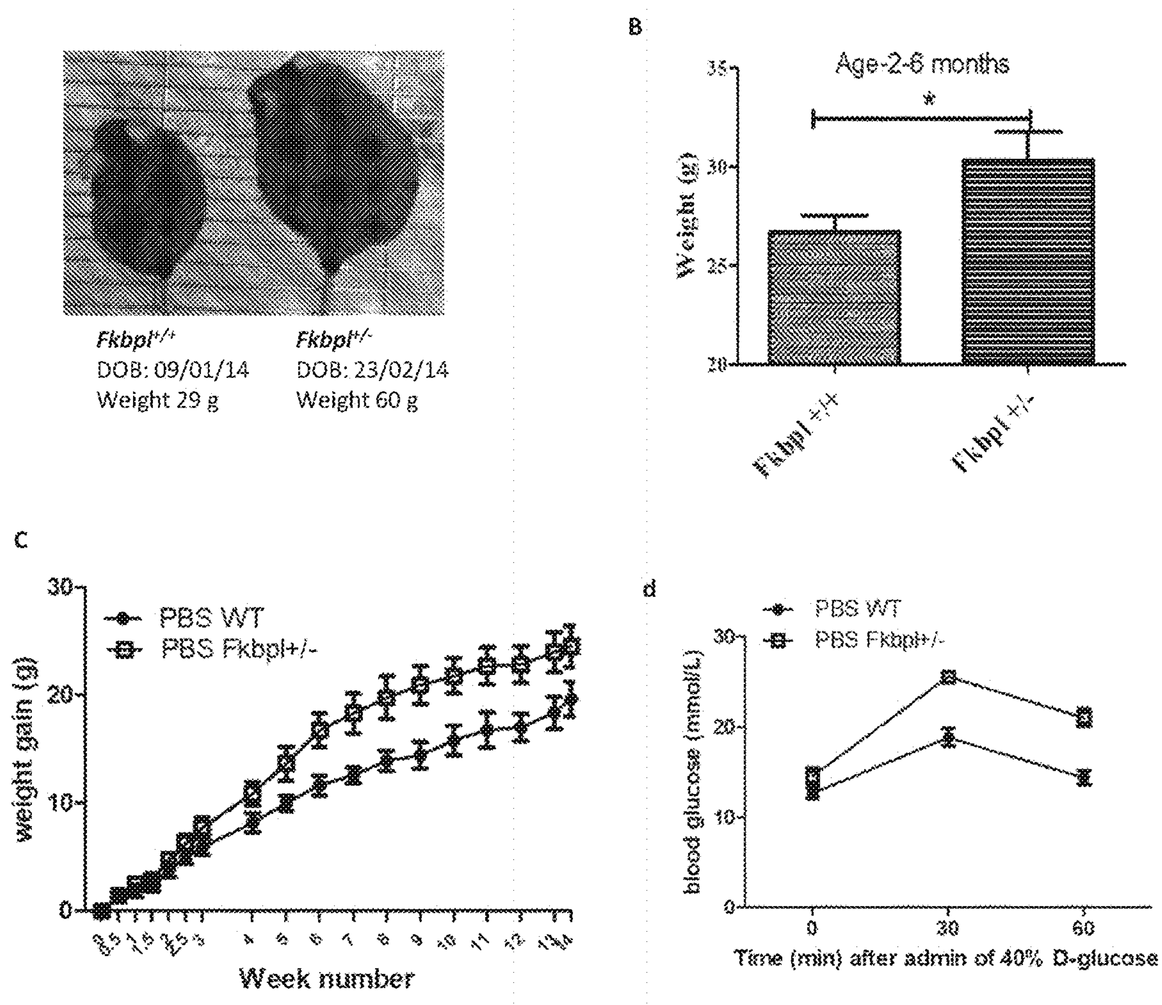
FIGS. 1A and 1B show that mice wherein one allele of FKBP-L was knocked out (i.e. Fkbpl$^{+/-}$ mice) are significantly heavier to their wild-type (WT) littermates, Fkbpl$^{+/+}$ on a normal diet between 2-6 months (1B) and in mice approximately 14 months old (1A).
FIG. 1C is a graph of percent weight gain of Fkbpl$^{+/-}$ and Fkbpl$^{+/+}$ mice in a high fat diet (HFD) vs. time ($p<0.05$; two-way ANOVA) and indicate that Fkbpl$^{+/-}$ mice have a tendency to gain significantly more weight than Fkbpl$^{+/+}$ mice ($p<0.05$; two-way ANOVA).
FIG. 1D is a graph of blood glucose concentration in Fkbpl$^{+/-}$ and Fkbpl$^{+/+}$ mice wild-type (VVT) vs. time after administration of 40% glucose solution (Oral Glucose Tolerance Test (OGTT))—blood glucose readings were recorded at 0, 30 and 60 min wherein Fkbpl$^{+/-}$ mice demonstrate intolerance to glucose upon stimulation with 40% glucose (Oral Glucose Tolerance Test (OGTT)) compared to Fkbpl$^{+/+}$ wild-type (WT) littermates i.e. Fkbpl$^{+/-}$ had significantly higher blood glucose readings at 30 and 60 min than Fkbpl$^{+/+}$ mice (WT mice).

FKBP-L levels predict obesity in mice (FIG. 1). Serum FKBP-L levels in obese (n=50) vs lean (n=30) children, aged 7-18 years, were assessed. Serum FKBP-L concentration was assessed by ELISA (Cloud Clone, USA). Serum samples, collected from lean and obese study participants were diluted 1:1 with standard diluent. Standards were prepared using the standard diluent with final concentrations in the range 0.156 ng/mL to 10 ng/mL. Standards and diluted serum samples were pipetted into wells (100 μL per well) on the pre-coated ELISA plate and incubated at 37° C. for 2 h. Standards and samples were then removed from each well and 100 μL of Detection Reagent A was added to each well, without washing. The ELISA plate was then incubated for 1 h at 37° C. Detection Reagent A was then removed and wells were washed three times with 300 μL of 1× Wash Buffer. 100 μL of Detection Reagent B was then added to each well, and incubated for 1 h at 37° C. Detection Reagent B was then removed and wells were washed five times with 300 μL of 1× Wash Buffer. Following aspiration of all the Wash Buffer, 90 μL of Substrate Solution was added to each well and then incubated at 37° C. for 10-20 min. When a suitable colour change was achieved, 50 μL of Stop Solution was added. The absorbance was then immediately read at 450 nm (Omega, BMG LabTech Ltd). A standard curve was generated by plotting the mean absorbance, of duplicate standard wells, against known standard concentrations, and generating a line of best fit. Serum sample FKBP-L concentrations were then calculated.

The % Coefficient of Variation (% CV) was calculated to ensure there were no large variances between duplicate wells. Serum samples with a CV greater than 20% were excluded from the study.

Figure 14:
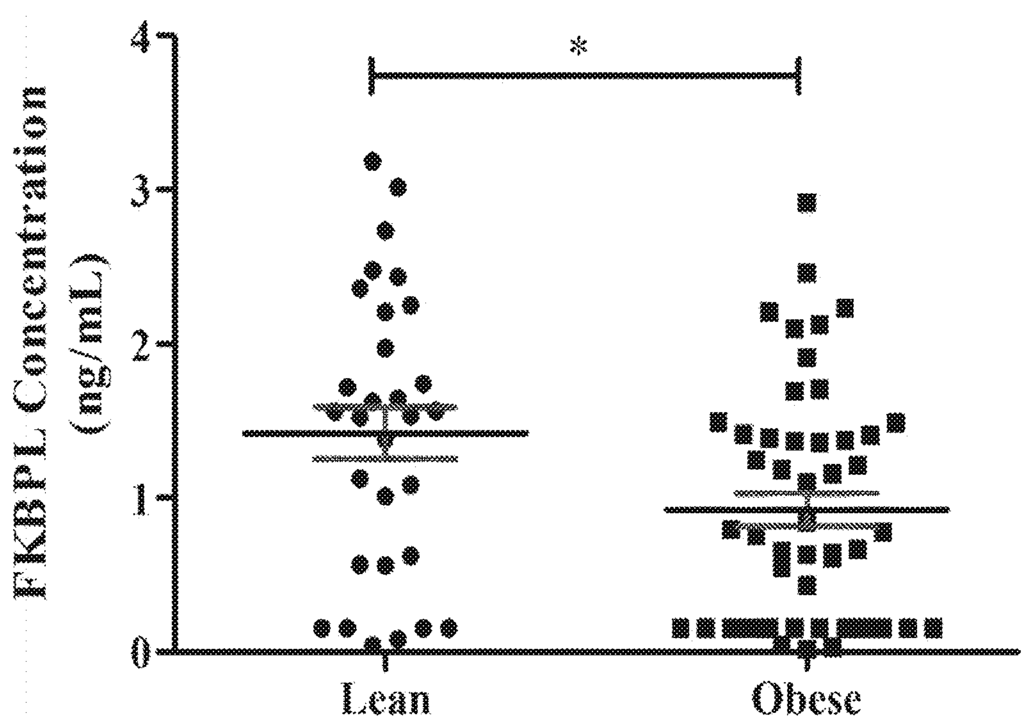
FIG. 14 illustrates low serum FKBP-L, measured by ELISA, is associated with childhood obesity.

FIG. 14 demonstrates that FKBP-L are also associated with an obese phenotype. Lean children had a serum FKBP-L concentration of 1.423 ng/mL±0.1694. Obese children had a significantly lower serum FKBP-L concentration than lean children (0.9239 ng/mL±0.1078).

Figure 15:
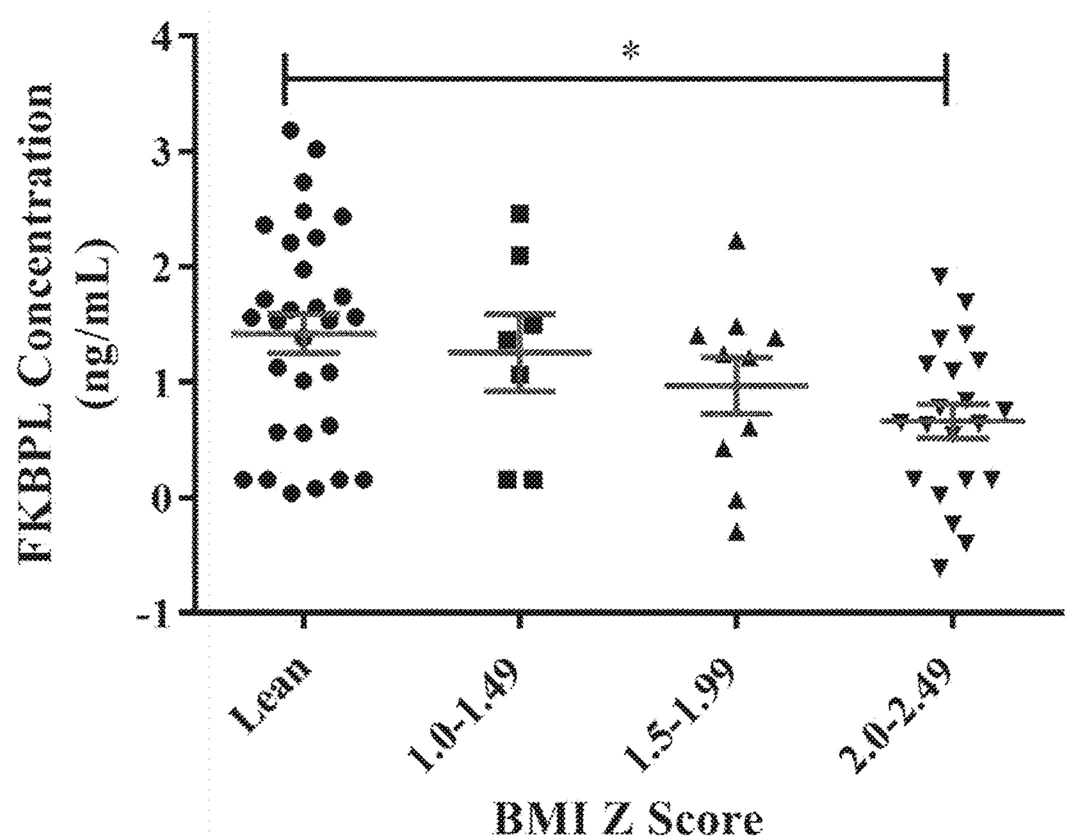
FIG. 15 illustrates low serum FKBP-L, measured by ELISA, correlates with high BMI score in children.

FIG. 15 shows that FKBP-L levels also significantly correlate with BMI Z score in these children; with FKBP-L levels falling as BMI Z scores increase. Obese children with a BMI Z Score, in the range 2.0-2.49, have a significantly lower serum FKBP-L concentration than lean children (0.6633 ng/mL±0.1482 and 1.423 ng/mL±0.1694, respectively). It is proposed that FKBP-L could be used as a predictive biomarker for predisposition to obesity or to identify individuals who might benefit from treatment with FKBP-L-based therapy.

Although the invention has been particularly shown and described with reference to particular examples, it will be understood by those skilled in the art that various changes in the form and details may be made therein without departing from the scope of the present invention.

The invention claimed is:

1. A method of treating obesity comprising the step of administering to a subject in need thereof, a FK506-binding protein like (FKBP-L) nucleic acid or polypeptide, wherein the FKBP-L nucleic acid or polypeptide is selected from the group consisting of:

(a) a FKBP-L polypeptide encoded by the nucleotide sequence of SEQ ID NO: 30;

(b) a FKBP-L polypeptide that consists of the amino acid sequence NH2-TIRQQPRDPPTETLELEVSPDPAS-OH (SEQ ID NO: 40);

(c) a FKBP-L polypeptide that consists of the amino acid sequence NH2-QIRQQPRDPPTETLELEVSPDPAS-OH (SEQ ID NO: 10);

(d) a nucleic acid capable of being expressed to provide a FKBP-L polypeptide that consists of the amino acid sequence NH2-IRQQPRDPPTETLELEVSPDPAS-OH (SEQ ID NO:40); and (e) a nucleic acid capable of being expressed to provide a FKBP-L polypeptide that consists of the amino acid sequence NH2-QIRQQPRDPPTETLELEVSPDPAS-OH (SEQ ID NO: 10).

2. The method of claim 1, wherein the nucleic acid or polypeptide sequence further comprises a delivery peptide.

3. The method of claim 2, wherein the delivery peptide is an RALA peptide.

* * * * *

SEQUENCE LISTING

<160> NUMBER OF SEQ ID NOS: 43

<210> SEQ ID NO 1
<211> LENGTH: 385
<212> TYPE: PRT
<213> ORGANISM: Homo sapiens

<400> SEQUENCE: 1

Met Arg Gly Ser His His His His His His Gly Met Ala Ser Met Thr
1 5 10 15

Gly Gly Gln Gln Met Gly Arg Asp Leu Tyr Asp Asp Asp Asp Lys Asp
20 25 30

Arg Trp Gly Ser Met Glu Thr Pro Pro Val Asn Thr Ile Gly Glu Lys
35 40 45

Asp Thr Ser Gln Pro Gln Gln Glu Trp Glu Lys Asn Leu Arg Glu Asn
50 55 60

Leu Asp Ser Val Ile Gln Ile Arg Gln Gln Pro Arg Asp Pro Pro Thr
65 70 75 80

Glu Thr Leu Glu Leu Glu Val Ser Pro Asp Pro Ala Ser Gln Ile Leu
85 90 95

Glu His Thr Gln Gly Ala Glu Lys Leu Val Ala Glu Leu Glu Gly Asp
100 105 110

Ser His Lys Ser His Gly Ser Thr Ser Gln Met Pro Glu Ala Leu Gln
115 120 125

Ala Ser Asp Leu Trp Tyr Cys Pro Asp Gly Ser Phe Val Lys Lys Ile
130 135 140

Val Ile Arg Gly His Gly Leu Asp Lys Pro Lys Leu Gly Ser Cys Cys
145 150 155 160

Arg Val Leu Ala Leu Gly Phe Pro Phe Gly Ser Gly Pro Pro Glu Gly
165 170 175

Trp Thr Glu Leu Thr Met Gly Val Gly Pro Trp Arg Glu Glu Thr Trp
180 185 190

Gly Glu Leu Ile Glu Lys Cys Leu Glu Ser Met Cys Gln Gly Glu Glu
195 200 205

Ala Glu Leu Gln Leu Pro Gly His Thr Gly Pro Pro Val Gly Leu Thr
210 215 220

Leu Ala Ser Phe Thr Gln Gly Arg Asp Ser Trp Glu Leu Glu Thr Ser
225 230 235 240

Glu Lys Glu Ala Leu Ala Arg Glu Glu Arg Ala Arg Gly Thr Glu Leu
245 250 255

Phe Arg Ala Gly Asn Pro Glu Gly Ala Ala Arg Cys Tyr Gly Arg Ala
260 265 270

Leu Arg Leu Leu Leu Thr Leu Pro Pro Pro Gly Pro Pro Glu Arg Thr
275 280 285

Val Leu His Ala Asn Leu Ala Ala Cys Gln Leu Leu Leu Gly Gln Pro
290 295 300

```
Gln Leu Ala Ala Gln Ser Cys Asp Arg Val Leu Glu Arg Glu Pro Gly
305                 310                 315                 320

His Leu Lys Ala Leu Tyr Arg Arg Gly Val Ala Gln Ala Ala Leu Gly
                325                 330                 335

Asn Leu Glu Lys Ala Thr Ala Asp Leu Lys Lys Val Leu Ala Ile Asp
            340                 345                 350

Pro Lys Asn Arg Ala Ala Gln Glu Glu Leu Gly Lys Val Val Ile Gln
        355                 360                 365

Gly Lys Asn Gln Asp Ala Gly Leu Ala Gln Gly Leu Arg Lys Met Phe
    370                 375                 380

Gly
385


<210> SEQ ID NO 2
<211> LENGTH: 349
<212> TYPE: PRT
<213> ORGANISM: Homo sapiens

<400> SEQUENCE: 2

Met Glu Thr Pro Pro Val Asn Thr Ile Gly Glu Lys Asp Thr Ser Gln
1               5                   10                  15

Pro Gln Gln Glu Trp Glu Lys Asn Leu Arg Glu Asn Leu Asp Ser Val
            20                  25                  30

Ile Gln Ile Arg Gln Gln Pro Arg Asp Pro Pro Thr Glu Thr Leu Glu
        35                  40                  45

Leu Glu Val Ser Pro Asp Pro Ala Ser Gln Ile Leu Glu His Thr Gln
    50                  55                  60

Gly Ala Glu Lys Leu Val Ala Glu Leu Glu Gly Asp Ser His Lys Ser
65                  70                  75                  80

His Gly Ser Thr Ser Gln Met Pro Glu Ala Leu Gln Ala Ser Asp Leu
                85                  90                  95

Trp Tyr Cys Pro Asp Gly Ser Phe Val Lys Lys Ile Val Ile Arg Gly
            100                 105                 110

His Gly Leu Asp Lys Pro Lys Leu Gly Ser Cys Cys Arg Val Leu Ala
        115                 120                 125

Leu Gly Phe Pro Phe Gly Ser Gly Pro Pro Glu Gly Trp Thr Glu Leu
    130                 135                 140

Thr Met Gly Val Gly Pro Trp Arg Glu Glu Thr Trp Gly Glu Leu Ile
145                 150                 155                 160

Glu Lys Cys Leu Glu Ser Met Cys Gln Gly Glu Glu Ala Glu Leu Gln
                165                 170                 175

Leu Pro Gly His Thr Gly Pro Pro Val Gly Leu Thr Leu Ala Ser Phe
            180                 185                 190

Thr Gln Gly Arg Asp Ser Trp Glu Leu Glu Thr Ser Glu Lys Glu Ala
        195                 200                 205

Leu Ala Arg Glu Glu Arg Ala Arg Gly Thr Glu Leu Phe Arg Ala Gly
    210                 215                 220

Asn Pro Glu Gly Ala Ala Arg Cys Tyr Gly Arg Ala Leu Arg Leu Leu
225                 230                 235                 240

Leu Thr Leu Pro Pro Pro Gly Pro Pro Glu Arg Thr Val Leu His Ala
                245                 250                 255

Asn Leu Ala Ala Cys Gln Leu Leu Leu Gly Gln Pro Gln Leu Ala Ala
            260                 265                 270

Gln Ser Cys Asp Arg Val Leu Glu Arg Glu Pro Gly His Leu Lys Ala
```

```
        275                 280                 285

Leu Tyr Arg Arg Gly Val Ala Gln Ala Ala Leu Gly Asn Leu Glu Lys
    290                 295                 300

Ala Thr Ala Asp Leu Lys Lys Val Leu Ala Ile Asp Pro Lys Asn Arg
305                 310                 315                 320

Ala Ala Gln Glu Glu Leu Gly Lys Val Val Ile Gln Gly Lys Asn Gln
                325                 330                 335

Asp Ala Gly Leu Ala Gln Gly Leu Arg Lys Met Phe Gly
            340                 345


<210> SEQ ID NO 3
<211> LENGTH: 199
<212> TYPE: PRT
<213> ORGANISM: Artificial Sequence
<220> FEATURE:
<223> OTHER INFORMATION: Delta 200

<400> SEQUENCE: 3

Met Glu Thr Pro Pro Val Asn Thr Ile Gly Glu Lys Asp Thr Ser Gln
1               5                   10                  15

Pro Gln Gln Glu Trp Glu Lys Asn Leu Arg Glu Asn Leu Asp Ser Val
            20                  25                  30

Ile Gln Ile Arg Gln Gln Pro Arg Asp Pro Pro Thr Glu Thr Leu Glu
        35                  40                  45

Leu Glu Val Ser Pro Asp Pro Ala Ser Gln Ile Leu Glu His Thr Gln
    50                  55                  60

Gly Ala Glu Lys Leu Val Ala Glu Leu Glu Gly Asp Ser His Lys Ser
65                  70                  75                  80

His Gly Ser Thr Ser Gln Met Pro Glu Ala Leu Gln Ala Ser Asp Leu
                85                  90                  95

Trp Tyr Cys Pro Asp Gly Ser Phe Val Lys Lys Ile Val Ile Arg Gly
            100                 105                 110

His Gly Leu Asp Lys Pro Lys Leu Gly Ser Cys Cys Arg Val Leu Ala
        115                 120                 125

Leu Gly Phe Pro Phe Gly Ser Gly Pro Pro Glu Gly Trp Thr Glu Leu
    130                 135                 140

Thr Met Gly Val Gly Pro Trp Arg Glu Glu Thr Trp Gly Glu Leu Ile
145                 150                 155                 160

Glu Lys Cys Leu Glu Ser Met Cys Gln Gly Glu Glu Ala Glu Leu Gln
                165                 170                 175

Leu Pro Gly His Thr Gly Pro Pro Val Gly Leu Thr Leu Ala Ser Phe
            180                 185                 190

Thr Gln Gly Arg Asp Ser Trp
        195


<210> SEQ ID NO 4
<211> LENGTH: 150
<212> TYPE: PRT
<213> ORGANISM: Artificial Sequence
<220> FEATURE:
<223> OTHER INFORMATION: Delta 151

<400> SEQUENCE: 4

Met Glu Thr Pro Pro Val Asn Thr Ile Gly Glu Lys Asp Thr Ser Gln
1               5                   10                  15

Pro Gln Gln Glu Trp Glu Lys Asn Leu Arg Glu Asn Leu Asp Ser Val
            20                  25                  30
```

```
Ile Gln Ile Arg Gln Gln Pro Arg Asp Pro Pro Thr Glu Thr Leu Glu
        35                  40                  45

Leu Glu Val Ser Pro Asp Pro Ala Ser Gln Ile Leu Glu His Thr Gln
    50                  55                  60

Gly Ala Glu Lys Leu Val Ala Glu Leu Glu Gly Asp Ser His Lys Ser
65                  70                  75                  80

His Gly Ser Thr Ser Gln Met Pro Glu Ala Leu Gln Ala Ser Asp Leu
                85                  90                  95

Trp Tyr Cys Pro Asp Gly Ser Phe Val Lys Lys Ile Val Ile Arg Gly
            100                 105                 110

His Gly Leu Asp Lys Pro Lys Leu Gly Ser Cys Cys Arg Val Leu Ala
        115                 120                 125

Leu Gly Phe Pro Phe Gly Ser Gly Pro Pro Glu Gly Trp Thr Glu Leu
    130                 135                 140

Thr Met Gly Val Gly Pro
145                 150


<210> SEQ ID NO 5
<211> LENGTH: 85
<212> TYPE: PRT
<213> ORGANISM: Artificial Sequence
<220> FEATURE:
<223> OTHER INFORMATION: Delta 86

<400> SEQUENCE: 5

Met Glu Thr Pro Pro Val Asn Thr Ile Gly Glu Lys Asp Thr Ser Gln
1               5                   10                  15

Pro Gln Gln Glu Trp Glu Lys Asn Leu Arg Glu Asn Leu Asp Ser Val
            20                  25                  30

Ile Gln Ile Arg Gln Gln Pro Arg Asp Pro Pro Thr Glu Thr Leu Glu
        35                  40                  45

Leu Glu Val Ser Pro Asp Pro Ala Ser Gln Ile Leu Glu His Thr Gln
    50                  55                  60

Gly Ala Glu Lys Leu Val Ala Glu Leu Glu Gly Asp Ser His Lys Ser
65                  70                  75                  80

His Gly Ser Thr Ser
                85


<210> SEQ ID NO 6
<211> LENGTH: 57
<212> TYPE: PRT
<213> ORGANISM: Artificial Sequence
<220> FEATURE:
<223> OTHER INFORMATION: Delta 58

<400> SEQUENCE: 6

Met Glu Thr Pro Pro Val Asn Thr Ile Gly Glu Lys Asp Thr Ser Gln
1               5                   10                  15

Pro Gln Gln Glu Trp Glu Lys Asn Leu Arg Glu Asn Leu Asp Ser Val
            20                  25                  30

Ile Gln Ile Arg Gln Gln Pro Arg Asp Pro Pro Thr Glu Thr Leu Glu
        35                  40                  45

Leu Glu Val Ser Pro Asp Pro Ala Ser
    50                  55


<210> SEQ ID NO 7
<211> LENGTH: 47
<212> TYPE: PRT
<213> ORGANISM: Artificial Sequence
```

```
<220> FEATURE:
<223> OTHER INFORMATION: Delta 48

<400> SEQUENCE: 7

Met Glu Thr Pro Pro Val Asn Thr Ile Gly Glu Lys Asp Thr Ser Gln
1               5                   10                  15

Pro Gln Gln Glu Trp Glu Lys Asn Leu Arg Glu Asn Leu Asp Ser Val
            20                  25                  30

Ile Gln Ile Arg Gln Gln Pro Arg Asp Pro Pro Thr Glu Thr Leu
        35                  40                  45


<210> SEQ ID NO 8
<211> LENGTH: 39
<212> TYPE: PRT
<213> ORGANISM: Artificial Sequence
<220> FEATURE:
<223> OTHER INFORMATION: Delta 40

<400> SEQUENCE: 8

Met Glu Thr Pro Pro Val Asn Thr Ile Gly Glu Lys Asp Thr Ser Gln
1               5                   10                  15

Pro Gln Gln Glu Trp Glu Lys Asn Leu Arg Glu Asn Leu Asp Ser Val
            20                  25                  30

Ile Gln Ile Arg Gln Gln Pro
        35


<210> SEQ ID NO 9
<211> LENGTH: 33
<212> TYPE: PRT
<213> ORGANISM: Artificial Sequence
<220> FEATURE:
<223> OTHER INFORMATION: Delta 34

<400> SEQUENCE: 9

Met Glu Thr Pro Pro Val Asn Thr Ile Gly Glu Lys Asp Thr Ser Gln
1               5                   10                  15

Pro Gln Gln Glu Trp Glu Lys Asn Leu Arg Glu Asn Leu Asp Ser Val
            20                  25                  30

Ile


<210> SEQ ID NO 10
<211> LENGTH: 24
<212> TYPE: PRT
<213> ORGANISM: Artificial Sequence
<220> FEATURE:
<223> OTHER INFORMATION: AD-01
<220> FEATURE:
<221> NAME/KEY: MISC_FEATURE
<222> LOCATION: (1)..()
<223> OTHER INFORMATION: NH2
<220> FEATURE:
<221> NAME/KEY: MISC_FEATURE
<222> LOCATION: (23)..()
<223> OTHER INFORMATION: OH

<400> SEQUENCE: 10

Gln Ile Arg Gln Gln Pro Arg Asp Pro Pro Thr Glu Thr Leu Glu Leu
1               5                   10                  15

Glu Val Ser Pro Asp Pro Ala Ser
            20


<210> SEQ ID NO 11
<211> LENGTH: 18
<212> TYPE: PRT
```

<213> ORGANISM: Artificial Sequence
<220> FEATURE:
<223> OTHER INFORMATION: peptide

<400> SEQUENCE: 11

Gln Gln Pro Arg Asp Pro Pro Thr Glu Thr Leu Glu Leu Glu Val Ser
1 5 10 15

Pro Asp

<210> SEQ ID NO 12
<211> LENGTH: 25
<212> TYPE: PRT
<213> ORGANISM: Artificial Sequence
<220> FEATURE:
<223> OTHER INFORMATION: peptide 1

<400> SEQUENCE: 12

Gln Ile Arg Gln Gln Pro Arg Asp Pro Pro Thr Glu Thr Leu Glu Leu
1 5 10 15

Glu Val Ser Pro Asp Pro Ala Ser Cys
20 25

<210> SEQ ID NO 13
<211> LENGTH: 24
<212> TYPE: PRT
<213> ORGANISM: Artificial Sequence
<220> FEATURE:
<223> OTHER INFORMATION: peptide 2

<400> SEQUENCE: 13

Glu Ile Arg Gln Gln Pro Arg Asp Pro Pro Thr Glu Thr Leu Glu Leu
1 5 10 15

Glu Val Ser Pro Asp Pro Ala Ser
20

<210> SEQ ID NO 14
<211> LENGTH: 23
<212> TYPE: PRT
<213> ORGANISM: Artificial Sequence
<220> FEATURE:
<223> OTHER INFORMATION: peptide 3

<400> SEQUENCE: 14

Ile Arg Gln Gln Pro Arg Asp Pro Pro Thr Glu Thr Leu Glu Leu Glu
1 5 10 15

Val Ser Pro Asp Pro Ala Ser
20

<210> SEQ ID NO 15
<211> LENGTH: 21
<212> TYPE: PRT
<213> ORGANISM: Artificial Sequence
<220> FEATURE:
<223> OTHER INFORMATION: peptide 4

<400> SEQUENCE: 15

Gln Ile Arg Gln Gln Pro Arg Asp Pro Pro Thr Glu Thr Leu Glu Leu
1 5 10 15

Glu Val Ser Pro Asp
20

<210> SEQ ID NO 16
<211> LENGTH: 18
<212> TYPE: PRT

<213> ORGANISM: Artificial Sequence
<220> FEATURE:
<223> OTHER INFORMATION: peptide 5

<400> SEQUENCE: 16

Gln Ile Arg Gln Gln Pro Arg Asp Pro Pro Thr Glu Thr Leu Glu Leu
1 5 10 15

Glu Val

<210> SEQ ID NO 17
<211> LENGTH: 15
<212> TYPE: PRT
<213> ORGANISM: Artificial Sequence
<220> FEATURE:
<223> OTHER INFORMATION: peptide 6

<400> SEQUENCE: 17

Gln Ile Arg Gln Gln Pro Arg Asp Pro Pro Thr Glu Thr Leu Glu
1 5 10 15

<210> SEQ ID NO 18
<211> LENGTH: 12
<212> TYPE: PRT
<213> ORGANISM: Artificial Sequence
<220> FEATURE:
<223> OTHER INFORMATION: peptide 7

<400> SEQUENCE: 18

Gln Ile Arg Gln Gln Pro Arg Asp Pro Pro Thr Glu
1 5 10

<210> SEQ ID NO 19
<211> LENGTH: 21
<212> TYPE: PRT
<213> ORGANISM: Artificial Sequence
<220> FEATURE:
<223> OTHER INFORMATION: peptide 8

<400> SEQUENCE: 19

Gln Gln Pro Arg Asp Pro Pro Thr Glu Thr Leu Glu Leu Glu Val Ser
1 5 10 15

Pro Asp Pro Ala Ser
20

<210> SEQ ID NO 20
<211> LENGTH: 18
<212> TYPE: PRT
<213> ORGANISM: Artificial Sequence
<220> FEATURE:
<223> OTHER INFORMATION: peptide 9

<400> SEQUENCE: 20

Arg Asp Pro Pro Thr Glu Thr Leu Glu Leu Glu Val Ser Pro Asp Pro
1 5 10 15

Ala Ser

<210> SEQ ID NO 21
<211> LENGTH: 15
<212> TYPE: PRT
<213> ORGANISM: Artificial Sequence
<220> FEATURE:
<223> OTHER INFORMATION: peptide 10

<400> SEQUENCE: 21

Pro Thr Glu Thr Leu Glu Leu Glu Val Ser Pro Asp Pro Ala Ser 1 5 10 15

<210> SEQ ID NO 22
<211> LENGTH: 12
<212> TYPE: PRT
<213> ORGANISM: Artificial Sequence
<220> FEATURE:
<223> OTHER INFORMATION: peptide 11

<400> SEQUENCE: 22

Thr Leu Glu Leu Glu Val Ser Pro Asp Pro Ala Ser
1 5 10

<210> SEQ ID NO 23
<211> LENGTH: 19
<212> TYPE: PRT
<213> ORGANISM: Artificial Sequence
<220> FEATURE:
<223> OTHER INFORMATION: peptide 12

<400> SEQUENCE: 23

Arg Gln Gln Pro Arg Asp Pro Pro Thr Glu Thr Leu Glu Leu Glu Val
1 5 10 15

Ser Pro Asp

<210> SEQ ID NO 24
<211> LENGTH: 18
<212> TYPE: PRT
<213> ORGANISM: Artificial Sequence
<220> FEATURE:
<223> OTHER INFORMATION: peptide 13

<400> SEQUENCE: 24

Arg Gln Gln Pro Arg Asp Pro Pro Thr Glu Thr Leu Glu Leu Glu Val
1 5 10 15

Ser Pro

<210> SEQ ID NO 25
<211> LENGTH: 17
<212> TYPE: PRT
<213> ORGANISM: Artificial Sequence
<220> FEATURE:
<223> OTHER INFORMATION: peptide 14

<400> SEQUENCE: 25

Arg Gln Gln Pro Arg Asp Pro Pro Thr Glu Thr Leu Glu Leu Glu Val
1 5 10 15

Ser

<210> SEQ ID NO 26
<211> LENGTH: 16
<212> TYPE: PRT
<213> ORGANISM: Artificial Sequence
<220> FEATURE:
<223> OTHER INFORMATION: peptide 15

<400> SEQUENCE: 26

Pro Arg Asp Pro Pro Thr Glu Thr Leu Glu Leu Glu Val Ser Pro Asp
1 5 10 15

<210> SEQ ID NO 27
<211> LENGTH: 15
<212> TYPE: PRT
<213> ORGANISM: Artificial Sequence
<220> FEATURE:

<223> OTHER INFORMATION: peptide 16

<400> SEQUENCE: 27

```
Arg Asp Pro Pro Thr Glu Thr Leu Glu Leu Glu Val Ser Pro Asp
1               5                   10                  15
```

<210> SEQ ID NO 28
<211> LENGTH: 24
<212> TYPE: PRT
<213> ORGANISM: Artificial Sequence
<220> FEATURE:
<223> OTHER INFORMATION: peptide 17

<400> SEQUENCE: 28

```
Gln Ile Arg Gln Gln Pro Arg Asp Pro Pro Thr Glu Thr Leu Glu Leu
1               5                   10                  15

Glu Val Ser Pro Asp Pro Ala Ser
            20
```

<210> SEQ ID NO 29
<211> LENGTH: 349
<212> TYPE: PRT
<213> ORGANISM: Homo sapiens

<400> SEQUENCE: 29

```
Met Glu Thr Pro Pro Val Asn Thr Ile Gly Glu Lys Asp Thr Ser Gln
1               5                   10                  15

Pro Gln Gln Glu Trp Glu Lys Asn Leu Arg Glu Asn Leu Asp Ser Val
            20                  25                  30

Ile Gln Ile Arg Gln Gln Pro Arg Asp Pro Pro Thr Glu Thr Leu Glu
        35                  40                  45

Leu Glu Val Ser Pro Asp Pro Ala Ser Gln Ile Leu Glu His Thr Gln
    50                  55                  60

Gly Ala Glu Lys Leu Val Ala Glu Leu Glu Gly Asp Ser His Lys Ser
65                  70                  75                  80

His Gly Ser Thr Ser Gln Met Pro Glu Ala Leu Gln Ala Ser Asp Leu
                85                  90                  95

Trp Tyr Cys Pro Asp Gly Ser Phe Val Lys Lys Ile Val Ile Arg Gly
            100                 105                 110

His Gly Leu Asp Lys Pro Lys Leu Gly Ser Cys Cys Arg Val Leu Ala
        115                 120                 125

Leu Gly Phe Pro Phe Gly Ser Gly Pro Pro Glu Gly Trp Thr Glu Leu
    130                 135                 140

Thr Met Gly Val Gly Pro Trp Arg Glu Glu Thr Trp Gly Glu Leu Ile
145                 150                 155                 160

Glu Lys Cys Leu Glu Ser Met Cys Gln Gly Glu Glu Ala Glu Leu Gln
                165                 170                 175

Leu Pro Gly His Ser Gly Pro Pro Val Arg Leu Thr Leu Ala Ser Phe
            180                 185                 190

Thr Gln Gly Arg Asp Ser Trp Glu Leu Glu Thr Ser Glu Lys Glu Ala
        195                 200                 205

Leu Ala Arg Glu Glu Arg Ala Arg Gly Thr Glu Leu Phe Arg Ala Gly
    210                 215                 220

Asn Pro Glu Gly Ala Ala Arg Cys Tyr Gly Arg Ala Leu Arg Leu Leu
225                 230                 235                 240

Leu Thr Leu Pro Pro Pro Gly Pro Pro Glu Arg Thr Val Leu His Ala
                245                 250                 255
```

```
Asn Leu Ala Ala Cys Gln Leu Leu Leu Gly Gln Pro Gln Leu Ala Ala
            260                 265                 270

Gln Ser Cys Asp Arg Val Leu Glu Arg Glu Pro Gly His Leu Lys Ala
        275                 280                 285

Leu Tyr Arg Arg Gly Val Ala Gln Ala Ala Leu Gly Asn Leu Glu Lys
    290                 295                 300

Ala Thr Ala Asp Leu Lys Lys Val Leu Ala Ile Asp Pro Lys Asn Arg
305                 310                 315                 320

Ala Ala Gln Glu Glu Leu Gly Lys Val Val Ile Gln Gly Lys Asn Gln
                325                 330                 335

Asp Ala Gly Leu Ala Gln Gly Leu Arg Lys Met Phe Gly
            340                 345


<210> SEQ ID NO 30
<211> LENGTH: 1050
<212> TYPE: DNA
<213> ORGANISM: Homo sapiens

<400> SEQUENCE: 30

atggagacgc caccagtcaa tacaattgga gaaaaggaca cctctcagcc gcaacaagag      60

tgggaaaaga accttcggga gaaccttgat tcagttattc agattaggca gcagccccga     120

gaccctccta ccgaaacgct tgagctggaa gtaagcccag atccagccag ccaaattcta     180

gagcatactc aaggagctga aaaactggtt gctgaacttg aaggagactc tcataagtct     240

catggatcaa ccagtcagat gccagaggcc cttcaagctt ctgatctctg gtactgcccc     300

gatgggagct ttgtcaagaa gatcgtaatc cgtggccatg gcttggacaa acccaaacta     360

ggctcctgct gccgggtact ggctttgggg tttcctttcg gatcagggcc gccagagggc     420

tggacagagc taactatggg cgtagggcca tggagggagg aaacttgggg ggagctcata     480

gagaaatgct tggagtccat gtgtcaaggt gaggaagcag agcttcagct gcctgggcac     540

tctggacctc ctgtcaggct cacactggca tccttcactc aaggccgaga ctcctgggag     600

ctggagacta gcgagaagga agccctggcc agggaagaac gtgcaagggg cacagaacta     660

tttcgagctg ggaaccctga aggagctgcc cgatgctatg gacgggctct tcggctgctc     720

ctgactttac ccccacctgg ccctccagaa cgaactgtcc ttcatgccaa tctggctgcc     780

tgtcagttgt tgctagggca gcctcagttg gcagcccaga gctgtgaccg ggtgttggag     840

cgggagcctg gccatttaaa ggccttatac cgaagggggg ttgcccaggc tgcccttggg     900

aacctggaaa aagcaactgc tgacctcaag aaggtgctgg cgatagatcc caaaaaccgg     960

gcagcccagg aggaactggg gaaggtggtc attcagggga agaaccagga tgcagggctg    1020

gctcagggtc tgcgcaagat gtttggctga                                     1050


<210> SEQ ID NO 31
<211> LENGTH: 1050
<212> TYPE: DNA
<213> ORGANISM: Homo sapiens

<400> SEQUENCE: 31

atggagacgc caccagtcaa tacaattgga gaaaaggaca cctctcagcc gcaacaagag      60

tgggaaaaga accttcggga gaaccttgat tcagttattc agattaggca gcagccccga     120

gaccctccta ccgaaacgct tgagctggaa gtaagcccag atccagccag ccaaattcta     180

gagcatactc aaggagctga aaaactggtt gctgaacttg aaggagactc tcataagtct     240

catggatcaa ccagtcagat gccagaggcc cttcaagctt ctgatctctg gtactgcccc     300
```

gatgggagct ttgtcaagaa gatcgtaatc cgtggccatg gcttggacaa acccaaacta 360
ggctcctgct gccgggtact ggctttgggg tttcctttcg gatcagggcc gccagagggc 420
tggacagagc taactatggg cgtagggcca tggagggagg aaacttgggg ggagctcata 480
gagaaatgct tggagtccat gtgtcaaggt gaggaagcag agcttcagct gcctgggcac 540
actggacctc ctgtcgggct cacactggca tccttcactc aaggccgaga ctcctgggag 600
ctggagacta gcgagaagga agccctggcc agggaagaac gtgcaagggg cacagaacta 660
tttcgagctg ggaaccctga aggagctgcc cgatgctatg gacgggctct tcggctgctc 720
ctgactttac ccccacctgg ccctccagaa cgaactgtcc ttcatgccaa tctggctgcc 780
tgtcagttgt tgctagggca gcctcagttg gcagcccaga gctgtgaccg ggtgttggag 840
cgggagcctg gccatttaaa ggccttatac cgaagggggg ttgcccaggc tgcccttggg 900
aacctggaaa aagcaactgc tgacctcaag aaggtgctgg cgatagatcc caaaaaccgg 960
gcagcccagg aggaactggg gaaggtggtc attcagggga agaaccagga tgcagggctg 1020
gctcagggtc tgcgcaagat gtttggctga 1050

<210> SEQ ID NO 32
<211> LENGTH: 102
<212> TYPE: DNA
<213> ORGANISM: Artificial Sequence
<220> FEATURE:
<223> OTHER INFORMATION: Delta 34

<400> SEQUENCE: 32
atggagacgc caccagtcaa tacaattgga gaaaaggaca cctctcagcc gcaacaagag 60
tgggaaaaga accttcggga gaaccttgat tcagttattt ag 102

<210> SEQ ID NO 33
<211> LENGTH: 119
<212> TYPE: DNA
<213> ORGANISM: Artificial Sequence
<220> FEATURE:
<223> OTHER INFORMATION: Delta 40

<400> SEQUENCE: 33
atggagacgc caccagtcaa tacaattgga gaaaaggaca cctctcagcc gcaacaagag 60
tgggaaaaga accttcggga gaaccttgat tcagttattc agattaggca gcagccccg 119

<210> SEQ ID NO 34
<211> LENGTH: 143
<212> TYPE: DNA
<213> ORGANISM: Artificial Sequence
<220> FEATURE:
<223> OTHER INFORMATION: Delta 48

<400> SEQUENCE: 34
atggagacgc caccagtcaa tacaattgga gaaaaggaca cctctcagcc gcaacaagag 60
tgggaaaaga accttcggga gaaccttgat tcagttattc agattaggca gcagccccga 120
gaccctccta ccgaaacgct tga 143

<210> SEQ ID NO 35
<211> LENGTH: 174
<212> TYPE: DNA
<213> ORGANISM: Artificial Sequence
<220> FEATURE:
<223> OTHER INFORMATION: Delta 58

<400> SEQUENCE: 35

```
atggagacgc caccagtcaa tacaattgga gaaaaggaca cctctcagcc gcaacaagag     60
tgggaaaaga accttcggga gaaccttgat tcagttattc agattaggca gcagccccga    120
gaccctccta ccgaaacgct tgagctggaa gtaagcccag atccagccag ctaa          174
```

<210> SEQ ID NO 36
<211> LENGTH: 258
<212> TYPE: DNA
<213> ORGANISM: Artificial Sequence
<220> FEATURE:
<223> OTHER INFORMATION: Delta 86

<400> SEQUENCE: 36

```
atggagacgc caccagtcaa tacaattgga gaaaaggaca cctctcagcc gcaacaagag     60
tgggaaaaga accttcggga gaaccttgat tcagttattc agattaggca gcagccccga    120
gaccctccta ccgaaacgct tgagctggaa gtaagcccag atccagccag ccaaattcta    180
gagcatactc aaggagctga aaaactggtt gctgaacttg aaggagactc tcataagtct    240
catggatcaa ccagttag                                                  258
```

<210> SEQ ID NO 37
<211> LENGTH: 453
<212> TYPE: DNA
<213> ORGANISM: Artificial Sequence
<220> FEATURE:
<223> OTHER INFORMATION: Delta 151

<400> SEQUENCE: 37

```
atggagacgc caccagtcaa tacaattgga gaaaaggaca cctctcagcc gcaacaagag     60
tgggaaaaga accttcggga gaaccttgat tcagttattc agattaggca gcagccccga    120
gaccctccta ccgaaacgct tgagctggaa gtaagcccag atccagccag ccaaattcta    180
gagcatactc aaggagctga aaaactggtt gctgaacttg aaggagactc tcataagtct    240
catggatcaa ccagtcagat gccagaggcc cttcaagctt ctgatctctg gtactgcccc    300
gatgggagct ttgtcaagaa gatcgtaatc cgtggccatg gcttggacaa acccaaacta    360
ggctcctgct gccgggtact ggctttgggg tttcctttcg gatcagggcc gccagagggc    420
tggacagagc taactatggg cgtagggcca tga                                 453
```

<210> SEQ ID NO 38
<211> LENGTH: 600
<212> TYPE: DNA
<213> ORGANISM: Artificial Sequence
<220> FEATURE:
<223> OTHER INFORMATION: Delta 200

<400> SEQUENCE: 38

```
atggagacgc caccagtcaa tacaattgga gaaaaggaca cctctcagcc gcaacaagag     60
tgggaaaaga accttcggga gaaccttgat tcagttattc agattaggca gcagccccga    120
gaccctccta ccgaaacgct tgagctggaa gtaagcccag atccagccag ccaaattcta    180
gagcatactc aaggagctga aaaactggtt gctgaacttg aaggagactc tcataagtct    240
catggatcaa ccagtcagat gccagaggcc cttcaagctt ctgatctctg gtactgcccc    300
gatgggagct ttgtcaagaa gatcgtaatc cgtggccatg gcttggacaa acccaaacta    360
ggctcctgct gccgggtact ggctttgggg tttcctttcg gatcagggcc gccagagggc    420
tggacagagc taactatggg cgtagggcca tggagggagg aaacttgggg ggagctcata    480
```

```
gagaaatgct tggagtccat gtgtcaaggt gaggaagcag agcttcagct gcctgggcac    540

tctggacctc ctgtcaggct cacactggca tccttcactc aaggccgaga ctcctggtag    600


<210> SEQ ID NO 39
<211> LENGTH: 600
<212> TYPE: DNA
<213> ORGANISM: Artificial Sequence
<220> FEATURE:
<223> OTHER INFORMATION: Delta 200 cloned

<400> SEQUENCE: 39

atggagacgc caccagtcaa tacaattgga gaaaaggaca cctctcagcc gcaacaagag     60

tgggaaaaga accttcggga gaaccttgat tcagttattc agattaggca gcagccccga    120

gaccctccta ccgaaacgct tgagctggaa gtaagcccag atccagccag ccaaattcta    180

gagcatactc aaggagctga aaaactggtt gctgaacttg aaggagactc tcataagtct    240

catggatcaa ccagtcagat gccagaggcc cttcaagctt ctgatctctg gtactgcccc    300

gatgggagct ttgtcaagaa gatcgtaatc cgtggccatg gcttggacaa acccaaacta    360

ggctcctgct gccgggtact ggctttgggg tttcctttcg gatcagggcc gccagagggc    420

tggacagagc taactatggg cgtagggcca tggagggagg aaacttgggg ggagctcata    480

gagaaatgct tggagtccat gtgtcaaggt gaggaagcag agcttcagct gcctgggcac    540

actggacctc ctgtcgggct cacactggca tccttcactc aaggccgaga ctcctggtag    600


<210> SEQ ID NO 40
<211> LENGTH: 23
<212> TYPE: PRT
<213> ORGANISM: Artificial Sequence
<220> FEATURE:
<223> OTHER INFORMATION: ALM201
<220> FEATURE:
<221> NAME/KEY: MISC_FEATURE
<222> LOCATION: (1)..(1)
<223> OTHER INFORMATION: NH2
<220> FEATURE:
<221> NAME/KEY: MISC_FEATURE
<222> LOCATION: (23)..(1)
<223> OTHER INFORMATION: OH

<400> SEQUENCE: 40

Ile Arg Gln Gln Pro Arg Asp Pro Pro Thr Glu Thr Leu Glu Leu Glu
1               5                   10                  15

Val Ser Pro Asp Pro Ala Ser
            20


<210> SEQ ID NO 41
<211> LENGTH: 25
<212> TYPE: RNA
<213> ORGANISM: Artificial Sequence
<220> FEATURE:
<223> OTHER INFORMATION: SiRNA F1

<400> SEQUENCE: 41

ggagacgcca ccagucaaua caauu                                           25


<210> SEQ ID NO 42
<211> LENGTH: 25
<212> TYPE: RNA
<213> ORGANISM: Artificial Sequence
<220> FEATURE:
<223> OTHER INFORMATION: siRNA F2
```

```
<400> SEQUENCE: 42

gcugaacuug aaggagacuc ucaua                                            25


<210> SEQ ID NO 43
<211> LENGTH: 25
<212> TYPE: RNA
<213> ORGANISM: Artificial Sequence
<220> FEATURE:
<223> OTHER INFORMATION: siRNAF3

<400> SEQUENCE: 43

cagccaaauu cuagagcaua cucaa                                            25
```